US006361954B1

(12) United States Patent
Stillman et al.

(10) Patent No.: US 6,361,954 B1
(45) Date of Patent: Mar. 26, 2002

(54) METHODS OF IMMUNOASSAY FOR HUMAN CDC6

(75) Inventors: Bruce Stillman, Cold Spring Harbor, NY (US); R. Sanders Williams, Dallas, TX (US); Juan R. Mendez, Huntington, NY (US)

(73) Assignees: Cold Spring Harbor Laboratory, Cold Spring Harbor, NY (US); The University of Texas System, Austin, TX (US)

(*) Notice: Subject to any disclaimer, the term of this patent is extended or adjusted under 35 U.S.C. 154(b) by 0 days.

(21) Appl. No.: 09/183,266

(22) Filed: Oct. 30, 1998

Related U.S. Application Data

(63) Continuation-in-part of application No. PCT/US97/07333, filed on May 2, 1997, which is a continuation-in-part of application No. 08/648,650, filed on May 15, 1996, now Pat. No. 6,074,819, which is a continuation-in-part of application No. 08/643,034, filed on May 2, 1996, now Pat. No. 5,851, 821.

(51) Int. Cl.$^7$ ..................... G01N 33/53; G01N 33/574; G01N 33/58; G01N 33/60; G01N 33/567
(52) U.S. Cl. ..................... 435/7.1; 435/7.23; 435/7.9; 424/139.1; 424/152.1; 424/172.1; 424/178.1; 424/1.49; 436/504; 436/536; 530/387.9; 530/391.3
(58) Field of Search ..................... 424/139.1, 152.1, 424/172.1, 178.1, 1.49; 530/387.9, 391.3; 435/7.1, 7.23, 7.9; 436/504, 536

(56) References Cited

FOREIGN PATENT DOCUMENTS

| GB | 2 332 515 A | 6/1999 |
|---|---|---|
| JP | 07274971 | 10/1995 |
| WO | 93/10242 | 5/1993 |
| WO | 93/23571 | 11/1993 |
| WO | 94/23029 | 10/1994 |
| WO | 95/16694 | 6/1995 |
| WO | 95/21917 | 8/1995 |
| WO | WO 99/21014 | 4/1999 |

OTHER PUBLICATIONS

Branch, A. D., "A Good Antisense Molecule Is Hard To Find", *TIBS 23:* 45–50, (1998, Feb.).
Yan, et al., "Cdc6 is regulated by E2F and is essential for DNA replication in mammalian cells", *Proc. Natl. Acad. Sci. USA*, 95:3603–3608 (1998).
Williams, et al., "A human protein related to yeast Cdc6p", *Proc. Natl. Acad. Sci. USA*, 94: 142–147 (1997).
Alfred, J., "Molecular Changes Herald a New Era for Cervical Cancer Screening," *Moelcular Medicine Today*, 5:189–190 (1999).
Williams, G., et al., "Improved Cervical Smear Assessment Using Antibodies Against Proteins That Regulate DNA Replication," *Medical Sciences*, 95:14932–14937 (1998).

Bell, S.P., et al., "The Multidomain Structure of ORC1p Reveals Similarity to Regulators of DNA Replication and Transciptional Silencing," Cell, 83:563 (1995).
Bruschi, C.V., et al., "The Genomic Instability of Yeast cdc6–1/cdc6–1 Mutants Involves Chromosome Structure and Recombination," Mol. Gen. Genet., 249:8–18 (1996).
Bueno, A. and Russell, P., "Dual Functions of CDC6: a Yeast Protein Required for DNA Replication Also Inhibits Nuclear Division," EMBO, 11:2167–2176 (1992).
Cocker, J.H., et al., "An Essential Role for the Cdc6 Protein in Forming the Pre–Replicative Complexes of Budding Yeast," Nature, 379:180 (1996).
Gavin, K.A., et al., "Conserved Initiator Proteins in Eukaryotes," Science, 270:1667–1671 (1995).
Hartwell, J., "Sequential Function of Gene Products Relative to DNA Synthesis in the Yeast Cell Cycle," J. Mol. Biol., 15:803–817 (1976).
Hogan, E. and Koshland, D., "Addition of Extra Origins of Replication to a Minochromosome Suppresses its Mitotic Loss in cdc6 and cdc14 Mutant of *Saccharomyces cerevisiae*," PNAS, 89:3098–3102 (1992).
Jallepalli, P. and Kelly, T., "RumI and Cdc18 Link Inhibition of Cyclin–Dependent Kinases to the Initiation of DNA Replication in *S. pombe.*," Genes and Development, 10:541–552 (1996).
Kelly, T.J., et al., "The Fission Yeast cdc18+Gene Product Couples S. Phase to Start and Mitosis," Cell, 74:371–382 (1993).
Kelly, T.J., et al., "Coupling DNA Replication to the Cell Cycle," Cold Spring Harbor Symp Quant. Biol., 58:637–644 (1993).
Leatherwood, J., et al., Interaction of Cdc2 and Cdc18 with a Fission yeast ORC2–Like Protein, Nature, 379:360 (1996).
Li, J.J. and Herskowitz, I, "Isolation of ORC6, a Component of the Yeast Origin Recognition Complex by a One–Hybrid System," Science, 262:1870–1874 (1993).
Liang, C., et al., "ORC and Cdc6P Interact and Determine the Frequency of Initiation of DNA Replication in the Genome," Cell 81:667–676 (1995).
Lisziewicz, J. et al., "Cloning and Characterization of the *Saccharomyces Cerevisiae* CDC 6 Gene," Nucleic Acids Research, 16:11507–11520 (1988).

(List continued on next page.)

*Primary Examiner*—David Saunders
*Assistant Examiner*—Mary Beth Tung
(74) *Attorney, Agent, or Firm*—Hamilton, Brook, Smith & Reynolds, P.C.

(57) ABSTRACT

The invention pertains to novel genes which function in the regulation of DNA replication and/or entry of a cell into mitosis. Tile invention also pertains to novel proteins encoded by the genes described herein, antibodies which bind the encoded protein, and homologs of the novel genes which function in regulation of DNA replication and/or entry of a cell into mitosis find hybridize to the DNA sequence of the novel genes. The invention also includes methods for determining the presence of a proliferative disorder comprising determining the presence of level of hscdc6.

12 Claims, 20 Drawing Sheets

OTHER PUBLICATIONS

Muzi–Falconi, M., et al., "cdc18+ Regulates Initiation of DNA Replication in *Schizosaccharomyces pombe.*," PNAS, 93:1566–1570 (1996).

Nishitani, H. and Nurse, P., "p65$^{cdc18}$ Plans a Major Role Controlling the Initiation of DNA Replication in Fission Yeast," Cell, 83:397–405 (1995).

Palmer, R.E., et al., "Mitotic Transmission of Artificial Chromosomes in cdc Mutants of the Yeast, *Saccharomyces cerevisiae*," Genetics, 125:763–774 (1990).

Piatti, S., et al., "Cdc6 is an Unstable Protein Whose do novo Synthesis in $G_1$ is Important for the Onset of S Phase and for Preventing a 'Reductional' Anaphase in the Budding Yeast *Saccharomyces cerevisiae*," EMBO, 1141:3788–3799 (1995).

Zhou, C., et al., "Molecular Cloning of *Saccharomyces cerevisiae* CDC Gene: Isolation, Identification and Sequence Analysis," J. Biol. Chem., 264:9022–9029 (1989).

Zwerschke, W., et al., "The *Saccharomyces cerevisiae* CDC6 Gene is Transcribed at Late Mitosis and Encodes a ATP/GTPase Controlling S Phase Initiation," J. Biol. Chem., 269:23351–23356 (1994).

Lee, C.C. and Caskey, C.T., "cDNA Cloning Using Degenerate Primers", In PCR Protocols: A Guide To Methods and Applications, Innis, M.A. et al., eds. (CA: Academic Press), pp. 46–53 (1990).

Donovan, S. and Diffley, J.F.X., "Replication origins in eukaroytes", Currant Opinion in Genetics & Development 6(2):203–207 (1996).

Basco, R.D. et al., "Negative Regulation of $G_1$ and $G_2$ by S–Phase Cyclins of *Saccharomyces cerevisiae*", Molecular and Cellular Biology 15(9):5030–5042 (1995).

Williams, R.S. and Stillman B., "Human and Xenopus Proteins Related to the Yeast CDC6/cdc18+ Regulators of DNA Replication", Journal of Investigative Medicine 44(3):198A (1996).

Williams, R.S. et al., "A Human Protein Related to Yeast Cdc6p", Proc. Natl. Acad. Sci. USA 94:142–147 (1997).

Coleman, T.R. et al., "The Xenopus Cdc6 Protein Is Essential for the Initiation of Single Round of DNA Replication in Cell–Free Extracts", Cell 87:53–63 (1996).

Marx, J., "How DNA Replication Originates", Science 270:1585–1587 (1995).

Yan, Z. et al., "Cdc6 is Regulated by E2F and is essential for DNA Replication in Mammalian Cells", Proc. Natl. Acad. Sci. USA 95, pp. 3603–3608, (1998).

Aparicio, O.M. et al., "Components and Dynamics of DNA Replication Complexes in *S. cerevisia*: Redistribution of MCM Proteins and Cdc45p during S phase", Cell 91:59–69 (1997).

Bell, S. P. and Stillman, B., "ATP–Dependent Recognition of Eukaryotic Origins of DNA Replication by a Multiprotein Complex", Nature 357:128–134 (1992).

Broek, D. et al., "Involvement of p34$^{cdc2}$ in Establishing the Dependency of S Phase on Mitosis," Nature 349:388–393 (1991).

Correa–Bordes, J. and Nurse, J., "p25$^{ruml}$ Orders S Phase and Mitosis by Acting as an Inhibitory of the p34$^{cdc2}$ Mitotic Kinase," Cell 83:1001–1009 (1995).

Coverley, D. et al., "Protein Kinase Inhibition in G2 Causes Mammalian Mcm Proteins to Reassociate with Chromatin and Restores Ability to Replicate," Exp. Cell Res. 238:63–69 (1998).

Dahmann, C. et al., "S–Phase–Promoting Cyclin–Dependent Kinases Prevent Re–Replication by Inhibiting the Transition of Replication Origins to a Pre–Replicative State," Curr. Biol. 5:1257–1269 (1995).

DeGregori, J. et al., "E2F–1 Accumulation Bypasses a G1 Arrest Resulting from the Inhibition of G1 Cyclin–Dependent Kinase Activity," Genes & Dev. 9:2873–2887 (1995).

Detweiler, C.S. and Li, J.J., "Ectopic Induction of Clb2 in Early G1 Phase is Sufficient to Block Prereplicative Complex Formation in *Saccharomyces Cerevisiae*," Proc. Natl. Acad. Sci. 95:2384–2389 (1998).

Diffley, J.F.X., "Two Steps in the Assembly of Complexes at Yeast Replication Origins in Vivo," Cell 78:303–316 (1994).

Donovan, S. et al., "Cdc6–Dependent Loading of Mcm Proteins onto Pre–Replicative Chromatin in Budding Yeast," Proc. Natl. Acad. Sci. 94:5611–5616 (1997).

Drury, L.S., "The Cdc4/34/53 Pathway Targets Cdc6p for Proteolysis in Budding Yeast," EMBO J. 16:5966–5976 (1997).

Duronio, R.J. and O'Farrell, P.H., "Developmental Control of the G1 to S Transition in Drosophila: Cyclin E is a Limiting Downstream Target of E2F," Genes & Dev. 9:1456–1468 (1995).

Duronio, R.J. et al., "E2F–Induced S Phase Requires Cyclin E." Genes & Dev. 10:2505–2513 (1996).

Dyson, N., "The Regulation of E2F by pRB–Family Members," Genes & Dev. 12:2245–2262 (1998).

Fujita, M. et al., "hCDC47, a Human Member of the MCM Family. Dissociation of the Nucleus–Bound Form During S–Phase," J. Biol. Chem. 271:4349–4354 (1996).

Hayles, J. et al., "Temporal Order of S Phase and Mitosis in Fission Yeast is Determined by the State of the p34$^{cdc2}$–Mitotic B Cyclin Complex," Cell 78:813–822 (1994).

Hengstschläger, M. et al., "Quality Control of Centrifugal Elutriation for Studies of Cell Cycle Regulation," BioTechniques 23:232–237 (1997).

Holthoff, H.P. et al., "A Novel Human Mcm Protein: Homology to the Yeast Replication Protein Mis5 and Chromosomal Location," Genomics 37:131–134 (1996).

Holthoff, H.P. et al., "Human Protein Mcm6 on HeLa Cell Chromatin," J. Biol. Chem. 273:7320–7325 (1998).

Hu, B. et al., "The P1 Family: A New Class of Nuclear Mammalian Proteins Related to the Yeast Mcm Replication Proteins," Nucl. Acids Res. 21:5289–5293 (1993).

Ishiai, M. et al., "Isolation of Human and Fission Yeast Homologues of the Budding Yeast Origin Recognition Complex Subunit ORC5: Human Homologue (ORC5L) Maps to 7q22," Genomics 46:294–298 (1997).

Jallepalli, P.V. et al., "Regulation of the Replication Initiator Protein p65$^{cdc18}$ by CDK Phosphorylation," Genes & Dev. 11:2767–2779 (1997).

Jallepalli, P.V. and Kelly, T.J., "Cyclin–Dependent Kinase and Initiation and Eukaryotic Origins: A Replication Switch?" Curr. Op. Cell. Biol. 9:358–363 (1997).

Kearsy, S.E. and Labib, K., "MCM Proteins: Evolution, Properties, and Role in DNA Replication," Bioch. Bioph. Acta 1398:113–136 (1998).

Krek, W. and DeCaprio, J.A., "Cell Synchronization," Meth. Enzymol. 254:114–124 (1995).

Krude, T. et al., "Human Replication Proteins hCdc21, hCdc46 and P1Mcm3 Bind Chromatin Univormly before S–Phase and are Displaced Locally during DNA Replication," J. Cell. Sci. 109:309–318 (1996).

Leone, G. et al., "E2F3 Activity is Regulated During the Cell Cycle and Is Required for the Induction of S Phase," Genes & Dev. 12:2120–2130 (1998).

Liang C. and Stillman, B., "Persistent Initiation of DNA Replication and Chromatin–Bound MCM Proteins During the Cell Cycle in cdc6 Mutants," Genes & Dev. 11:3375–3386 (1997).

Lukas, J. et al., "Cyclin E–Induced S Phase Without Activation of the pRb/E2F Pathway," Genes & Dev. 11:1479–1492 (1997).

McGarry, T.J. and Kirschner, M.W., "Geminin, an Inhibitor of DNA Replication, Is Degraded During Mitosis," Cell 93:1043–1053 (1998).

Moreno, S. and Nurse, P., "Regulation of Progression Through the G1 Phase of the Cell Cycle by the $rum1^{30}$ Gene," Nature 367:236–242 (1994).

Musahl, C. et al., "A Human Homologue of the Yeast Replication Protein Cdc21. Interactions with Other Mcm Proteins," Eur. J. Biochem. 230:1096–1101 (1995).

Nasmyth, K., "Control of S Phase in DNA Replication in Eukaryotic Cells," Cold Spring Harbor Laboratory Press (ed. M.L. DePamphilis), Cold Spring Harbor, NY (1996).

Newlon, C., "Putting It All Together: Building a Prereplicative Complex," Cell 91:717–720 (1997).

Innis, M. A., et al., "PCR Protocols," Academic Press, Inc., pp. 46–53 (1989).

De Mesmaeker, A., et al., "Antisense Oligonucleotides," Acc. Chem. Res. 28:366–374 (1995).

Sweeney, R.,et al., "Antisense in Abundance: The Ribosome as a Vehicle for Antisense RNA," Genetic Engineering 20:143–151 (1998).

Perkins, G. and Diffley, J.F.X., "Nucleotide–dependent Prereplicative Complex Assembly by Cdc6p, a Homolog of Eukaryotic and Prokaryotic Clamp–loaders," Molecular Cell 2:23–32 (1998).

Piatti, S., et al., "Activation of S–phase–promoting CDKs in late G1 Defines a "point of no return" After Which Cdc6 Synthesis Cannot Promote DNA Replication in Yeast," Genes & Dev. 10:1516–1531 (1996).

Quintana, D.G., et al., "Identification of a Novel Subunit of the Human Origin Recognition Complex with Homology to Yeast Orc4," J. Biol. Chem. 272:28247–28251 (1997).

Saha, P., et al., "Human CDC6/Cdc18 Associates with Orc1 and Cyclin–cdk and is Selectively Eliminated from the Nucleus at the Onset of S Phase," Mol. Cell. Biol. 18:2758–2767 (1998).

Sauer, K., et al., "Distinct Modes of Cyclin E/cdk2 Kinase Regulation and S–phase Control in Mitotic and Endoreduplication Cycles of *Drosophila Melanogaster*," Genes & Dev. 9:1327–1339 (1995).

Schulte, D., et al., "Expression, Phosphorylation and Nuclear Localization of the Human P1 Protein, a Homologue of the Yeast Mcm3 Replication Protein," J. Cell Sci. 108:1381–1389 (1995).

Stillman, B., "Cell Cycle Control of DNA Replication," Science 274:1659–1664 (1996).

Tanaka, T., et al., "Loading of an Mcm Protein onto DNA Replication Origins is Regulated by Cdc6p and CDKs," Cell 90:649–660 (1997).

Todorov, I.T., et al., "BM28, a Human Member of the MCM2–3–5 Family, is Displaced from Chromatin During DNA Replication," J. Cell Biol. 129:1433–1445 (1995).

Tugal, T., et al., "The Orc4p and Orc5p Subunits of the Xenopus and Human Origin Recognition Complex are Related to Orc1p and Cdc6p," J. Biol. Chem. 273(49):32421–32429 (1998).

Zou, L. and Stillman, B., "Formation of a Preinitiation Complex by S–phase Cyclin CDK–dependent Loading of Cdc45p onto Chromatin," Science 280:593–596 (1998).

Gura, T., "Antisense Has Growing Pains," Science 270:575–577 (1995).

"Antisense "97: A Roundtable on the State of the Industry," Nature Biotechnology 15:519–524 (1997).

Box 1

| | | | | | | | | | |
|---|---|---|---|---|---|---|---|---|---|
| Kl | orc1 | G | T | P | T | V | G | K | T (SEQ ID NO:28) |
| Sc | orc1 | G | T | P | G | V | G | K | T (SEQ ID NO:29) |
| Hs | orc1 | G | V | P | G | T | G | K | T (SEQ ID NO:30) |
| Sp | orc1 | G | T | P | G | T | G | K | T (SEQ ID NO:31) |
| Sc | cdc6 | G | P | P | G | T | G | K | T (SEQ ID NO:32) |
| Sp | cdc18 | G | A | P | G | T | G | K | T (SEQ ID NO:33) |

```
Forward Primer:  5'-   GGIGCCCCCGGIACCGGIAAAACC -3'         (SEQ ID NO:34)
                         C  A A       A    G  A
                         T    T       T       T
```

Box 3

| | | | | | | | | | |
|---|---|---|---|---|---|---|---|---|---|
| Kl | orc1 | V | V | L | L | D | E | L | D (SEQ ID NO:35) |
| Sc | orc1 | V | V | L | L | D | E | L | D (SEQ ID NO:36) |
| Hs | orc1 | V | L | L | V | D | E | L | D (SEQ ID NO:37) |
| Sp | orc1 | V | V | L | M | D | E | L | D (SEQ ID NO:38) |
| Sc | cdc6 | V | V | V | L | D | E | M | D (SEQ ID NO:39) |
| Sp | cdc18 | I | I | V | L | D | E | M | D (SEQ ID NO:40) |

```
Forward Primer:       5'-   ATCGTGCTCGACGAGATGG -3'          (SEQ ID NO:41)
                              G T  C   G T  A
                                   T
```

Box 4

| | | | | | | | | | |
|---|---|---|---|---|---|---|---|---|---|
| Kl | ocr1 | L | D | L | P | E | R | H | L (SEQ ID NO:42) |
| Sc | orc1 | M | D | L | P | E | R | H | L (SEQ ID NO:43) |
| Hs | orc1 | M | D | L | P | E | R | I | M (SEQ ID NO:44) |
| Sp | orc1 | M | D | L | P | E | R | I | L (SEQ ID NO:45) |
| Sc | cdc6 | L | D | M | K | D | R | F | L (SEQ ID NO:46) |
| Sp | cdc18 | L | D | M | T | D | R | F | L (SEQ ID NO:47) |

```
Reverse Primer:  5' -  AGAAAICGGTCIGTCATGTC -3'              (SEQ ID NO:48)
                           G    TA T   A
```

```
      10          20          30          40          50          60          70
123 456 789 012 345 678 901 234 567 890 123 456 789 012 345 678 901 234 567 890 123 456 789 012 345 gag cgc ggc tgg agt ttg ctg ctg ccg ctg agt tgc ttc agg ggc ttg tgg cgg tga gtc cga gag gct gcg        75 tgt gag aga cgt gag aag gat cct gca ctg agg agg tgg aaa gaa gag gat tgc tcg agg agg cct ggg gtc tgt   150 gag aca gcg gag ctg ggt gaa ggc tgc ggg ttc cgg cga ggc ctg agc tgt gct gtc gtc ATG CCT CAA ACC CGA   225
                                                                                Met Pro Gln Thr Arg TCC CAG GCA CAG GCT ACA ATC AGT TTT CCA AAA AGG AAG CTG TCT CGG GCA TTG AAC AAA GCT AAA AAC TCC AGT   300
Ser Gln Ala Gln Ala Thr Ile Ser Phe Pro Lys Arg Lys Leu Ser Arg Ala Leu Asn Lys Ala Lys Asn Ser Ser GAT GCC AAA CTA GAA CCA GTC CAA AAT GTC ACC ACT TGT GTA CCT CGT TCT CCT GTA AAA GCC CTG CCT CTC AGC CCC   375
Asp Ala Lys Leu Glu Pro Val Gln Asn Val Thr Thr Cys Val Pro Arg Ser Pro Val Lys Ala Leu Pro Leu Ser Pro AGG AAA CGT CTG GGC GAT GAC CTA TGC CTA AAC ACT CCC CAT ACA CCT CGT CCT TGT TCT CCA CCA AAG CAA GGC AAG   450
Arg Lys Arg Leu Gly Asp Asp Leu Cys Leu Asn Thr Pro His Thr Pro Arg Pro Cys Ser Pro Pro Lys Gln Gly Lys AAA GAG AAT GGT CCC CCT CAC TCA CAT ACA CTT AAG GGA CGA AGA TTG GTA TTT GAC AAT CAG CTG ACA ATT AAG       525
Lys Glu Asn Gly Pro Pro His Ser His Thr Leu Lys Gly Arg Arg Leu Val Phe Asp Asn Gln Leu Thr Ile Lys TCT CCT AGC AAA AGA GAA GAA GTT CAC GCC AAA ATA CTT TCT TCA GTT AGA AAA AGT CAA GAG ATC                   600
Ser Pro Ser Lys Arg Glu Glu Val His Ala Lys Ile Leu Ser Ser Val Arg Lys Ser Gln Glu Ile ACA ACA AAT TCT GAG CAG AGA TGT CCA AAG GAA TCT GCA CTA TTC AAG CAA GAA GGC ACT                           675
Thr Thr Asn Ser Glu Gln Arg Cys Pro Lys Glu Ser Ala Leu Phe Lys Gln Glu Gly Thr TGC TAC CAG CAA GCA AAG CTG GTC AAC ACA GTC CCA GAT CGG CCT GCC AGG GAA AGG GAG ATG GAT                   750
Cys Tyr Gln Gln Ala Lys Leu Val Asn Thr Val Pro Asp Arg Pro Ala Arg Glu Arg Glu Met Asp GTC ATC AGG AAT TTC TTG AGG GAA CAC ATC ATT TGT GGG GCT GGA AGC CTT TAC CTT TCT GGT GCT CCT GGA           825
Val Ile Arg Asn Phe Leu Arg Glu His Ile Ile Cys Gly Ala Gly Ser Leu Tyr Leu Ser Gly Ala Pro Gly ACT GGA AAA ACT GCC TGC TTA AGC CGG ATT CTG CAA GAC CTC AAG GAA CTG CTG AAA GGC TTT AAA ACT ATC ATG       900
Thr Gly Lys Thr Ala Cys Leu Ser Arg Ile Leu Gln Asp Leu Lys Glu Leu Leu Lys Gly Phe Lys Thr Ile Met
```

CTG AAT TGC ATG TCC TTG AGG ACT GCC CAG GCT GTA TTC CCA GCT ATT GCT CAG GAG ATT TGT CAG GAA GAG GTA      975
Leu Asn Cys Met Ser Leu Arg Thr Ala Gln Ala Val Phe Pro Ala Ile Ala Gln Glu Ile Cys Gln Glu Glu Val

TCC AGG CCA GCT GGG AAG GAC ATG ATG AGG AAA TTG GAA AAA CAT ATG ACT GCA GAG AAG GGC CCC ATG ATT GTG     1050
Ser Arg Pro Ala Gly Lys Asp Met Met Arg Lys Leu Glu Lys His Met Thr Ala Glu Lys Gly Pro Met Ile Val

TTG GTA TTG GAC GAG ATG CAA CTG GAC AGC AAA GGC CAG GAT GTA TTG TAC ACG CTA TTT GAA TGG CCA TGG         1125
Leu Val Leu Asp Glu Met Gln Leu Asp Ser Lys Gly Gln Asp Val Leu Tyr Thr Leu Phe Glu Trp Pro Trp

CTA AGC AAT TCT CAC TTG GTG CTG ATT GGT CTG AAC TTC CCA GAT CTC ACA GAT AGA ATT CTA CCT AGG CTT         1200
Leu Ser Asn Ser His Leu Val Leu Ile Gly Leu Asn Phe Pro Asp Leu Thr Asp Arg Ile Leu Pro Arg Leu

CAA GCT AGA GAA AAA TGT AAG CCA CAG CTG TTG GAC CAG GTT GCA AAT CAA TTC TGT GCC CGC AAA GTC             1275
Gln Ala Arg Glu Lys Cys Lys Pro Gln Leu Leu Asp Gln Val Ala Asn Gln Phe Cys Ala Arg Lys Val

CAA GAT CGA CTT AAT CAG GTA TCT AAT CAG GAT GTT CGC AAA GCA GAT GTT TGC GAT GTT ATT GAA GCT ATT GTA GAG TCA GAT GTC     1350
Gln Asp Arg Leu Asn Gln Val Ser Arg Asp Val Cys Asp Val Ala Leu Ala Ile Glu Val Glu Ser Asp Val

TCT GCT GTT TCA GGA GAT GTT CGC GAT GTT ATT GAA GCT ATT GTA GAG TCA GAT GTC     1425
Ser Ala Val Ser Gly Asp Val Arg Asp Val Ile Glu Ala Ile Val Glu Ser Asp Val

AAA AGC CAG ACT ATT CTC AAA CCA CTG TCT GAA TGT AAA TCA CCT CTG ATT CCC AAG AGG GTT GGT                 1500
Lys Ser Gln Thr Ile Leu Lys Pro Leu Ser Glu Cys Lys Ser Pro Leu Ile Pro Lys Arg Val Gly

CTT ATT CAC ATA TCC CAA GTC ATC TCA GAA GTT GAT GGT GAT AAC AGG ATG AGC CAA GAG GGA GCA CAA GAT         1575
Leu Ile His Ile Ser Gln Val Ile Ser Glu Val Asp Gly Asp Asn Arg Met Ser Gln Glu Gly Ala Gln Asp

TCC TTC CCT CTT CAG CAG CAG AAG ATC TTG GTT TCT TGC ATG TTT TTG CTC ATC AGG CAG TTG AAA ATC AAA GAG GTC    1650
Ser Phe Pro Leu Gln Gln Gln Lys Ile Leu Val Cys Ser Leu Met Leu Ile Arg Gln Leu Lys Ile Lys Glu Val

ACT CTG GGG AAG TTA TAT GAA GCC TAC AGT AAA GTC TGT CGC AAA CAG CAG GTG GCG GCT GTG GAC CAG GAG         1725
Thr Leu Gly Lys Leu Tyr Glu Ala Tyr Ser Lys Val Cys Arg Lys Gln Gln Val Ala Ala Val Asp Gln Glu
```

TGT TTG TCA CTT TCA GGG CTC TTG GAA AGG GCC ATT TTA GGA TTA AAG AGA AAC AAG GAA ACC CGT TTG ACA      1800
Cys Leu Ser Leu Ser Gly Leu Leu Glu Arg Ala Ile Leu Gly Leu Lys Arg Asn Lys Glu Thr Arg Leu Thr

AAG GTG TTT TTC AAG ATT GAA GAG AAA GAA ATA GAA CAT GCT CTG AAA AAG GAT AAA GCT TTA ATT GGA AAT ATC TTA  1875
Lys Val Phe Phe Lys Ile Glu Glu Lys Glu Ile Glu His Ala Leu Lys Lys Asp Lys Ala Leu Ile Gly Asn Ile Leu

GCT ACT GGA TTG CCT TAA att ctt ctc tta cac ccc acc cga aag tat tca gct ggc att tag aga gct aca gtc    1950
Ala Thr Gly Leu Pro (SEQ ID NO: 2)

ttc att tta gtg ctt tac aca ttc ggg cct gaa aac aaa tat gac ctt ttt tac ttg aag cca atg aat ttt aat    2025 cta tag att ctt taa tat tag cac aga ata tct ttg ggt ctt act att ttt acc cat aaa agt gac cag gta        2100 gac cct ttt taa tta cat tca cta ctt cca cta ctt gtg tat ctc tag cca atg tgc ttg caa gtg tac aga tct    2175 gtg tag agg aat gtg tgt ata ttt acc tct tcg ttt gct caa aca tga gtg ggt att ttt ttg ttt ttt           2250 gtt gtt gtt gag gcg cgt ctc acc ctg ttg ccc agg ctg gag tgc aat ggc gcg ttc tct gct cac tac           2325 agc acc cgc ttc cca ggt tga agt gat tct ctt gcc tca gcc tcc cga gta gct ggg att aca ggt gcc cac cac    2400 cgc gcc cag cta att ttt taa ttt tta gta gag aca ggg ttt cat gtt ggc cag gct ggt ctt gaa ctc ctg       2475 acc ctc aag tga tct gcc cac ctt ggc ctc cct aag tgc tgg gat tat agg cgt gag cca tgc tca gcc att       2550 aag gta ttt tgt taa gaa ctt taa gtt tag ggt aag aat gat cca gaa aaa tgc aag caa gtc cac               2625 atg gag att tgg agg aca ctg gtt aaa g
```

```
                         1                                                           50
Hscdc6      MPQTRSQAQA  TISFPKRKLS  RALNKAKNSS  DAKLEPTN.V  QTVTCSPRVK
Xcdc6       MPSTRSRSQS  SIQFPKKKTS  QTLAKEVSRA  KSKSEICS.S  VSLPLSPLPK
cdc 18      MCETPIGCHT  PRRCNRFIDS  AALIDCTNKT  NQREHSPSFS  IEIPTTPSRK
cdc6        ..........  ..........  ..........  ..........  ..........

51                                                          100
Hscdc6      ALPLS.....  PRKR....LG  DDNLCNTPHL  PPCSPP.KQG  KKENGPPHSH
Xcdc6       ELPLS.....  PRKR....LG  DDNRCNIPPT  LSCSPP.KQS  RKETGQP..T
cdc 18      RTLASSHFQT  PTKRIKYELG  ELQEEKTDLY  PNFPAQLKEN  KKPKLPTTPQ
cdc6        ..........  ..........  ..........  ..........  .MSAIPITP CSH Box
                       101                                                          150
Hscdc6      TLKGRRLVFD  NQLTIKSPSK  RELAKVHQNK  ILSSVRKSQE  ITTNSEQRCP
Xcdc6       TPKGRRLLFD  ENQAAAATPL  SPLKKLQDPY  LLSPVRKGQE  TPPSSRK...
cdc 18      TPKTPKRTIQ  IVTPKSLNRT  CNPVPFATRL  LQSTPHRQLF  PPTPSTPSTP
cdc6        TKRIRRNLFD  DAPATPPRPL  K.........  .....RKKLQ  FTDVTPESSP Box 1
                       151                                                          200
Hscdc6      LKKESACVRL  FKQEGTCYQQ  AKLVLNTAV.  PDRLPARERE  MDVIRNFLRE
Xcdc6       .QRNSVGVQL  FKQEGSCYQK  AKHALNTAI.  PERLLARESE  TAFIKTFLTS
cdc 18      ..........  .....SYNST  AKLSLRKSYR  SAGVVGRENE  KSIVESFFRQ
cdc 6       EKLQFGSQSI  FLRTKALLQK  SSELVNLNSS  DGALPARTAE  YEQVMNFLAK Box 1 - P loop
                       201                                                          250
Hscdc6      HICGKKAGSL  YLSGAPGTGK  TACLSRILQD  ..........  ..........
Xcdc6       HVSAGKAGSL  YISGAPGTGK  TACLNKLLQE  ..........  ..........
cdc 18      HLDANAGGAL  YVSGAPGTGK  TVLLHNVLDH  ..........  ..........
cdc6        AISEHRSDSL  YITGPPGTGK  TAQLDMIIRQ  KFQSLPLSLS  TPRSKDVLRH Box 2
                       251                                                          300
Hscdc6      ..........  ...LKKELKG  FKTIMLNCMS  LRTAQAVFPA  IAQEICQEEV
Xcdc6       ..........  ...TKDDLKQ  RKTVYINCMS  LRSSQAVFPA  IAEEISGGK.
cdc 18      ..........  ...VVSDYPK  VNVCYINCMT  INEPKAIFEK  IHSKIVKEEI
cdc6        TNPNLQNLSW  FELPDGRLES  VAVTSINCIS  LGEPSSIFQK  IFDSFQDLNG Box 3 - A loop
                       301                                                          351
Hscdc6      SRPAGKDM..  MRKLEKHMTA  EKGPM...IV  LVLDEMDQL.  .....DSKGQ
Xcdc6       SSLAAKDI..  VRSLEKLVTS  .KGPI...IL  LVLDEMDQL.  .....DSRGQ
cdc 18      LENEDHHINF  QCELESHFTQ  SANELYNPVI  IVLDEMDHL.  .....IAREQ
cdc6        PTLQIKNMQH  LQKFLEPYHK  KTT.....FV  VVLDEMDRLL  HANTSETQSV
```

Fig. 4A

```
                                                  Box 4                    Box 5
                 351                                                        400
   Hscdc6    DVLYTLFEWP WLSNSHLVLI GIANTEDLTD RILPRLQARE KCKPQLLNFP
   Xcdc6     DVLYTVFEWP WLTNSRMVLI GIANALDLTD RILPRLQARP RCRPQLLNFS
   cdc 18    QVLYTLFEWP SRPTSRLILV GIANALDMTD RFLPRLRTK. HITPKLLSFT
   cdc6      RTILELFLLA KLPTVSFVLI GMANSLDMKD RFLSRLNLDR GLLPQTIVFQ Box 5
             401                                                            450
   Hscdc6    PYTRNQIVTI LQDRLNQ... .......... ..........VSRD QV........
   Xcdc6     PYTKDQIATI LQDRLNT... .......... ..........VSGD QV........
   cdc 18    PYTAQEISTI IKARLKTAAT TSEKNNPFTP IKSISEVSDD SINVVSQHAD
   cdc6      PYTAEQMYEI VIQKMSSLPT I......... .......... ..........

Box 6
             451                                                            500
   Hscdc6    ....LDNAAV QFCARKVSAV SGDVRKALDV CRRAIEIVES DVK.......
   Xcdc6     ....LDNAAI QFCARKISAV SGDARKALDI CRRAVEIVEA DVR.......
   cdc 18    ETPFIHPAAI ELCARKVAAS SGDLRKALDI CRHAIELAER EWK.......
   cdc6      ...IFQPMAI KFAAKKCAGN TGDLRKLFDV LRGSIEIYEL EKRFLLSPTR CSH Box
             501                                                            550
   Hscdc6    ..SQTILKPL SECKSPSEPL ....IPKRVG LIHISQVISE VDGNRMTLSQ
   Xcdc6     ..GQTVLKPL TECASPCKEV PLNPVPKKVS LPHISRVLSD VYGDKMA.SR
   cdc 18    ..AQHD.NTL SSVDIP.... .......RAS IAHVVRATSA .....MSQSA
   cdc6      GSLNSAQVPL TPTTSPVKK. SYPEPQGKIG LNYIAKVFSK FVNNNSTRTR CSH Box
             551                                                            600
   Hscdc6    EGAQDSFPLQ QKILVCSLML LIRQLKIKEV TLGKLYEAYS KVC.RKQQVA
   Xcdc6     EGSSSESFPLQ QK........ .......... .......... ..........
   cdc 18    SARLKNLGLQ QKAILCTLVV ....CEKTSL SVADVFEKYS SLCLRDRLIY
   cdc6      IAK...LNIQ QKLILCTIIQ SLKL..NSDA TIDESFDHYI KAITKTDTLA
                                          CSH Box
             601                                                            650
   Hscdc6    AVDOSECLSL SGLLEARGIL GLK...RNKE TR..LTKVFF KIEEKEIEHA
   Xcdc6     .......... .......... .......... .......... ..........
   cdc 18    PLTSSEFCDV ANSLETLAII RLRTKQRNGK PQ..DRIISL LVPEMDVITA
   cdc6      PLQRNEFLEI CTILETCGLV SIKKTKCKGK TKRFVDKIDV DLDMREFYDE 651        666
   Hscdc6    LKDKALIGNI LATGLP*    (SEQ ID. NO.: 2)
   Xcdc6     .......... ......     (SEQ ID. NO.: 4)
   cdc 18    VGDIGTLKRF FDRR*.     (SEQ ID. NO.: 49)
   cdc6      MTKISILKPF LH*...     (SEQ ID. NO.: 50)
```

[ATG] CCA AGC ACC AGG TCT CGG TCT CAA AGC TCC ATT CAG TTT CCC AAG AAA ACT TCT CAG ACG CTC GCC AAA      75
 Met  Pro Ser Thr Arg Ser Arg Ser Gln Ser Ser Ile Gln Phe Pro Lys Lys Thr Ser Gln Thr Leu Ala Lys

GAG GTC TCA CGT GCA AAG AGC AAG TCT GAG ATC TCC TGC TCT CCG CTC CTT CCA CTT CCC AAA GAG             150
Glu Val Ser Arg Ala Lys Ser Lys Ser Glu Ile Ser Cys Ser Pro Leu Leu Pro Leu Pro Lys Glu

CTT CCC CTC AGT CCA CGC CTC CCA AAA CGG CTC GGT GAT GAC TGC AAT CGT CCT CCG ACA TTA AGC TGC TCC CCA 225
Leu Pro Leu Ser Pro Arg Leu Pro Lys Arg Leu Gly Asp Asp Cys Asn Arg Pro Pro Thr Leu Ser Cys Ser Pro

CCC AAG CAG TCT CGC AAA GAG ACT GGC CAG CCA ACC CCT AAG GGG CGC CGT TTA CTT TTT GAT GAG AAC CAG     300
Pro Lys Gln Ser Arg Lys Glu Thr Gly Gln Pro Thr Pro Lys Gly Arg Arg Leu Leu Phe Asp Glu Asn Gln

GCT GCA GCG ACA CCA CTA TCC CCC CTC AAG AAA AGG AAC AGT GTG GGG GTC CAG CTA TAT CTG TCC CCT GTG AAG GGG 375
Ala Ala Ala Thr Pro Leu Ser Pro Leu Lys Lys Arg Asn Ser Val Gly Val Gln Leu Tyr Leu Ser Pro Val Arg Lys Gly

CAA GAG ACC CCA AGC TCT CGT AAG CAA AGG AAC AGT GTG GGG GTC CAG CTA TTT AAA GAG GAG ACT GCA TTT     450
Gln Glu Thr Pro Ser Ser Arg Lys Gln Arg Asn Ser Val Gly Val Gln Leu Phe Lys Glu Glu Thr Ala Phe

TAT CAG AAG GCT AAG CAC AGT CAT TCT GCT TCT GCT TAC ATA TCT GGT GCT CCT GGA ACT                     525
Tyr Gln Lys Ala Lys His Ser His Ser Ala Ser Ala Tyr Ile Ser Gly Ala Pro Gly Thr

ATC AAG ACC TTC CTG ACA AGT TTG CAT GTT TCT GCT TCT GCT CTT TAC ATA TCT GGT GCT CCT GGA ACT         600
Ile Lys Thr Phe Leu Thr Ser Leu His Val Ser Ala Ser Ala Leu Tyr Ile Ser Gly Ala Pro Gly Thr

GGC AAA ACT GCG TGC TGC TTG AAT AAG CTG CTG CTG CAG GAG TTT CCG GCT ATA GCT CTC AAG GAA ATC         675
Gly Lys Thr Ala Cys Cys Leu Asn Lys Leu Leu Leu Gln Glu Phe Pro Ala Ile Ala Leu Lys Glu Ile

AAC TGC ATG TCA CGC TGC AGC AGT AGG AGT AGC CAG GCA GTG AAG TTG GAG AAG CTG ACT TCA AAG GGC AAA GTT TAC ATC 750
Asn Cys Met Ser Arg Cys Ser Ser Arg Ser Ser Gln Ala Val Phe Pro Ala Ile Glu Lys Leu Thr Val Tyr Ile

CTG GCC GCC AAA GAT ATT GTA AGG AGT GAG AAG TTG GAG AAG CTG GTG CTG ACT TCA AAG GGT CCA ATC ATC CTG GTG TTG 825
Leu Ala Ala Lys Asp Ile Val Arg Ser Glu Lys Leu Val Thr Ser Lys Gly Pro Ile Ile Leu Val Leu
```

GAT GAG ATG GAT CAG CTG GAC AGC AGA GGA CAG GAT GTC TTG TAC ACC GTG TTT GAG TGG CCT TGG CTT ACA AAT      900
Asp Glu Met Asp Gln Leu Asp Ser Arg Gly Gln Asp Val Leu Tyr Thr Val Phe Glu Trp Pro Trp Leu Thr Asn

TCT AGG ATG GTT TTA ATC GGC ATT GCT AAC GCA TTG GAT TTG ACA GAC CGT ATT TTG CCC AGG CTA CAA GCT CGA      975
Ser Arg Met Val Leu Ile Gly Ile Ala Asn Ala Leu Asp Leu Thr Asp Arg Ile Leu Pro Arg Leu Gln Ala Arg

CGT CCG TGC AGA CCA CAG TTG CTC AAC TTT TCT CCA TAT ACA AAG GAT GCT ACC ATT CTA CAG GAC AGA             1050
Arg Pro Cys Arg Pro Gln Leu Leu Asn Phe Ser Pro Tyr Thr Lys Asp Ala Thr Ile Leu Gln Asp Arg

CTA AAT ACG GTT TCA GGC GAT CAA GTT CTG GAT AAT GCT GCT ATT CAG TTC TGT GCA AGG AAA ATC TCT GCT GTC    1125
Leu Asn Thr Val Ser Gly Asp Gln Val Leu Asp Asn Ala Ala Ile Gln Phe Cys Ala Arg Lys Ile Ser Ala Val

TCT GGA GAT GCT CGA AAG GCG CTA GAT ATC TGC AGG AGA GCT GTT GAA ATT GTC GAA GCG GAT GTC AGG GGC CAG    1200
Ser Gly Asp Ala Arg Lys Ala Leu Asp Ile Cys Arg Arg Ala Val Glu Ile Val Glu Ala Asp Val Arg Gly Gln

ACT GTC CTT AAG CCT CTA ACT GAA TGT GCG TCT CCT TGT AAA GAA GTC CCA TTA AAC CCT GTT CCA AAA AAG GTC    1275
Thr Val Leu Lys Pro Leu Thr Glu Cys Ala Ser Pro Cys Lys Glu Val Pro Leu Asn Pro Val Pro Lys Lys Val

AGC CTT CCA CAC ATC TCT CGT GTC CTG TCG GAT GTG TAT GGG GAC AAG AGC CGT GAG GGT TCA AGC GAG            1350
Ser Leu Pro His Ile Ser Arg Val Leu Ser Asp Val Tyr Gly Asp Lys Met Ala Ser Arg Glu Gly Ser Glu

AGT TTT CCC TTA CAG CAG AAA (SEQ ID NO: 3)                                                              1371
Ser Phe Pro Leu Gln Gln Lys (SEQ ID NO: 4)
```

```
AAGCTTCCAT TGTGTGGTAA CTTTCTCCAT TCATGGCAGC CCATTCTCTT CACTTTTGTA    60
GTTTTCAGCT GCTAAAAAGC CTTCACGAAA TGTACTCCAC CATCTCTTCC TGTTTAGAAC   120
CTGAATCTGT CTAATCATCC CCCTATGATA AAGTGGTCAA GAATTTGATT TTCTGTCAGA   180
TTCAGATTCA AATTCTAGCT CTTCCACTTA CTATTGTGTG ACCTTGGGCA ATTACTCAAC   240
TCCCCTCTAC TGTAGTTCCC TCATTTGTAA AGTGAAATAA CACCAGGTTC ATGGGGTGC    300
TTGTGAAATT AATAAGGTGA TGTATGTAAA ATACTGAGCA CAGCCCCTGG CATACACTTA   360
AGCACTCAAT ATTGGCTCTC TTCATGAACT AGGTACCAAT TCACTGGATG ATCGTAATAT   420
TGTTGCTTCC CTCTTTCTAG GCTTTATGGC TCTATTTTGT TTGTTACTGA GGGGTAAAAG   480
ATAAATGTTT ACCATCACCT AAAATTGGGT TCTGGCCCTA AAGGAACCTG AGGCTTAGAT   540
GAATTATTGG CTTTGGAAGC TGGCCTTCAA ATTACTGCGC TAATTTATAT TTTTCATTAA   600
AACTCAGCTT GCCTCTTCTA TATAGCTGTC TTCCCTGGCC CTGAAACCCT AGTGTTTCGC   660
CATAAAAGAT TTTAAAATTA AGGGGTCATA ATTCCCTCCC CATGATGTGT GGATTAATGG   720
TAAGAAGATG CCAGAACATA ATATTCTTAG GTTGAACGAA ATAAAAGTAA AGAGTTGGCT   780
CTGTTTCTCA CCTTTGAAGC ACAAATCAAG AGATACTATG ATGAAGCATA GTTTTCTTT    840
ATATAGGTGT GTAGAACTTT ACCATAAAAA TCACTAGTTC AGCCATCAGG AGATCTGGAT   900
CCTAGGCTCT TCACTGTCAC CAAGATGCTG TGACCTCTAA CCTTGTATAG AAGTTT       956
(SEQ ID NO:5) 200N

TGGGTTCTGG CCCTAAAGGA ACCTGAGGCT TAGATGAATT ATTGGCTTTG GAAGCTGGCC    60
TTCAAATTAC TGCGCTAATT TATATTTTTC ATTAAAACTC AGCTTGCCTC TTCTATATAG   120
CTGTCTTCCC TGGCCCTGAA ACCCTAGTGT TTCGCCATAA AAGATTTAA AATTAAGGGG    180
TCATAATTCC CTCCCCATGA TGTGTGGATT AATGGTAAGA AGATGCCAGA ACATAATATT   240
CTTAGGTTGA ACGAAATAAA AGTAAAGAGT TGGCTCTGTT CTCACCTTT GAAGCACAAA    300
TCAAGAGATA CTATGATGAA GCATAGTTTT CTTTATATA GGTGTGTAGA ACTTTACCAT    360
AAAAATCACT AGTTCAGCCA TCAGGAGATC TGGATCCTAG GCTCTTCACT GTCACCAAGA   420
TGCTGTGACC TCTAACCTTG TATAGAAGTT TGCTTTGTAC TTTGCGAGGT TGAGCATTAG   480
AGAGGTAAGG AAAGTGCCTA GCATCATACC TGGCGCACAG AACCCAAAAC GGTAGGTATC   540
ATGTAGCAGT TCTGAAAATC TAGCCCATCA GGATGATGCA AATGGGTACT TTAGGCAGTG   600
AGAAGGGGAA CCACATCTTG ACACTTCCAG TCGAAGGAAG AGTGCGACTG CGCGGCAGCA   660
AAGACTACGC CTCCCAGCGT GCTTTGCGGC GGGCCGGCCC GCTTACCCA GAGTCGCCCT    720
GCCGCAATCG CGGGTTTTTT CCACCGAGGC CCCGGATGTA GATTCCCTTC CCCCGTTCAG   780
TGGTGGTGGC CTCACAGCGA CTCTAAGACT TGGGGCTCTC TCATTGGCTG TAACTCTTCC   840
ACTGGATTGG TAGCAAAAAA AGAGGCGGTG CCCAAGGCGA AAGGCTCTGT GACTACAGCC   900
AATCAGAATC GAGGCCGGGC TTTGGCGGGA GGTGGGAACG CTGTGGCCAT TCGGATTTGG   960
CGC    (SEQ ID NO: 6)                                               963 cDNA

GAGCGCGGCT GGAGTTTGCT GCTGCCGCTG TGCAGTTTGT TCAGGGGCTT GTGGCGGTGA    60
GTCCGAGAGG CTGCGTGTGA GAGACGTGAG AAGGATCCTG CACTGAGGAG GTGGAAAGAA   120
GAGGATTGCT CGAGGAGGCC TGGGGTCTGT GAGACAGCGG AGCTGGGTGA AGGCTGCGGG   180
TTCCGGCGAG GCCTGA (SEQ ID NO: 7)                                    196
```

FIG. 8A intron F107 about 1.5 kb, have 335 bp of 5' end

```
AGGGAAAAGA GCTGAGCTCG CTGGAGGTCT GAGGTCGGGA TCAGGGAAAG GGCAGGTGCC    60
CTCGGGGTAG TTCTAGCAGT TATGCGTGGT GTGAAGGAGG TGAAAGTTGT AGGAAGGAAA   120
TATTCTGGGG TGCGTTGAGA GCTGCCTAGA AGGAGGACTG AGTGCAGGGG CGGAAAGAAC   180
TGAGGGAAGA CTGAGCTGCA GTGTGAGGGC TTGGGATAGA AGAGACTAAA TGTGGCGGGT   240
GCTGGGCTGA ACTGGTGATA AGACACCCC GCGTGCCTGG AGGGAGGAAA CTAGAAGTTC    300
TATATAAATC AATTCATGTA ACTTTTTTTT TTTTT (SEQ ID NO: 8)                335
```

Start codon
```
GCTGTGCTGT CGTC[ATG]CCT CAAACCCGAT CCCAGGCACA GGCTACAATC AGTTTTCCAA   60
AAAGGAAGCT GTCTCGGGCA TTGAACAAAG CTAAAAACTC CAGTGATGCC AAACTAGAAC   120
CAACAAATGT CCAAACCGTA ACCTGTTCTC CTCGTGTAAA AGCCCTGCCT CTCAGCCCCA   180
GGAAACGTCT GGG (SEQ ID NO: 9)                                      193
``` intron f324 -r534, <400 bp (have 128bp of 5' seq)

```
TAAACCATCC ATTATATCAC TTTTTCACTA GCAGCTCGTG ACCTTTCTTT TCTTGGTAAG    60
ATGTGTGTCC TTTGAAGGAG CTTTCTAAGT TCAGTTAAGA CTTCTTTTTT TTTTTTTTT   120
TTTTTTGG (SEQ ID NO: 10)                                           128
```

```
CGATGACAAC CTATGCAACA CTCCCCATTT ACCTCCTTGT TCTCCACCAA AGCAAGGCAA    60
GAAAGAGAAT GGTCCCCCTC ACTCACATAC ACTTAAGGGA CGAAGATTGG T           111
```

Intron R534 a bout 1.6 kb, have 1209 bp of 3' end

```
...GGGGCCCCCC CCCAAACCTG GGTAAATTTT TTTTTTTTTT TTTTTGGATT TTTAGTTGAG    60
ACAGGGTTTT GCCATATTGG CCAATCTGGT CTCTGAACTC CTGACCTCAG GTGATCCAAC   120
TGCCTCGGCC TCCCAAAGTG CTGGGATTAT AGGCATGAGC TACCGCTCCT GGCCTAAGAC   180
TACTCTTCAT TTTAGTTATT TTCAGAATGG TTGCTAAGTG CTTACCGAAC TCCAGAGTTA   240
GACACTTACT GAGGTCACTC TGAACTACTT AATAAGTCTG ATCTTCAATT CCTTAATACT   300
GAACTTAGTT CTGTCAATGT TTTAAGTTAC CTTGTAGTTA CATGGTATTA TGAAACTTAC   360
CTCAATATTT GTGAAATTAA AAGAAACAAA AACGTGACAT GATGAATATT TTCCATCCTT   420
TAGGACAGTG ATTGGTAATT CTTTCGATGG TTTGGAACAT TTATTTTTAA ATGGGGGGTA   480
ATTTGGTTGT TTCTGGAGAC ATTTTTGGTT GTTACAGCTG GGGGTTGCTA CTGGCATAGT   540
GGGTAGAGGC CAGGGATGCT GCTAGACATT ACAATGCACA GGACAGCTCC TTTGACAATG   600
AAGAATTATT TGGTCCAAGA TGTCAGTGGT GCCAAGGTTG AGAAAACCTG TTTCAAAATA   660
GCCTTACAAT TTCATCCTAC TAAAACCCAT TTGGTTTCTA CTAAATGCAG TAGTCCCCAC   720
TTATCCATGG GGGATACATT CCAAGACCCC CAGTGGACGC CTGCAATCGA GGACAGTACC   780
AAACCCTACA TATACTGTGT TTTTGATTTG ATAACCAAGT CAGCTACTAA GTGACTAGTG   840
GGTGGATAGC ATATACAGTG TGGATATGCT GGCTGAAGGG ATGATTCATG TCTTGGGTAG   900
GATGGTGCGG GATTTCATCA TGGCACTCCA CAGCATGCAA TTTAAAACTT GTCAATTGTT   960
TATTTCTGGA ATTTTCCATT TAGTATTTTC AGACTGAGGG TAACTAGAAC GGTGGATGAA  1020
GGGACTACTG TAGTAAGATC AGTGGTGCCA TCTGGTGACC AATATTTGCT GCTAAGTGAG  1080
AAGGCATTTT ATTTTGGTGG TTCTGACTAA GGTAGAAATT CACCTCTTTC TGGAAGAGGC  1140
AGAGGTCTTG CACATCCTTT TACTATCCAA TGCTATGAGT GACTACATTT TTATTTTATT  1200
GTGTTTCAGG (SEQ ID NO: 12)                                        1210
```

FIG. 8B

```
ATTTGACAAT CAGCTGACAA TTAAGTCTCC TAGCAAAAGA GAACTAGCCA AAGTTCACCA    60
AAACAAAATA CTTTCTTCAG TTAGAAAAAG TCAAGAGATC ACAACAAATT CTGAGCAGAG   120
ATGTCCACTG AAGAAAGAAT CTGCATGTGT GAGACTATTC AAGCAAGA (SEQ ID NO: 13)168

(intron 641F-846R) (or 482F-695R), (129 bp)

AGGTTTGTTC TTACATGGCA ACTGTTAGTG CAGCCATTGT AACCAAGGCT GATGACTCCA    60
AATGAAACCA CCCACTGGGT CTTCTCATTC ACCTTCTGTT GTGTCTAATT GACCTTTTAT   120
GTCTGGCAC (SEQ ID NO: 14)                                          129

AGGCACTTGC TACCAGCAAG CAAAGCTGGT CCTGAACACA GCTGTCCCAG ATCGGCTGCC    60
TGCCAGGGAA AGGGAGATGG ATGTCATCAG GAATTTCTTG AGGGAACACA TCTGTGGGAA   120
AAAAGCTGGA AGCCTTTACC TTTCTGGTGC TCCTGGAACT GGAAAAACTG CCTGCTTAAG   180
CCGGATTCTG CAAGACCTCA AG (SEQ ID NO: 15)                           202

(intron 779-973)
```

Fig. 8C

```
GTACATTGAG AGTCTGAATT ATGATACTCT TGGTAAAATG ATACTTGGGT GTTTTTGTTT      60
GTTTGTTTGT TTTGTTTTGT TTTGTTTTGT TTTTTGAGAC                          100
``` about 1.5 kb

```
TTTCAAANAA AAAAAAAGA AAGAAAGAAA AGAAAGAGTA GAAGTTTAGA AGATTGAGGG     160
TTTCTTCAAA ATAAAACATT TGTAATTTCA TTGTTTAAAT CTTTCCAAAT GAAAGTAGAG    220
CTTCCTTACG TGCTGTTAGC TCTTCAAAGA CATTTTAGGC TCTATCAGAT CTTTATTTTC    280
TGAGGCCAAA ATAACTCCCA TATTTGCATT TTTTTTTCCA G (SEQ ID NO: 16)        321
```

```
AAGGAACTGA AAGGCTTTAA AACTATCATG CTGAATTGCA TGTCCTTGAG GACTGCCCAG     60
GCTGTATTCC CAGCTATTGC TCAGGAGATT TGTCAGGAAG AGGTATCCAG GCCAGCTGGG    120
AAGGACATGA TGAGGAAATT GGAAAAACAT ATGACTGCAG AGAAGGGCCC CATGAT        176
(SEQ ID NO: 17)
``` intron 898-1089 (320 bp)

```
GTAAGTATTG TTCTGGCTTC CATGTTGCTC TGTGAAAATC TGCAAGGTCT GTTGCCCATA     60
AAAAGTACAT TTTGTATATT TTCTCTCTGA AGGATAGTTA CATAAACTTA AAGGGAAAGA    120
AGAGAAGGAA GATACACCTA ATTTTAAATT GGATTACTTA TAGATGATGT GGGGTATCCT    180
TGTAGCAGTA ACTAGAGATA GGTTAGATTA TGATCTTTAA ACTGGTCTCA GCTTTAGGAA    240
AGTGACCTGA AGTCAGCCTA TATCAAACAT TAGAGGGTTA AGAAGGTGAA TATGGATACT    300
AACTGTTTCT CTTTTTATAG (SEQ ID NO: 18)                                320
```

```
TGTGTTGGTA TTGGACGAGA TGGATCAACT GGACAGCAAA GGCCAGGATG TATTGTACAC     60
GCTATTTGAA TGGCCATGGC TAAGCAATTC TCACTTGGTG CTGATTGGT (SEQ ID NO: 19)109
``` intron 1051-1253, (307 bp)

```
TAGTGCTCAA TTGTTAATGT TACATGGTGG TTCTAAAGTA TTTTTTAAGA ATATATATTC     60
AGCTTATTTA TCAGCTATTT TATCTTAAAC CAGCTTTCTG CCGTGTCAAA ATAAGAAAGT    120
TAAATGACTA TGTACATCTT ACCTAATAGA TACATCTTAT CTATTGGGAT GGGGTAGGAG    180
ACAAGTGGCA AGCAACAATT AGAATGCTAG ATTCTATAAC TGGAGATTTA TTTAGCTTTC    240
AGAAGATTTA GTTTTCCCTT TAGGATAATT TGACCAATGA TCAATGTTGT TGATCTCCTC    300
CTTAGGT (SEQ ID NO: 20)                                              307
```

FIG. 8D

```
ATTGCTAATA CCCTGGATCT CACAGATAGA ATTCTACCTA GGCTTCAAGC TAGAGAAAAA    60
TGTAAGCCAC AGCTGTTGAA CTTCCCACCT TATACCAGAA ATCAGATAGT CACTATTTTG   120
CAAGATCGAC TTAATCAGGT ATCTAGAGAT CAGGTTCTGG ACAATGCTGC AGTTCAATTC   180
TGTGCCCGCA AGTCTCTGC TGTTTCAGGA GATGTTCGCA AAGCACTGGA TGTTTGCAGG    240
AGAGCTATTG AAATTGTAGA GTCAGATGTC AAAAGCCAGA CTATTCTCAA ACCACTGTCT   300
GAATGTAAAT CACCTTCTGA GCCTCTGATT CCCAAGAGGG TTGGTCTTAT TCACATATCC   360
CAAGTCATCT CAGAAGTTGA TGGTAACAGG ATGACCTTGA GCCAAGAGGG AGCACAAGAT   420
TCCTTCCCTC TTCAGCAGAA GATCTTGGTT TGCTCTTTGA TGCTCTTGAT CAGGCAGTTG   480
AAAATCAAAG AGGTCACTCT GGGGAAG (SEQ ID NO: 21)                      507
``` intron 1530F-1730R (435 bp)

```
GTAAGTTGGG ATGGAGCAGA TGGAACGGAG GTAGAGATCA GAATCTGCTT TGCAGAGCAG    60
GTATTTTCCA AAAGGCCTAT GATACTTCAG CTGATAATAA ATTTAAAATG GATTTTAACA   120
GTAAGAATTA ATACTGGTAC TATATAAAAG GCACCTATTT CCCTTGGATT GTGGTTGAGA   180
GTTTATCATT AATCCTTTCC CTATCCTCCC CTTCATTTCT GCATCTCTCT AGGAAATATA   240
TAAAGCCCCT TTCCTACATT ACTGTATAGG TTTTCGGGAA TATCTACAGA AGCCTGTTCA   300
AAGATTTTAT TGAAAAGAGG AAGAAATAGG GTATTCAGAT AAGTTTTTGC AAACCCAGAC   360
TCAGGTTTCT TAAATGATTA AAGGCTATAA GCAATGTGAC TTTTAAGCAG CGTTTGTTCT   420
CCCTTGTTTC CTACCAG (SEQ ID NO: 22)                                 437
```

```
TTATATGAAG CCTACAGTAA AGTCTGTCGC AAACAGCAGG TGGCGGCTGT GGACCAGTCA    60
GAGTGTTTGT CACTTTCAGG GCTCTTGGAA GCCAGGGGCA TTTTAGGATT AAAGAGAAAC   120
AAGGAAACCC GTTTGACAAA GGT                                          143
``` intron 1683F-1921R (299 bp)

```
ACAACTGCTT TTTTGTGACA GTGTTTTTAA TTGTCCTATT TTGTAGAGTG ATGCTAAAGT    60
AAAGGTTTAT TGTTAAACAA GATGACCACA GTTAGTTAAA CAAGTCGTTT TTTGTTAGGT   120
AAGGTTTAAG GTGTGTAAAG ATGGGAGTGT GATATGAATA TTTTTTCAAG CCATTGGAAA   180
AAAAAGTGTT TAACTTGCTT GCCTTTTGTG AGAAAAAGTT TAATATGGTA GAAGTTTGTA   240
TACTGACAAC TTTGCTTTTG TGAGTTCCCC AGTGTGAAAA ATCCTTTTCT CTTCTTTCC    299
```

FIG. 8E

```
GTTTTTCAAG ATTGAAGAGA AAGAAATAGA ACATGCTCTG AAAGATAAAG CTTTAATTGG      60
                                  Stop codon
AAATATCTTA GCTACTGGAT TGCCT[TAA]AT TCTTCTCTTA CACCCCACCC GAAAGTATTC    120
AGCTGGCATT TAGAGAGCTA CAGTCTTCAT TTTAGTGCTT TACACATTCG GGCCTGAAAA      180
CAAATATGAC CTTTTTTACT TGAAGCCAAT GAATTTTAAT CTATAGATTC TTTAATATTA      240
GCACAGAATA ATATCTTTGG GTCTTACTAT TTTTACCCAT AAAAGTGACC AGGTAGACCC      300
TTTTTAATTA CATTCACTAC TTCTACCACT TGTGTATCTC TAGCCAATGT GCTTGCAAGT      360
GTACAGATCT GTGTAGAGGA ATGTGTGTAT ATTTACCTCT TCGTTTGCTC AAACATGAGT      420
GGGTATTTTT TTGTATGTTT TTTTTGTTGT TGTTGTTTTT GAGGCGCGTC TCACCCTGTT      480
GCCCAGGCTG GAGTGCAATG GCGCGTTCTC TGCTCACTAC AGCACCCGCT TCCCAGGTTG      540
AAGTGATTCT CTTGCCTCAG CCTCCCGAGT AGCTGGGATT ACAGGTGCCC ACCACCGCGC      600
CCAGCTAATT TTTTAATTTT TAGTAGAGAC AGGGTTTTAC CATGTTGGCC AGGCTGGTCT      660
TGAACTCCTG ACCCTCAAGT GATCTGCCCA CCTTGGCCTC CCTAAGTGCT GGGATTATAG      720
GCGTGAGCCA CCATGCTCAG CCATTAAGGT ATTTTGTTAA GAACTTTAAG TTTAGGGTAA      780
GAAGAATGAA AATGATCCAG AAAAATGCAA GCAAGTCCAC ATGGAGATTT GGAGGACACT      840
GGTTAAAGAA TTC (SEQ ID NO: 25)                                         853

CAGAAAAATG CAAGCAAGTC CACATGGAGA TTTGGAGGAC ACTGGTTAAA GAATTCTATT       60
TCTTTGTATA CGTATACTAT GTTCATGGTG CAGATACTAC AACATTGTGG CATTTTAGAC      120
TCGTTGAGTT TCTTGGGCAC TCCCAAGGGC GTTGGGGTCA TAAGGAGACT ATAACTCTAC      180
AGATTGTGAA TATATTTATT TTCAAGTTGC ATTCTTGTC TTTTTAAGCA ATCAGATTTC       240
AAGAGAGCTC AAGCTTTCAG AAGTCAATGT GAAAATTCCT TCCTAGGCTG TCCCACAGTC      300
TTTGCTGCCC TTAGATGAAG CCACTTGTTT CAAGATGACT ACTTTGGGGT TGGGTTTTCA      360
TCTAAACACA TTTTTCCAGT CTTATTAGAT AAATTAGTCC ATATGGTTGG TTAATCAAGA      420
GCCTTCTGGG TTTGGTTTGG TGGCATTAAA TGG (SEQ ID NO: 26)                   453
```

FIG. 8F

METHODS OF IMMUNOASSAY FOR HUMAN CDC6

RELATED APPLICATIONS

This application is a continuation-in-part of and claims priority to International PCT Application No. PCT/US97/07333, filed on May 2, 1997, which is a continuation-in-part in-part application, U.S. Ser. No. 08/648,650, filed May 15, 1996, now U.S. Pat. No. 6,074,819 which is a continuation-in-part application of U.S. Ser. No. 08/643,034, filed May 2, 1996, now U.S. Pat. No. 5,851,821 the teachings of which are incorporated herein by reference in their entirety.

GOVERNMENT SUPPORT

The invention was supported, in whole or in part, by grants R01AR40849, RO1-HL54794, P50-HL55988 and PO1-HL06296 from the National Institutes of Health, and PO1-CA-13106 from the National Cancer Institute. The Government has certain rights in the invention.

BACKGROUND OF THE INVENTION

Proliferative growth of normal cells requires an orderly progression through a series of distinct steps, a process known as the cell cycle (Alberts et al., *Cell Growth and Division*, Garland Publishing, Inc., New York). Progression through the cell cycle is modulated by nutrient availability, cell size, and growth factors through complex signaling pathways involving phosphorylation cascades and the strictly regulated expression and stability of specific proteins required at each phase of the cell cycle. In addition, the sequence of cell cycle events is rigorously controlled at specific checkpoints to ensure that each discrete stage in the cell cycle has been completed before the next is initiated. Human diseases associated with abnormal cell proliferation result when these rigorous controls on cell cycle progression are perturbed.

SUMMARY OF THE INVENTION

The invention relates to novel genes which function in cell cycle regulation. In a particular embodiment, the genes are derived from vertebrates, including mammalian cells, particularly those derived from Xenopus or human cells, and function in the regulation of DNA replication and/or entry of a cell into mitosis. In one embodiment, the gene is a human gene called Hscdc6 and in another embodiment the gene is a Xenopus gene called Xcdc6. In one embodiment, the genes have a DNA sequence comprising at least one DNA sequence selected from the group consisting of SEQ ID NOs: 1, 3, 5, 6, 7, 8, 9, 10, 11, 12, 13, 14, 15, 16, 17, 18, 19, 20, 21, 22, 23, 24, 25, 26, and combinations thereof; the invention also pertains to the complementary DNA sequences thereof. The present invention also relates to genes which function in the regulation of DNA replication or the entry of a cell into mitosis and which have a nucleotide sequence which hybridizes under conditions of medium stringency to at least one DNA sequence selected from the group consisting of SEQ ID NO: 1, 2, 3, 4, 5, 6, 7, 8, 9, 10, 11, 12, 13, 14, 15, 16, 17, 18, 19, 20, 21, 22, 23, 24, 25 and 26.

In particular embodiments, the isolated nucleic acid molecule encodes a protein or polypeptide with the same amino acid sequence as the endogenous protein or polypeptide. In another embodiment, the isolated nucleic acid molecule has the same nucleotide sequence as the endogenous gene encoding the protein or polypeptide.

Accordingly, this invention pertains to an isolated Hscdc6 gene or an Xcdc6 gene, or an active derivative or fragment thereof. The isolated gene is characterized by its ability to regulate the cell cycle as described herein. In particular embodiments, the expressed protein or polypeptide is purified to homogeneity or is substantially free of other proteins (i.e., isolated).

The invention also pertains to novel gene products, e.g., polypeptides or proteins, encoded by the vertebrate genics described herein, or an active derivative or fragment thereof. In a particular embodiment, the polypeptide or protein has the amino acid sequence of SEQ ID NO: 2 or SEQ ID NO: 4. In another embodiment, the gene product is a recombinant human or Xenopus polypeptide or protein which regulates DNA replication and/or the entry of a cell into mitosis. In one embodiment, the encoded protein or polypeptide is a fragment having DNA replication regulation and/or mitosis regulation activity. In another embodiment, the encoded protein or polypeptide is a derivative possessing substantial sequence identity with the endogenous protein or polypeptide.

The invention also relates to DNA constructs comprising the nucleic acid molecules described above operatively linked to a regulatory sequence, and to recombinant host cells, such as bacterial cells, fungal cells, plant cells, insect cells and mammalian cells, comprising the nucleic acid molecules described above operatively linked to a regulatory sequence.

The invention also pertains to an antibody, or an antigen-binding fragment thereof, which selectively binds to the described protein or polypeptide, or an active derivative or fragment thereof. One embodiment of the invention relates to monoclonal antibodies having specificity for Hscdc6. In particular, the invention encompasses the hCdc6-26, hCdc6-37, hCdc6-34, hCdc6-39, and hCdc6-41 monoclonal antibodies or an immunoglobulin antigen binding region or fragment derived from the hCdc6-26, hCdc6-37, hCdc6-34, hCdc6-39, and hCdc6-41 monoclonal antibodies.

Another embodiment of the claimed invention relates to the monoclonal antibodies derived from the hybridoma deposited with the American Type Culture Collection (ATCC), Accession Numbers: HB-12590 and HB-12591 Oct. 30, 1998, as well as to the deposited hybridomas themselves. Additionally, the invention relates to a humanized or chimeric immunoglobulin having specificity for Hscdc6 comprising an antigen binding region of non-human origin (e.g., the complementarity determining region (CDR) that is derived from the hCdc6-26, hCdc6-37, hCdc6-34, hCdc6-39, or hCdc6-41 monoclonal antibody). The humanized or chimeric immunoglobulin can further comprise at least a portion of human origin (e.g. a human constant region and/or a human framework region (FR)).

The invention also relates to a method for assaying the presence of the described protein or polypeptide in a cell, e.g., in a sample from an individual, comprising contacting said cell with an antibody which specifically binds to the protein or polypeptide. Embodiments of the claimed invention include Enzyme-Linked Immnosorbent Assay (ELISA), competition ELISA assays, RadioImmuno-Assays (RIA), immunofluorescence and immunohistochemical assays which involve assaying Hscdc6 in a sample using the monoclonal antibodies having specificity for Hscdc6, as described herein. The invention involves determining the presence or absence of Hscdc6 comprising combining the sample to be tested with an antibody (e.g., hCdc6-26, hCdc6-37, hCdc6-34, hCdc6-39, or hCdc6-4 1) having specificity for Hscdc6, and then detecting or measuring the formation of the complex between the antibody and the antigen. The antibodies are detectably labeled (e.g., radioactive, fluorescently, biotinylated or HRP-conjugated) to facilitate detection of the complex.

The claimed invention also pertains to methods for determining the presence or absence of a proliferative disorder (e.g., cancer) comprising determining the presence, absence, or the level of hscdc6, wherein the presence of hscdc6 or an elevated level of hscdc6, as compared to a control, standard, or baseline, indicates the presence of a proliferative disorder. An embodiment of the claimed invention includes determining the presence or absence of a proliferative disorder comprising determining the levels (e.g., presence or absence) of two or more markers for proliferative disease, wherein one of the markers is hscdc6. The additional marker can be a protein from the Mcm (mini-chromosome maintenance) family (e.g., Mcm-2, Mcm-3, Mcm-4, Mcm-5, Mcm-6, and Mcm-7). The invention also embodies methods for diagnosing or aiding in the diagnosis of a proliferative disease comprising determining the presence, absence or level of hscdc6, wherein the presence of hscdc6 or ail elevated level of hscdc6, as compared to a control, standard, or baseline, indicates a positive diagnosis for a proliferative disorder. These methods utilize the hscdc6 assays and/or monoclonal antibodies having specificity for hscdc6, as described herein.

Furthermore, the invention encompasses pharmaceutical compositions comprising the genes and proteins or polypeptides described herein, as well as methods of treating disease utilizing the compositions described herein. For example, the invention relates to a method of treating a tumor in an individual. In the method, an antagonist of Hscdc6 is administered to the individual, causing at least one of two possible results: inhibition of Hscdc6 function and inhibition of tumor cell DNA replication, with concomitant inhibition of tumor growth, or mitotic division of tumor cells with failure of DNA replication and tumor cell death. Such compositions comprise antibodies having a specificity for hscdc6(e.g,. hCdc6-26, hCdc6-37, hCdc6-39, hCdc6-34, and hCdc6-41).

The invention also relates to a method of treating a tumor in an individual comprising administering an agonist of Hscdc6 to the individual in such a manner that it enters tumor cells in the individual, introduction of the Hscdc6 agonist in G2 or M phase of the cell cycle prevents entry of the cell into mitosis, and thus results in tumor cell death. The invention also pertains to a method of inhibiting undesired cell proliferation in an individual comprising administering an agonist or antagonist of Hscdc6 to the individual in such a manner that the agonist or antagonist enters the cells in which it is desirable to inhibit proliferation.

An antagonist of Hscdc6 will prevent or reduce the activity of Hscdc6, and thereby prevent the replication of cellular DNA; cells with unreplicated DNA will enter mitosis and cell death will result. For example, methods of treatment include administering antagonists that are immunoglobulins having antigen binding regions of one of the hCdc6-26, hCdc6-37, hCdc6-34, hCdc6-39, or hCdc6-41 monoclonal antibodies. The method also includes administering, a humanized or chimeric immunoglobulin having antigen binding region or fragment derived from hCdc6-26, hCdc6-37, hCdc6-34, hCdc6-39, and hCdc6-41.

An agonist of Hscdc6 will prolong or increase the effects of Hscdc6, resulting in polyploidy and preventing mitosis, cells which are affected in this manner will undergo programmed cell death. The method of inhibiting cell proliferation can be used in the treatment of conditions associated with undesirable levels of cell proliferation, such as tumor growth or cancer.

The invention also encompasses a method of enhancing cell proliferation for therapy of a condition associated with loss of viable tissue in an individual comprising administering Hscdc6 or an agonist of Hscdc6 to an individual such that it enters cells in the individual. The activity of Hscdc6 or an Hscdc6 agonist causes initiation of DNA replication in the cell and entry of the cell into mitosis. The invention further relates to a method of diagnosing or aiding in the diagnosis of conditions associated with proliferative disorders in an individual; this method can also be used to predict the likelihood that an individual is at increased risk for a particular condition associated with abnormal cell proliferation. According to this method, by combining probes derived either from the isolated native sequence of the Hscdc6 gene or from the primers disclosed herein with DNA from an individual to be assessed, under conditions suitable for hybridization, it can be determined whether the individual possesses the gene. Hybridization conditions can be selected such that the probes will hybridize only with altered DNA and not with unaltered DNA; that is, the probes can be designed to recognize only particular alterations in the nucleic acid sequence of the gene, including addition of one or more nucleotides, deletion of one or more nucleotides or change in one or more nucleotides (including substitution of a nucleotide for one which is normally present in the sequence).

The claimed invention also pertains to kits (e.g., test kits) used in detecting the presence of hscdc6 in a sample comprising an antibody or functional portion thereof which binds to hscdc6, and one or more ancillary reagents suitable for detecting the presence of a complex between the antibody or portion thereof and said hscdc6. In particular, the antibodies can be hCdc6-26, hCdc6-37, hCdc6-34, hCdc6-39, or hCdc6-41. The kit can also further comprise one or more reagents for detecting an additional marker for a proliferative disorder (e.g., a marker that is not hscdc6, such as a Mcm protein).

BRIEF DESCRIPTION OF THE DRAWINGS

FIG. 1 illustrates the design of oligonucleotide primers for cloning of the genes described herein. Amino acid sequences from ORC1 proteins from *K. lactis* (Kl) (SEQ ID NOs.: 28,35,42) *S. cervisiae* (Sc) (SEQ ID NOs.: 29,32,36,39,43, 46) human (Hs) (SEQ ID NOs.: 30, 37, 44) and *S. pompe* (Sp) (SEQ ID NOs.: 31,33,38,40,45,47) were aligned in the region of three sequence blocks (Boxes 1, 3 and 4) which are conserved among these proteins, as well as cdc6p and cdc18+. Former primers (SEQ ID NOs.: 34,41) and Reverse primers (SEQ ID NO.: 48)are shown.

FIGS. 3A–3C illustrate the complete CDNA (SEQ ID NO: 1) and amino acid (SEQ ID NO: 2) sequences of Hscdc6. The putative initiation codon and the first in-frame stop codon are boxed.

FIGS. 4A and 4B illustrate a multiple sequence alignment of Hscdc6, Xcdc6 and related proteins from *S. cerevisiae* (SEQ ID NO. 49) and *S. pombe* (SEQ ID NO. 50). Amino acid residues that are identical in both vertebrate proteins, or in one or both vertebrate proteins and one or both fungal proteins, are indicated by dark shading, and conservative substitutions are indicated by light shading. Conserved sequence boxes are enclosed. Areas previously known to be conserved among fungal cdc6p and cdc18 proteins and among fungal and human orc1p are designated Box 1 through Box 6. Other highly conserved regions newly identified are designated as CSH boxes.

FIGS. 6A and 6B illustrate the partial cDNA sequence (SEQ ID NO: 3) and deduced amino acid sequence (SEQ ID NO: 4) of Xcdc6.

FIGS. 8A–8F show the genomic sequence of the hscdc6 gene that includes the coding region and portions of the noncoding regions (SEQ ID NOs: 5, 6, 7, 8, 9, 10, 11, 12, 13, 14, 15, 16, 17, 18, 19, 20, 21, 22, 23, 24, 25 and 26). The sequence of the promoter (SEQ ID NO: 5 and 6) is indicated. The bolded regions indicate the exons (SEQ ID NOs: 7, 9, 11, 13, 15, 17. 19, 21, 23, and 25) and the non-bolded regions indicate the introns (SEQ ID Nos: 8, 10, 12, 14, 16, 18, 20, 22, and 24).

DETAILED DESCRIPTION OF THE INVENTION

Figure 2:
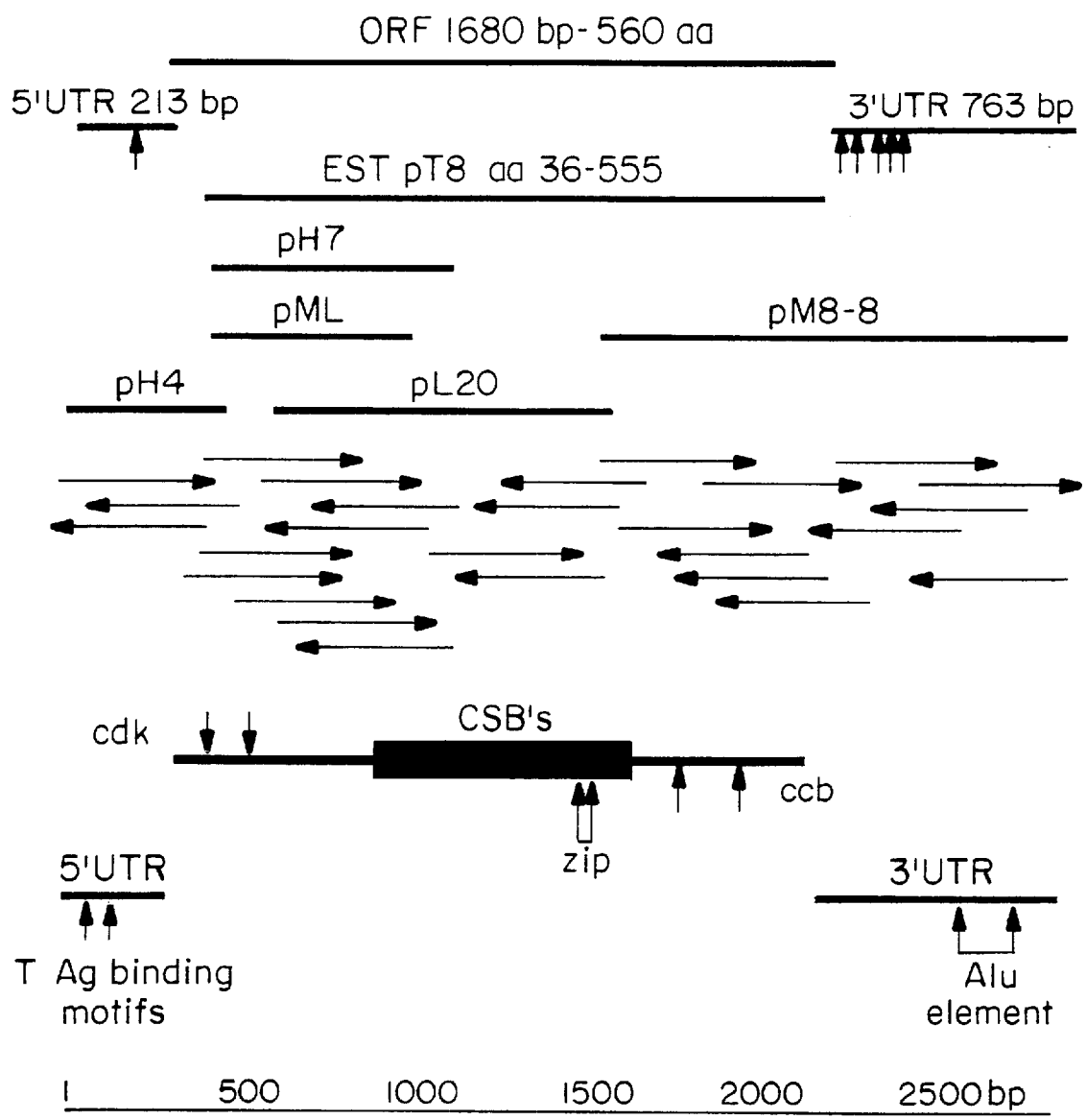
FIG. 2 illustrates the cloning results and sequencing strategy. In-frame stop codons are indicated with dark arrows pointing upwards. Horizontal arrows illustrate the sequencing strategy. Two consensus phosphorylation sites for cyclin-dependent kinases (cdk) are found in the amino terminal region of the protein and are indicated with light arrows pointing downwards. Two consensus sites potentially mediating destruction of the protein at specific stages of the cell cycle (ccb) are present toward the carboxyl terminus and are indicated with light arrows pointing upwards.

As described herein, vertebrate gyene sequences that encode novel proteins closely related to proteins known to control DNA replication and entry into mitosis in fungi have been cloned and characterized. Specifically, vertebrate cdc6 genes have been identified which function in the regulation of DNA replication and entry of cells into mitosis. In a particular embodiment, the gene sequence is a human gene sequence (Hscdc6; previously referred to as human CSH gene, particularly in U.S. application Ser. No.: 08/643,034 now U.S. Pat. No. 5,851,821 of which this application is a continuation-in-part application). In another embodiment, the gene sequence is a *Xenopus* laevis gene sequence (Xcdc6; previously referred to as a Xenopus CSH gene, particularly in U.S. application Ser. No.: 08/643,034 now U.S. Pat. No. 5,851,821 of which this application is a continuation-in-part application).

The genes of the present invention are members of a family of genes which function in cell cycle regulation, particularly in the regulation of DNA replication and/or the control of the entry of the cell into mitosis. The present invention also relates to the polypeptides or proteins encoded by the genes described herein, as well as to antibodies which bind the subject polypeptides or proteins. In particular embodiments of the invention, genes which function in the regulation of DNA replication or entry of a cell into mitosis have a nucleotide sequence comprising at least one nucleotide sequence selected from the group consisting of SEQ ID NO: 1, 3, 5, 6, 7, 8, 9, 10, 11, 12, 13, 14, 15, 16, 17, 1 8, 19, 20, 21, 22, 23, 24, 25, 26, and combinations thereof. In a particular embodiment the protein or polypeptide encoded by the genes described herein has the amino acid sequence of SEQ ID NO: 2 or SEQ ID NO: 4.

Cell Cycle Regulation

A particularly critical step in the cell cycle involves the decision to replicate DNA. In eukaryotic cells, the initiation of DNA replication has been studied most extensively in fungal species, particularly the budding and fission yeast, *Saccharomyces cerevisiae* and *Schizosaccharomyces pombe*, respectively. Less complete data acquired in insects, amphibians and humans suggest, however, that the fundamental mechanisms, and many of the proteins, involved in this process are similar in all eucaryotes (Sherr, *Cell* 79:551–555 (1994); Nigg, *BioEssays* 7:471 (1995)).

DNA replication is initiated from discrete locations within chromosomes by recruitment of an extensive set of proteins collectively termed the replication machinery (Stillman, *J. Biol. Chem.* 269:7047–7050 (1994a); Stillman, *Cell* 78:725–728 (1994b)). This process is best understood at present from studies on the yeast *S. cerevisiae* and *S. pombe* (Diffley, *Current Opinions in Cell Biology* 6:368–372 (1994); Rowley et al., *Biochimica et Biophysica Acta* 1217:239–256 (1994); Stillmani (1994a); Stillman (1994b)). Replication origins in *S. cerevisiae* and *S. pombe* consist of specific DNA sequences (replicators) that are bound by nuclear proteins to provide the framework on which the other components of the replication machinery are assembled (Marahrens and Stillman, *Science* 255:817–823 (1992); Dubey et al., *EMBO* 13:3638–3647 (1994); Marahrens and Stillman, *EMBO* 13:3395–3400 (1994); Newlon and Theis, *Current Opinions in Genetics and Development* 3:752–758 (1994); Rao et al., *Mol. Cell Biol.* 14:7643–7651 (1994); Theis and Newlon, *Mol. Cell Biol.* 14:7652–7659 (1994); Clyne and Kelly, *EMBO* 14:6348–6357 (1995); Rao and Stillman, *PNAS* 92:2224–2228 (1995); Rowley et al., *EMBO* 14:2631–2641 (1995); Huang and Kowalski, *Nucleic Acids Research* 24:816–823 (1996)).

In *S. cerevisiae*, a multi-subunit complex known as ORC (Origin Recognition Complex) binds to replicator sites within chromosomes (Bell and Stillman, *Nature* 357:128–134 (1992); Diffley and Cocker, *Nature* 357:169 (1992); Bell et al., *Science* 262:1844–1870 (1993); Li and Herskowitz, *Science* 262:1870–1874 (1993); Micklem et al., *Nature* 366:87–89 (1993); Diffley et al., *Cell* 78:303–316 (1994); Bell et al., *Cell* 83:563 (1995); Liang et al., *Cell* 81:667–676 (1995); Loo et al., *Mol. Cell Biol.* 6:741–756 (1995); Rao and Stillman (1995); Rowley et al. (1995)). ORC consists of six essential protein subunits (Palmer et al., (*Genetics* 125:763–774 (1990); Bell and Stillman (1992); Bell et al. (1995)), and at least some of them are found in other eukaryotic species (Ehrenhofer-Murray et al., *Science* 270:1671–1674 (1995); Gavin et al., *Science* 270:1667–1671 (1995); Gossen et al., *Science* 270:1674–1677 (1995); Muzi-Falconi and Kelly, *PNAS*

92:12475–12470 (1995); Carpenter et al., *Nature* 379:357 (1996)). Binding of ORC to replicator DNA sequences in vivo can be detected by footprinting techniques, and it appears that ORC is bound to the chromosomes throughout the cell cycle, but the pattern of nuclease digestion changes (Diffley and Cocker (1992); Diffley et al. (1994); Rowley et al. (1994); Dahmann et al., *Current Biology* 5:1257 (1995); Diffley, *Yeast* 11:1651–1670 (1995); Cocker et al., *Nature* 379:180 (1996)). This is consistent with the viewpoint that other factors interact with ORC to trigger the initiation of replication at the G1/S phase boundary.

In budding yeasts this triggering function resides, at least in part, in a protein called cdc6p (Hartwell, *J. Cell Biol.* 15:803–817 (1976); Lisziewicz et al., *Nucleic Acids Research* 16:11507–11520 (1988); Zhou et al., *J. Biol. Chem.* 264:9022–9029 (1989); Palmer et al., *Genetics* 125:763–774 (1990); Bueno and Russell, *EMBO* 11:2167–2176 (1992); Hogan and Koshland, *PNAS* 89:3098–3102 (1992); Zwerschke et al., *J. Biol. Chem.* 269:23351–23356 (1994); Liang et al. ( 1995); Piatti et al., *EMBO* 1141:3788–3799 (1995); Bruschi et al., *Mol. Genet* 249:8–18 (1996); Cocker et al. (1996)). Fission yeasts contain a closely related protein, cdc18, that appears to have a similar function (Kelly et al., *Cell* 74:371–382 (1993*a*); Kelly et al., *Cold Spring Harbor Symp Quant. Biol.* 58:637–644 (1993b); Nishitani and Nurse, Cell 83:397–405 (1995); Jallepalli and Kelly, *Genes and Development* 10:541–552 (1996); Leatherwood et al., *Nature* 379:360 (1996); Muzi-Falconi et al., *PNAS* 93:1566–1570(1996)). Extensive evidence, acquired from genetic and biochemical studies, supports the viewpoint that cdc6p/cdc18 proteins have a unique and important role in the initiation of DNA replication.

The CDC6 gene was cloned by several labs by complementation of a mutation causing a cell-division-cycle-specific growth arrest in *S. cerevisiae* (Hartwell (1976); Lisziewicz et al. (1988); Zhou et al. (1989); Bueno and Russell (1992)). The sequence of the largest subunit of ORC, the orc1p, is highly related to the sequences of the cdc6p/cdc18 proteins, particularly in and around a putative purine nucleotide binding motif(Bell et al. (1995)). Yeast strains bearing null mutations in CDC6 are nonviable, and strains bearing temperature sensitive mnutations in CDC6 suffer growth arrest with partially unreplicated DNA at the restrictive temperature (Lisziewicz et al. (1988); Zhou et al. (1989); Bueno and Russell (1992); Liang et al. (1995)). Even at temperatures permissive for viability, the frequency at which DNA replication is initiated from specific replicators is reduced in strains with CDC6 mutations (Liang et al. (1995); Piatti et al. (1995)). This phenotype can be reversed if multiple replicator sequences are located on the plasmid that is under selection (Hogan and Koshland (1992)).

Interestingly, over-expression of cdc18 protein results in repeated rounds of DNA replication in the absence of mitosis, such that cells accumulate concentrations of DNA greater than a 2N DNA content (normal for diploid cells) (Nishitani and Nurse (1995); Jallepalli and Kelly (1996)); Leatherwood et al. (1996)). A similar abnormality is a common defect in human cancer cells. In contrast, under-expression of cdc6p/cdc18 proteins causes under-replication of the genome and abnormal entry into mitosis (Kelly et al. (1993a) and (1993b); Liang et al. (1995); Piatti et al. (1995); Muzi-Falconi et al. (1996)). The abundance of functional cdc6p/cdc18 proteins appears, therefore, to be rate-limiting for initiation of DNA replication at individual replicators.

CDC6 and cdc18+ genes are expressed at specific stages of the cell cycle (Kelly et al. (1993a); Zwerschke et al. (1994); Piatti et al. ( 1995); Muzi-Falconi et al. (1996)). Expression of mRNA encoding cdcop peaks at the end of M phase in rapidly cycling *S. cerevisiae* cells, but a second pealk of expression is evident in G1 if G1 is prolonged (Zwerschke et al. (1994); Piatti et al. (1995)). In contrast, the cdc18+ gene is expressed only at the G1 to S phase transition (Kelly et al. (1993a)). Both of these proteins are very unstable; the half life of cdc18 protein and cdc6p has been estimated as 5 minutes or less (piatti et al. (1995); Jallepalli and Kelly (1 996),; Muzi-Falconi et al. (1996)). Concentrations of cdc18 protein peak at the G1/S boundary and decline during late S phase, consistent with a role in triggering DNA replication. A requirement for renewed synthesis of cdc6p/cdc18 proteins is an important component of the mechanism that ensures that each segment of chromosonmal DNA is replicated once, and only once, in each cell cycle.

Cdc6p and cdc18 proteins are rate limiting, for replication initiation and have additional regulatory functions in controlling subsequent progression through the cell cycle. A deficiency in functional cdc6p/cdc18 protein causes mitosis in the absence of DNA replication (reductional anaplhase) (Kelly et al. (1993a); Piatti et al. (1995)), leading to cell death. Conversely. overexpression of cdc18 protein stimulates additional rounds of DNA replication in the absence of mitosis promoting polyploidy (Nishitani and Nurse (1995)). Thus, a decline in the concentration of cdc6p/cdc18 protein after the initiation of DNA replication appears to be necessary to release checkpoint controls and permit entry into mitosis (Bueno and Russell ( 1992)). The abundance of cdc18 protein is down-regulated by the activity of mitotic cyclins and cyclin-dependent kinase activity, and up-regulated by cyclin-dependent kinase (CDK) inhibitors such as rum1 protein (Jallepalli and Kelly (1996)).

Cdc6p demonstrates both functional and physical interactions with ORC protein subunits that bind to origins of DNA replication (Li and Herskowitz (1993); Liang et al. (1995)). Concomitant expression of temperature-sensitive mutant forms of cdc6p and either Orc2p or Orc5p is lethal at temperatures permissive for strains bearing only single mutations (synthetic lethality) (Liang et al. ( 1995)). Conversely, high concentrations of cdc6p generated from multicopy plasmids can rescue DNA replication at non-permissive temperatures in yeast strains bearing temperature-sensitive mutations in the Orc5p gene. Furthermore, cdc6p is present in protein complexes immunoprecipitated from yeast nuclear protein extracts with monoclonal antibodies directed against ORC subunits (Liang et al. (1995)). It also appears that the *S. pombe* cdc18 protein may interact with ORC (Leatherwood et al. (1996)). Evidence indicates that the cdc6p protein may be an ATPase (Zweschke et al. ( 1994)). The putative purine nucleotide binding motif in the cdc6p is essential for viability in yeast (M. Weinreich and B. Stilman, unpublished data). In concert, these data establish an important role for cdc6p/cdc18 proteins in the initiation of DNA replication and in the progression of cells into mitosis when DNA replication is complete.

Cloning of Xcdc6 and Hscdc6

The amino acid sequences of the cdc6p and cdc18 proteins were aligned, along with those of human and yeast ORC1 proteins previously described (Bell et al. (1995); Gavin et al. (1995)). ORC1 proteins contain several regions closely related to cdc6p/cdc18, including a putative nucleotide binding/ATPase domain, but are otherwise dissimilar (Gavin et al. (1995)). Certain regions that are conserved between the cdc6p and cdc18 proteins are not present in any of the ORC1 proteins. Based on these sequences, six degenerate oligonucleotide primers tor the polymerase chain reaction (PCR) were designed, using blocks of 6 or 7 amino acids that were identical, or nearly so, in cdc6p and cdc18, but differed in two or more codons from sequences conserved among ORC1 proteins from *H. sapiens, K. lactis, S. pombe* and *S. cerevisiae*. This was important to avoid re-isolation of human ORC1 cDNA. The nucleotide sequence of each oligonucleotide primer was biased to reflect human usage codon probabilities. The design of primers that proved successful in amplifying partial Xenopus and human CDNA sequences from genes encoding Xcdc6 and Hscdc6 proteins is shown in FIG. 1. The primers were degenerate in the positions shown, and inosine (I) bases were included at positions of highest degeneracy in the predicted nucleotide sequence.

All six primers were tested in all possible combinations in polymerase chain reactions using cDNA prepared from human, amphibian or insect cells as the template. Amphibian and insect embryo mRNAs were used to make cDNA for this purpose because it was proposed that the embryo might store large amounts of the CDC6-related mRNA for the rapid rounds of cell division that occur in these organisms (Alberts et al. (1989)). A wide variety of reaction conditions were tested with a variety of template DNAs. The conditions that proved successful included 67 mM Tris HCl (pH 8.8), 16.6 mM ammonium sulfate, 10% dimethylsulfoxide, (6.7 mM EDTA, 8 mM magnesium chloride, 10 mM β-mercaptoethanol, 50 pmol of each oligonucleotide primer, 10 ng of DNA template, and 1 unit Taq polymearse in a total reaction volume of 25 µl. Conditions for PCR (29 cycles) included denaturation of DNA for 2 minutes (first cycle) or 40 seconds (subsequent cycles) at 94° C., primer annealing at 42° C. for 1 minute, and primer extension for 1 minute (cycles 1–28) or 5 minutes (cycle 29) at 72° C. Amplified products were purified after agarose gel electrophoresis and cloned into a plasmid vector (pCRII; Gahm et al., *PNAS USA* 88:10267–10271 (1991)). Complementary DNA inserts were sequenced from purified plasmid DNA using dideoxynucleotide chain termination chemistry (Sanger et al., *PNAS USA* 74:5463–5467 (1977)).

The most abundant PCR product identified from this screen was obtained using cDNA prepared from mRNA isolated from *Xenopus oocytes* as templates. The amplified product of 378 nuclcotides encoded a predicted amino acid sequence with greater similarity to cdc6p/cdc18 than to ORC1 proteins. Using the same *Xenopus oocyte* cDNA as template, additional PCR was performed using 5' and 3' rapid amplification of cDNA ends (RACE) techniques, which yielded additional Xenopus cDNA segments that included all of the segments conserved in the comparison of cdc6p and cdc18 proteins. The cloned Xenopus cDNA includes the initiation codon, but does not extend to the authentic 3' terminus of the coding sequence.

Based on the sequence of the Xenopus cdc6p-related protein, new sets of non-degenerate oligonucleotide primers were synthesized using regions conserved between the predicted Xenopus protein, cdc6p and cdc18. Further rounds of PCR were performed using cDNA reverse-transcribed from RNA isolated from human cells as the template. One of these new primers, containinig, the sequence 5'-CCTCTCAGCCCCAGGAAACG-3' (SEQ ID NO: 27) in combination with degenerate primers from the original set based on Box 1 or Box 3 (FIG. 1) generated amplification products of 459 and 687 nucleotides, respectively. The predicted amino acid sequence encoded within these segments exhibited greater similarity to cdc6p and cdc18 than to ORC1 proteins and was greater than 90% identical to the amino acid sequence of the predicted Xenopus protein.

The larger (687 nt) fragment of Hscdc6 cDNA obtained by PCR amplification was radiolabeled and used as the probe for screening a human CDNA library carried in bacteriophage lambda phage gt10. In the first round of screening of 900,000 phage plaques, 18 clones were positive in duplicate lifts. Of these 18, 5 clones were positive in duplicate in a second round of screening. Each of theses 5 clones was isolated following a third round of plaque purification after plating at low density. Phage DNA was purified and characterized by PCR and restriction digests. cDNA inserts were isolated and cloned into a plasmid vector for sequencing. Plasmid clones isolated from the human cDNA library and used to determine the complete nucleotide sequence of Hscdc6 are illustrated schematically in FIG. 2.

The human cDNA encoding Hscdc6 includes an open reading frame of 1680 nucleotides, encoding a protein ot 560 amino acids. The most upstream ATG, representing the putative initiation codon is flanked by an in-frame stop codon in the 5' untranslated region (UTR). The termination codon of this open reading frame is flanked by multiple in-frame stop codons in the 3' UTR, 763 bases of which were included in the largest CDNA clone isolated from the phage library. Five overlapping segments of this CDNA were cloned into plasmid vectors for sequencing (pH7, pML, pH4, pL20 and pM8-8).

The invention also includes the geCIoimiic sequence of hscdc6 (FIGS. 7 and 8A–F). FIGS. 8A–F illustrate, continuously, the coding regions (CR) and portions of the non-coding regions (NCR). The invention pertains to the nucleic acid sequence of the individual CR or NCR, or combinations thereof (e.g., SEQ ID NOs: 5, 6, 7, 8, 9, 10, 11, 12, 13, 14, 15, 16, 17, 18, 19, 20, 21, 22, 23, 24, 25, or 26). Furthermore, the invention includes the sequence of the promoter, SEQ ID NOs: 5 and 6, as shown in FIG. 8A. The sequence of the EST appears in FIG. 8F and is identified as SEQ ID NO: 26. The underlined portion of the EST sequence the region of overlap between cDNAs previously cloned and the EST sequence. The Figure contains nucleotides in lower case (FIG. 8A) and in superscript (FIG. 8B) which represent polymorphic sites in which the nucleotide sequence differs between the cDNAs and genomic clones from difference Sources. The initiation codon (ATG) is in SEQ ID NO: 9, beginning 15 nucleotides from the upstream splice junction. The stop codon (TAA) is in SEQ ID NO: 25 beginning 86 nucleotides from the upstream splice junction.

In addition, a match was identified to a human expressed sequence tag in the National Center for Biotechnology Information database. The sequenced region identified in the EST database represents only the region corresponding to amino acids 36–165 of Hscdc6. This region does not have sufficient identity to cdc6p or cdc18 to be identified without the additional sequence data obtained by cloning the partial Xenopus cDNA.

Other landmarks identified in the Hscdc6 sequence are shown in the lower portion of FIG. 2. The box labeled CSB indicates the region containing conserved sequence blocks shared with yeast cdc6p and cdc18 and ORC1 proteins. Two consensus phosphorylation sites for cyclin-dependent kinases (cdk) (Jans et al., *JBC* 270:17064–17067 (1995)) are found in the amino terminal region of the protein and are indicated with light arrows pointing downwards. Two consensus sites potentially mediating destruction of the protein at specific stages of the cell cycle (ccb) (Amon et al., (*Cell* 77:1037–1050 (1994)) are present toward the carboxyl terminus and are indicated with light arrows pointing upwards. A potential leucine zipper (zip) overlaps with conserved sequence block 4. The 5' UTR includes two consensus sites for DNA binding of SV40 T antigen (T Ag) (SenGupta and Borowiec, *EMBO* 4 (1994)), and an Alu repeat sequence (Alu element) is found within the 3' UTR.

Figure 6B:
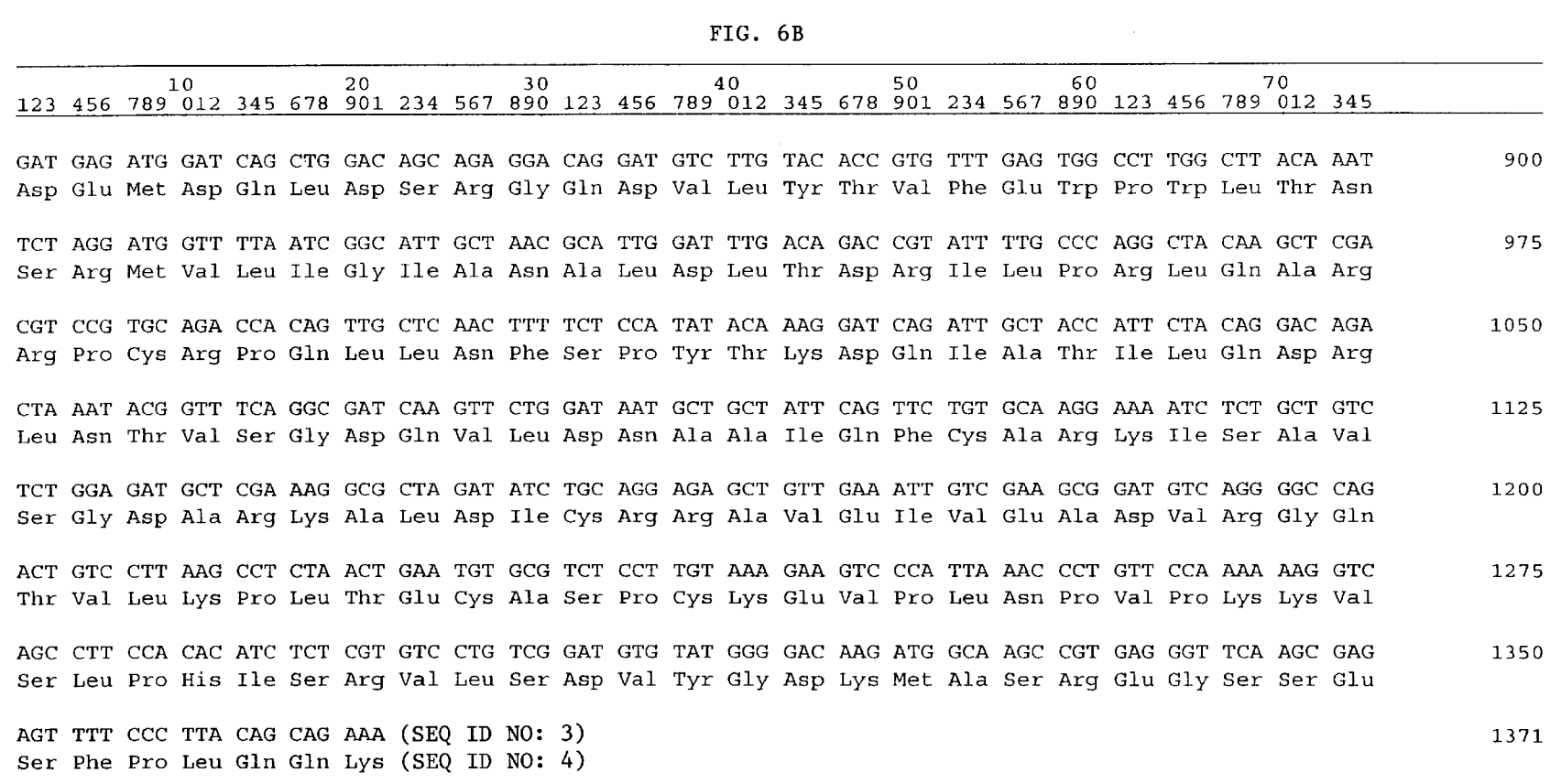

The complete nucleotide sequence of human Hscdc6 cDNA is shown in FIGS. 3A–3C (SEQ ID NO: 1), and the partial nucleotide sequence of Xcdc6 CDNA is shown in FIGS. 6A and 6B (SEQ ID NO: 3). The predicted amino acid sequences are also shown (SEQ ID NOS: 2 and 4, respectively), and the alignment of these amino acid sequences with the fungal cdc6p/cdc18 proteins is shown in FIGS. 4A and 4B.

The question addressed was whether the model developed from studies in yeast to explain how replication origins are activated once and only once in each cell cycle is also valid in mammalian cells. According to this model, Cdc6, Mcm proteins, and possibly other factors bind during late M/early G1 to specific locations within the genome via interactions with ORC. Formation of these pre-RCs likely make the chromatin structure permissive for initiation of DNA replication. In response to cell growth and proliferation signalling, multiple protein kinases, including CDKs and Dbf4-Cdc7, activate the pre-RC, eventually leading to entry into S phase. A good deal of evidence indicates that CDKs are also involved in the inhibition of re-replication during the G2 and M phases of the cell cycle, by exciting a negative control on the formation of functional pre-RCs. Inactivation of these kinases in yeast or Drosophila enables the cells to undergo a second round of DNA replication in the absence of mitosis. Conversely, activation of CDKs in early G1 cells blocks pre-RC formation in yeast. Cdc6 (Cdc18) is a key target and participant in control of DNA replication during the yeast cell cycle.

The data indicates that this model is valid in mammalian cells. Human Orc2 remains bound to chromatin throughout the entire cell cycle and thus the potential for ORC to serve as the DNA-bound landing pad for other initiation proteins is conserved. Formation of pre-RCs, defined at least by the loading of Cdc6 and Mcm proteins onto chromatin, occurs roughly at the same time of the cycle; human Mcm3 and Mcm5 are targetted to chromatin from late M/early G1 until the onset of S phase and are released from chromatin afterwards (see FIG. 11). The Mcm loading period corresponds to a window of opportunity for formation of pre-RCs in yeast, where the CDKs are inactive. This Mcm alternation between soluble and chromatin-bound states during the cell cycle is consistent with immunostaining and biochemical data.

In contrast to the Mcm proteins, the regulation of Cdc6 protein across the cell cycle is different between yeast and mammalian cells. In both budding and fission yeast, Cdc6 (Cdc18) are very labile proteins, targeted for destruction by CDK-dependent phosphorylation and subsequently degraded by the ubiquitin/proteosome pathway shortly after G1/S transition. On the contrary, human Cdc6 levels do not drop as cells enter S phase, but keep accumulating during the rest of the cell cycle and are destroyed during mitosis. In three different cell lines tested, a short window in the cell cycle was detected that corresponds to very early G1 phase in which Cdc6 is almost totally absent. Contrasting with this observation, Cdc6 has recently been reported to be constitutively expressed in HeLa cells. This apparent contradiction could be explained by differences in the experimental procedures used. MANCA or 293 cells were collected by centrifugal elutriation under conditions in which the cells in G1 were divided into at least four fractions according to cell size, therefore discriminating between early and late G1. In other reports in which G1 cells were obtained after synchronizing cultures with drugs or elutriation, early, mid- and late G1 cells were likely pooled together in only one fraction, and therefore, Cdc6 would have already been expressed in many of these cells.

Figure 11:
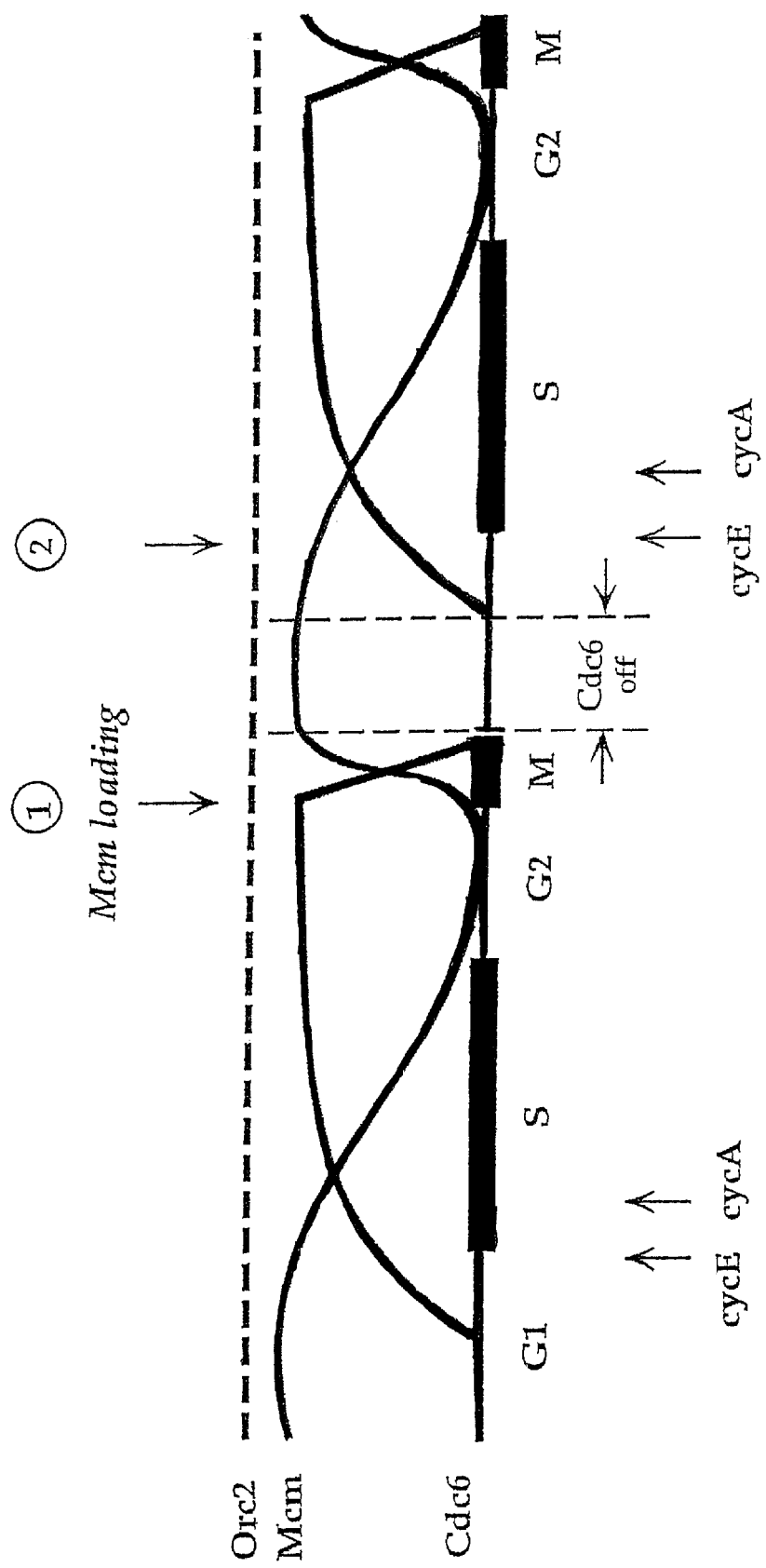
FIG. 11 shows the dynamics of chromatin association/ dissociation of human Orc2, Cdc6, Mcm3 and Mcm5 across the cell cycle. The numbers in circles indicate two putative execution points for Cdc6 function.

Interestingly, an increasing amount of Cdc6 was found on chromatin from G1 until mitosis (See FIG. 11). After the G1/S transition, however, a fraction of Cdc6 was also found in soluble form, perhaps reflecting cytoplasmic localization. In a recent report, the subcellular localization of recombinant, epitope-tagged Cdc6 that was overexpressed in cells was detected by immunostaining. Saha, P., et al., *Mol. Cell. Biol.* 18:2758–2767 (1998). Cdc6 was found mostly in the nuclei of G1 cells, but its localization changed to the cytoplasm in S phase. Although this study reflects overexpressed Cdc6 and our study focuses on the endogenous protein, both observations can be reconciliated. First, soluble Cdc6 was also detected after the G1/S transition. Second, the amount of Cdc6 that remains bound to chromatin after the G1/S transition might not be detected by immunostaining due to epitope masking. The significance of the possible shuttling of Cdc6 between the nucleus and cytosol is uncertain at this point, but it is not essential to prevent re-replication.

One major function of yeast Cdc6 (Cdc18) seems to be the loading of Mcm proteins onto ORC-bound chromatin. This function is likely to be conserved in mammalian cells. However, the DNA-bound pool of Cdc6 does not recruit Mcm proteins onto chromatin during G2 phase, suggesting that the negative control exerted by active CDKs on the formation of pre-RCs is also conserved. Evidence supporting a role for CDKs in regulating MCM protein loading onto chromatin has recently been demonstrated. Alternatively, Mcm loading onto chromatin bound Cdc6 might be regulated by other factors, such as geminin, a Xenopus protein that is also destroyed as cells progress through mitosis.

Cdc6 is a Limiting Factor for S Phase Entry hCdc6p is absent in early G1 cells, but produced soon thereafter, before S phase, indicating that Cdc6 is a rate-limiting factor for entry into S phase. Experiments in Drosophila and mammalian tissue culture cells have identified E2F-1 and cyclin E as crucial factors for driving, quiescent or G1 cells into S-phase. In Drosophila, induction of S phase by E2F requires cyclin E as a downstream target. However, in some embryonic tissues, cyclin E is constitutively expressed and acts as an upstream activator of E2F. On the other hand, in mammalian cells, overexpression of E2F-1 drives quiescent cells into S-phase without cyclin E activation and conversely, cyclin E overexpression can drive G1-arrested cells into S phase in the absence of detectable E2F activity. It has been proposed that the functions of E2F and cyclin E might converge by their cooperative control of another gene, whose product would be rate-limiting for initiation of DNA synthesis. Cdc6 is a good candidate, especially because its expression has been shown to be regulated by the transcription factor family E2F.

The possibility exists that Cdc6 is rate-limiting for DNA replication cell lines stably-transfected and constitutively produce hCdc6p, even in early G1 cells. In addition to MCM loading in late M, mammalian Cdc6 can fulfil a second, rate-limiting function at the G1/S phase transition that requires newly synthesized Cdc6. For instance, Cdc6 could contribute to loading of other factors in the pre-RC, or help formation of the pre-IC that contains Cdc45 protein. Alternatively Cdc6 could catalyze some biochemical process within the pre-RC or pre-IC, perhaps after activation by phosphorylation. A third interesting possibility is that mammalian Cdc6 could be required to hinder Mcms to bind origins in S and G2 phase. This would explain why Cdc6 keeps accumulating during the cell cycle and it is only degraded at mitosis.

hCDC6 gene is preferentially expressed in tissues with active cellular proliferation. In addition, data shows that Cdc6 proteins are overexpressed in cell lines derived from transformed cells compared to normal, diploid cells, perhaps reflecting the deregulation of E2F-dependent transcription. Solt agar growth assays are performed to address the question whether overexpression of Cdc6 is sufficient to induce anchorage-independent growth of mammalian cells. Taken together, our data suggest that Cdc6 is a key regulator during mammalian cell proliferation. As such, Cdc6 is an ideal target for cancer diagnosis and therapy.

The present invention relates to genes which function in the regulation of DNA replication or the entry of a cell into mitosis and which have a nucleotide sequence which hybridizes under low, medium or high stringency hybridization conditions (e.g., for selective hybridization) to the DNA sequence of SEQ ID NOS: 1, 3, 5, 6, 7, 8, 9, 10, 11, 12, 13, 14, 15, 16, 17, 18, 19, 20, 21, 22 , 23, 24, 25, 26, or a portion thereof. Stringent hybridization conditions for nucleic acid molecules are well known to those skilled in the art and can be found in standard texts such as *Current Protocols in Molecular Biology*, John Wiley & Sons, N.Y. ( 1998), pp. 2.10.1–2.10.16 and 6.3.1–6.3.6, the teachings of which are hereby incorporated by reference. As understood by those of ordinary skill, the exact conditions can be determined empirically and depend on ionic strength, temperature and the concentration of destabilizing agents such as foramide or denaturing agents such as SDS. Other factors considered in determining the desired hybridization conditions include the length of the nucleic acid sequences, base composition, percent mismatch between the hybridizing sequences and the frequency of occurrence of subsets of the sequences within other non-identical sequences. Thus, equivalent conditions can be determined by varying one or more of these parameters while maintaining, a similar degree of identity or similarity between the two nucleic acid molecules. Typically, conditions are used such that sequences at least about 60%, at least about 70%, at least about 80% at least about 90% or at least about 95% or more identical to each other remain hybridized to one another. In one non-limiting example, nucleic acid molecules are allowed to hybridize in 6×sodium chloride/sodium citrate (SSC) at about 45° C., followed by one or more low stringency washes in 0.2× SSC/0.1% SDS at room temperature, or by one or more moderate stringency washes in 0.2×SSC/0.1% SDS at 42° C., or washed in 0.2×SSC/0.1% SDS at 65° C. for high stringency.

The xcdc6 and/or hscdc6 protein and nucleic acid sequences of the invention include homologues, as defined herein. Honologous proteins and nucleic acid sequences can be determined using methods known to those of skill in the art. Initial homology searches can be performed at NCBI against the GenBank (release 87.0), EMBL (release 39.0), and/or SwissProt (release 3.0) databases using the BLAST network service. Altshul, SF, et al, *Basic Local Alignment Search Tool*, J. Mol. Biol. 215:403 (1990); Altschul, Stephen f., Gapped BLAST and PSI-BLAST: *A new generation of protein database search programs*, Nucleic Acids Res. 25:3389–3402 (1998), the teachings of which are incorporated herein by reference in their entirety. Computer analysis of nucleotide sequences can be performed using the MOTIFS and the FindPatterns subroutines of the Genetics Computing Group (GCG, version 8.0) software. Protein and/or nucleotide comparisons can also be performed according to Higgins and Sharp (Higgins, D. G. and P. M. Sharp, "Description of the method used in CLUSTAL," *Gene,* 73:237–244 (1988)). Homologous proteins and/or nucleic acid sequences to the xcdc6 and/or hscdc6protein and/or nucleic acid sequences that encode the xcdc6 and/or hscdc6 protein are defined as those molecules with greater than 60% sequence identity and/or similarity (e.g., 65%, 70%, 75%, 80%, 85%, 90%, or 95% homology).

Accordingly, the invention pertains to nucleotide sequences which have a substantial identity with the nucleotide sequences described herein; particularly preferred are nucleotide sequences which have at least about 90%, and more preferably at least about 95% identity with nucleotide sequences described herein. Particularly preferred in this instance are nucleotide sequences encoding polypeptides having at least one activity of the novel proteins and polypeptides described herein. For example, preferred nucleotide sequences encoding a polypeptide having the same or similar biological activity as Hscdc6 and/or Xcdc6, and nucleotide sequences encoding a polypeptide with the same or similar immunogenic or antigenic properties as Hscdc6 and/or Xcdc6 are within the scope of the invention. As used herein, activities of the protein or polypeptide include, but are not limited to, catalytic activity, binding function, antigenic function and oligomerization function.

As used herein, an "isolated" gene or nucleotide sequence is intended to mean a gene or nucleotide sequence which is not flanked by nucleotide sequences which normally (in nature) flank the gene or nucleotide sequence (as in genomic sequences) and/or has been completely or partially purified from other transcribed sequences (as in a cDNA or RNA library). Thus, an isolated gene or nucleotide sequence can include a gene or nucleotide sequence which is synthesized chemically or by recombinant means. Thus, recombinant DNA contained in a vector are included in the definition of "isolated" as used herein. Also, isolated nucleotide sequences include recombinant DNA molecules in heterologous host cells, as well as partially or substantially purified DNA molecules in solution. In vivo and in vitro RNA transcripts of the DNA molecules of the present invention are also encompassed by "isolated" nucleotide sequences. Such isolated nucleotide sequences are useful in the manufacture of the encoded protein, as probes for isolating homologous sequences (e.g., from other mammalian species), for gone mapping (e.g., by in situ hybridization with chromosomes), or for detecting expression of the Hscdc6 gene in tissue (e.g., human tissue), such as by Northern blot analysis.

The present invention also pertains to nucleotide sequences which are not necessarily found in nature but which do, in tact, encode the described proteins and polypeptides. Thus, DNA molecules which comprise a sequence which is different from the naturally-occuring nucleotide sequence but which, due to the degeneracy of the genetic code, encode the proteins and polypeptides of the present invention are the subject of this invention. The invention also encompasses variations of the nucleotide sequences of the invention, such as those encoding, portions, analogues or derivatives of the described proteins. Such variations can be naturally-occurring, such as in the case of allelic variation, or non-naturally-occurring, such as those induced by various mutagens and mutagenic processes. Intended variations include, but are not limited to, addition, deletion and substitution of one or more nucleotides which can result in conservative or non-conservative amino acid changes, including additions and deletions. The nucleotide or amino acid variations can be silient; that is, they do not alter the characteristics or activity of the protein.

The invention described herein also relates to fragments of the isolated nucleic acid molecules described above. The term "fragment" is intended to encompass a portion of a nucleotide sequence described herein which is from at least about 25 contiguous nucleotides to at least about 50contiguous nucleotides or longer in length; such fragments are useful as probes, e.g., for diagnostic methods and also as primers. Particularly preferred primers and probes selectively hybridize to the nucleic acid molecule encoding the Hscdc6 protein described herein. For example, fragments which encode antigenic regions of the protein described herein are useful.

Figure 5:
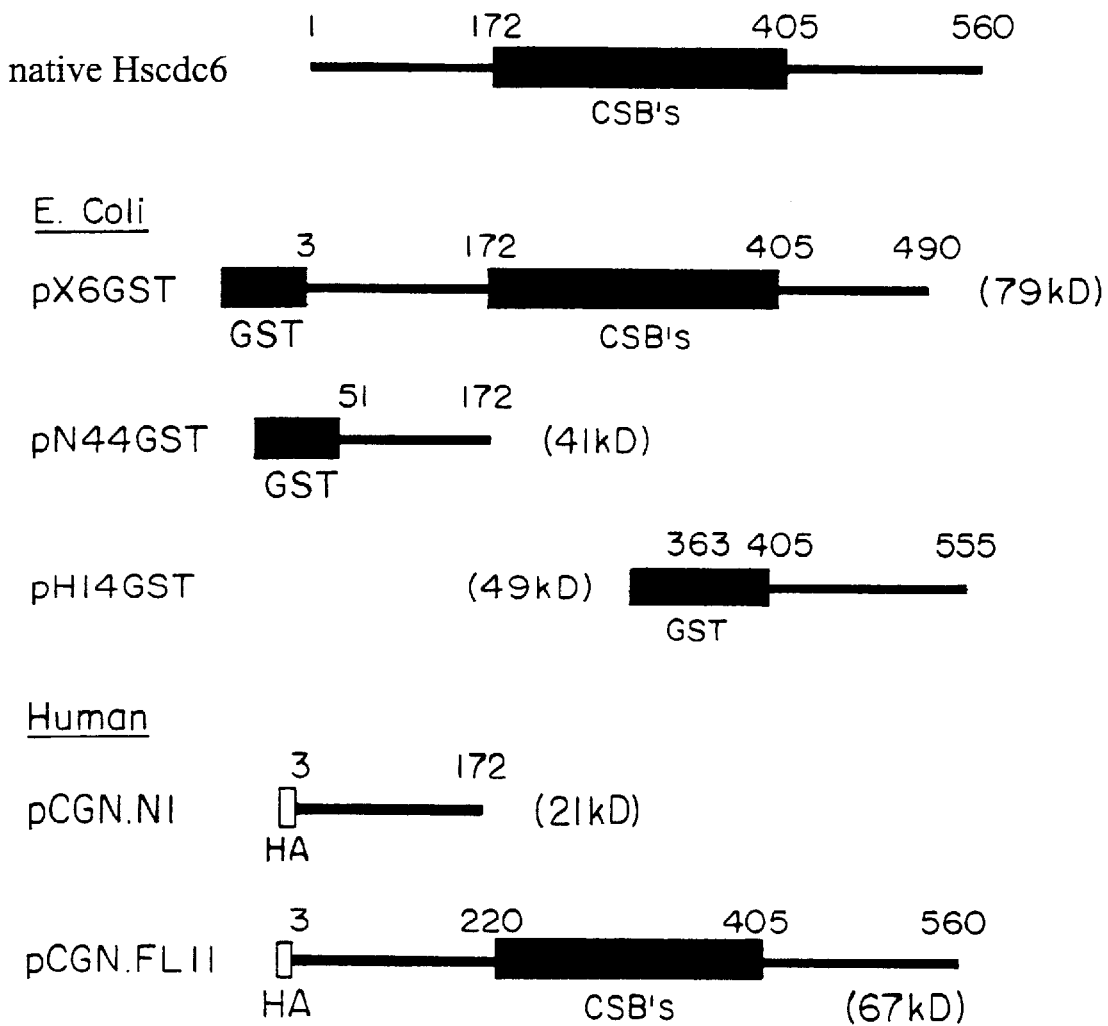
FIG. 5 illustrates plasmid constructions for expression of recombinant Hscdc6 in bacteria and in human cells.
Figure 7:
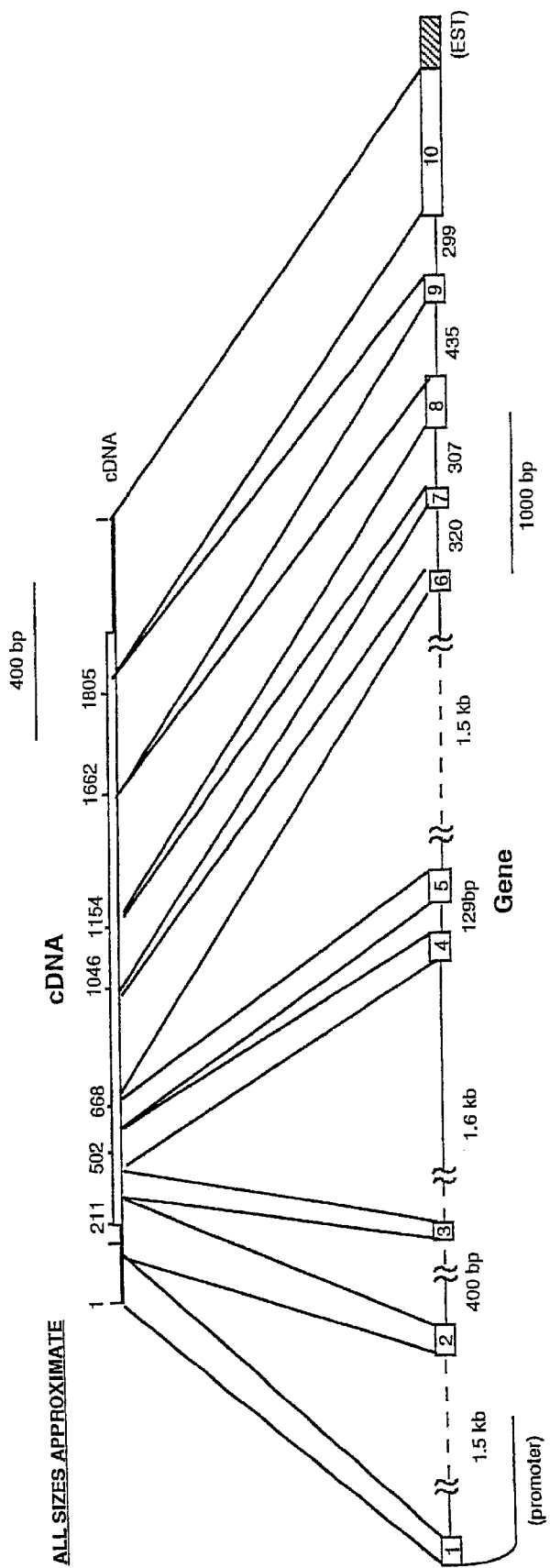
FIG. 7 is a schematic that maps the hscdc6 gene.

Segments of Hscdc6 cDNA were engineered into plasmid vectors for expression of recombinant protein in bacteria and in human cells. The design of these expression plasmids is illustrated schematically in FIG. 5. Portions of Hscdc6 and Xcdc6 were expressed as GST fusion proteins under the control of the lac Z promoter in E. coli, and recombinant fusion proteins were purified by binding to glutathione-Sepharose beads. Purified recombinant proteins were used to immunize rabbits to generate specific antibodies directed against Hscdc6 and Xcdc6. These antibodies recognize the recombinant protein expressed in E. coli.

Full-length or partial Hscdc6 cDNA sequences were also inserted into a mammalian vector in which expression of recombinant proteins is controlled by the major Cytomegalovirus (CMV) immediate early promoter/enhancer, and the initiation codon is positioned so as to insert an influeuza virus hemagglutinin antigen (HA) tag into the recombinant protein (Tanaka and Herr, Cell 160:375–386 (1990)).

The invention also provides additional expression vectors containing a nucleic acid sequence encoding a polypeptide of a Hscdc6 or Xcdc6 gene which is operably linked to at least one regulatory sequence. "Operably linked" is intended to mean that the nucleotide sequence is linked to a regulatory sequence in a manner which allows expression of the nucleic acid sequence. Regulatory sequences are art-recognized and are selected to produce a polypeptide which functions in the regulation of DNA replication and/or entry of the cell into mitosis. Accordingly, the term "regulatory sequence" includes promoters, enhancers, and other expression control elements which are described in Goeddel, *Gene Expression Technology: Methods in Enzymology* 185, Academic Press, San Diego, Calif. ( 1990). It should be understood that the design of the expression vector may depend on such factors as the choice of the host cell to be transformed and/or the type of protein desired to be expressed. For instance, the polypeptides of the present invention can be produced by ligating the cloned gene, or a portion thereof, into a vector suitable for expression in either prokaryotic cells, eukaryotic cells or both (see, for example, Broach, et al., *Experimental Manipulation of Gene Expression*, ed. M. Inouye (Academic Press, 1983) p. 83; *Molecular Cloning: A Laboratory Manual*, 2nd Ed., ed. Sambrook et al. (Cold Spring Harbor Laboratory Press, 1989) Chapters 16 and 17).

Prokaryotic and eukaryotic host cells transfected by the described vectors are also provided by this invention. For instance, cells which can be transfected with the vectors of the present invention include, but are not limited to, bacterial cells such as E. coli (e.g., E. coli K12 strains, Streptomyces, Pseudomonas, Serratia marcescens and Salmonella typhimurium, insect cells (baculovirus) including Drosophila, fungal cells, such as yeast cells, plant cells and mammalian cells, such as thymocytes, Chinese hamster ovary cells (CHO), and COS cells.

Thus, a nucleotide sequence derived from the cloning of the Hscdc6 and Xcdc6 genes described herein can be used to produce a recombinant form of the protein via microbial or eukaryotic cellular processes. Ligating the polynucleotide sequence into a gene construct, such as an expression vector, and transfominig or transfecting into hosts, either eukaryotic (yeast, avian, insect, plant or mammalian) or prokaryotic (bacterial cells), are standard procedures used in producing other well known proteins. Similar procedures, or modifications thereof, can be employed to prepare recombinant proteins according to the present invention by microbial means or tissue-culture technology. Accordingly, the invention pertains to the production of proteins or polypeptides of the present invention by recombinant technology.

Immunoglobulins Having Specificity for hscdc6

The terms "anti-hsedc6 antibody," "hscdc6 immunoglobulin," refer to an immunoglobulin or a fragment thereof having specificity for hscdc6. The antibodies can be polygonal or monoclonal, and the term antibody is intended to encompass both polyclonal and monoclonal antibodies. The terms polygonal and monoclonal refer to the degree of homogeneity of an antibody preparation, and are not intended to be limited to particular methods of production.

The present invention relates to antibodies which bind a polypeptide or protein which functions in DNA replication or entry of a cell into mitosis. For instance, polyclonal and monoclonal antibodies which bind to the described polypeptide or protein are within the scope of the invention. A mammal, such as a mouse, hamster or rabbit, can be immunized with an immunogenic form of the polypeptide or protein (e.g., the entire protein or an antigenic fragment of the polypeptide or protein which is capable of eliciting an antibody response). Techniques for conferring immunogenicity on a protein or peptide which is itself not immunogenic include conjugation to carriers or other techniques well known in the art. The protein or polypeptide can be administered in the presence of an adjuvant. The progress of immunization can be monitored by detection of antibody titers in plasma or serum. Standard ELISA or other immunoassays can be used with the immunogen as antigen to assess the levels of antibody.

Anti-hscdc6 antibodies can be raised against an appropriate immunogen, such as isolated and/or recombinant hscdc6 polypeptide or portion thereof (including, synthetic molecules, such as synthetic peptides). In one embodiment, antibodies can be raised against an isolated and/or recombinant hscdc6 or portion thereof (e.g., a peptide) or against a host cell which expresses recombinant hscdc6 or a portion thereof. In addition, cells expressing recombinant hscdc6such as transfected cells, can be used as immunogens or in a screen for antibody which binds receptor.

Preparation of immunizing antigen, and polyclonal and monoclonal antibody production, can be performed using any suitable technique. A variety of methods have been described (see e.g., Kohler et al. *Nature* 215: 495–497 (1975) and *Eur. J. Immmunol* 6:511–519 (1976); Milstein et. al., *Nature* 266: 550–552 (1977); Koprowski et al., U.S. Pat. No. 4,172,124; Harlow, E. and D. Lane, 1988, *Antibodies: A Laboratory Manual*, (Cold Spring Harbor Laboratory: Cold Spring Harbor, N.Y.); *Current Protocols In Molecular Biology*, Vol. 2 (Supplement 27, Summer 1994), Ausubel, F. M. et al., Eds., (John Wiley & Sons: New York, NY), Chapter 11, (1991)).

Following immunization, anti-peptide antisera can be obtained from the immunized animal, and if desired, polyclonal antibodies can be isolated from the serum. As described herein, purified recombinant proteins generated in E. coli were used to immunize rabbits to generate specific antibodies directed against Hscdc6. These antibodies recognize the recombinant protein expressed in *E. coli*. Monoclonal antibodies can also be produced by standard techniques which are well known in the art (Kohler and Milstein, *Nature* 256:495–497 (1975); Kozbar et al., *Immunology Today* 4:72 (1983); and Cole et al., Monoclonal Antibodies and Cancer Therapy, Alan R. Liss, Inc., pp. 77–96 (1985)). Generally, a hybridomia is produced by fusing a suitable immortal cell line (e.g., a myeloma cell line such as SP2/0) with antibody producing cells. The antibody producing cell, preferably those of the spleen or lymph nodes, can be obtained from animals immunized with the antigenic of interest. The fused cells (hybridomas) can be isolated using selective culture conditions, and cloned by limiting dilution. Cells which produce antibodies with the desired specificity can be selected by a suitable assay (e.g., ELISA).

Other suitable methods of producinig or isolating antibodies of the requisite specificity can be used, including for example, methods which select recombinant antibody from a library, or which rely upon immunization of transgenic animals (e.g., mice) capable of producing a full repetoire of human antibodies (see e.g., Jalcobovits et al., *Proc. Natl. Acad. Sci. USA,* 90: 2551–2555 (1993); Jakobovits et al *Nature,* 362: 255–258 (1993); Lonberg et al., U.S. Pat. No. 5,545,806; Surani et al., U.S. Pat. No. 5,545,807).

In particular, the invention encompasses five monoclonal antibodies raised against and having specificity for hscdc6 (e.g., mouse anti-human monoclonal antibodies): hCdc6-26, hCdc6-37. hCdc6-34, hCdc6-39, and hCdc6-41. The hybridomas which make the hCdc6-26 and hCdc6-37 antibodies were deposited on behalf of Cold Spring Harbor Laboratory and University of Texas System under conditions of the Budapest Treaty with the American Type Culture Collection (ATCC), 10801 University Boulevard, Manassas, Va. 20110-2209, USA on Oct. 30, 1998 under accession numbers HB12590 and HB12591, respectively. Both the hCdc6-26 and hCdc6-37 monoclonal antibodies have an IgC isotype (hCdc6-26 is an IgG2a/k isotype and hCdc6-37 is an IgG1/k isotype).

Single chain antibodies, and chimeric, humanized or primatized (CDR-grafted), or veneered antibodies, as well as chimeric, CDR-grafted or veneered single chain antibodies, comprising portions derived from different species, and the like are also encompassed by the present invention and the term "antibody". The various portions of these antibodies can be joined together chemically by conventional techniques, or can be prepared as a contiguous protein using genetic engineering techniques. For example, nucleic acids encoding a chimeric or humanized chain can be expressed to produce a contiguous protein. See, e.g., Cabilly et al., U.S. Pat. No. 4,816,567; Cabilly et al., European Patent No. 0,125,023 B1; Boss et al., U.S. Pat. No. 4,816,397; Boss et al., European Patent No. 0,120,694 B1; Neuberger, M. S. et al., WO 86/01533; Neuberger, M.S. et al., European Patent No. 0,194,276 B1; Winter, U.S. Pat. No. 5,225,539; Winter, European Patent No. 0,239,400 B1; Queen et al., European Patent No. 0 451 216 B1; and Padlan, E. A. et al., EP 0 519 596 A1. See also, Newman, R. et al., *BioTechnology* 10: 1455–1460 (1992), regarding primatized antibody, and Ladner et al., U.S. Pat. No. 4,946,778 and Bird, R. E. et al., *Science,* 242. 423–426 (1988)) regarding single chain antibodies.

The claimed invention relates to a humanized or chimeric immunoglobulin having binding specificity for hscdc6, comprising an antigen binding region of nonhuman origin derived from the hCdc6-26, hCdc6-37, hCdc6-34, hCdc6-39, or hCdc6-41 antigen binding regions and at least a portion of an immunoglobulin of human origin. Preferably, the humanized hscdc6 immunoglobulins can bind with an affinity of at least about $10^7$ M-1, preferably at least about $10^8$ M-1, and more preferably at least about $10^9$ M-1. In one embodiment, the humanized immunoglobulin includes an antigen binding region of nonhuman origin which binds hscdc6 and a constant region derived from a human constant region. In another embodiment, the humanized immunoglobulin which binds hscdc6 comprises a complementarity determining region of nonhuman origin and a variable framework region of human origin, and optionally, a constant region of human origin. For example, the humanized immunoglobulin can comprise a heavy chain and a light chain, wherein the light chain comprises a complementarity determining region derived from an antibody of nonhuman origin which binds hscdc6 and a framework region derived from a light chain of human origin, and the heavy chain comprises a complementarity determining region derived from an antibody of nonhuman origin which binds hscdc6 and a framework region derived from a heavy chain of human origin. Also, the claimed invention, individually or in a functional combination, embodies the light chain, the heavy chain, the variable region, the variable light chain and the variable heavy chain.

The claimed invention relates to a humanized hscdc6 antibody that possesses substantially the same binding specificity as the murine hscdc6 antibodies (e.g., hCdc6-26, hCdc6-37, hCdc6-34, hCdc6-39, or hCdc6-41) from which the humanized antibody is made, but with reduced immunogenicity in primates (e.g., humans). The humanized hscdc6 antibody preferably has about, substantially the same binding affinity as the murine counterpart.

Naturally occurring immunoglobulins have a common core structure in which two identical light chains (about 24 kD) and two identical heavy chains (about 55 or 70 kD) form a tetramer. The amino-terminal portion of each chain is known as the variable (V) region, also referred to as the "antigen binding" region, and can be distinguished from the more conserved constant (C) regions of the remainder of each chain. Within the variable region of the light chain is a C-terminal portion known as the J region. Within the variable region of the heavy chain, there is a D region in addition to the J region. Most of the amino acid sequence variation in immunoglobulins is confined to three separate locations in the V regions known as hypervariable regions or complementarity determining regions (CDRs) which are directly involved in antigen binding. The variable region is the portion of the antibody that binds to the antigen. The constant region allows for various functions such as the ability to bind to Fc receptors on phagocytic cells, placental cells, mast cells, etc. The light and heavy chains each have a variable region and a constant region. Accordingly, the claimed invention relates to a humanized immunoglobulin having binding specificity to hscdc6. The humanized immunoglobulin comprises a light chain and a heavy chain in which two light chains and two heavy chains form the tetramer.

The variable region further constitutes two types of regions, a framework region (FR) and a complementarity determining region (CDR). CDRs are hypervariable regions that contain most of the amino acid sequence variation in immunoglobulins. Proceding from the amino-terminus. these regions are designated CDR1, CDR2 and CDR3, respectively. The CDRs are held in place by more conserved FRs. Proceeding from the amino-terminus, these regions are designated FR1, FR2, FR3, and FR4, respectively. The locations of CDR and FR regions and a numbering system have been defined by Kabat et al. (Kabat, E. A. et al., Sequences of Proteins of Immunological Interest, Fifth Edition, U.S. Department of Health and Human Services, U.S. Goverment Printing Office (1991). During the process of humanizing an immunoglobulin, the CDRs from an antibody having specificity for hscdc6 from a non-human species is grafted into the CDRs of a human antibody. The resulting humanized antibody has CDRs from a non-human species such as a mouse and FRs from a human antibody, whereby the humanized antibody maintains its antigenic specificity and affinity to hscdc6.

The claimed invention also relates to a humanized immunoglobulin light chain or a humanized immunoglobulin heavy chain. In one embodiment, the invention relates to a humanized light chain comprising, one or more light chain CDRs of nonhuman origin and a human light chain framework region. In another embodiment, the invention relates to a humanized immunoglobulin heavy chain comprising, one or more heavy chain CDRs of nonhuman origin and a human heavy chain framework region. The CDRs can be derived from a nonhuman immunoglobulin such as murine heavy and light variable region chains which are specific to hscdc6.

Human immunoglobulins can be divided into classes and subclasses, depending on the isotype of the heavy chain. The classes include IgG, IgM, IgA, IgD and IgE, in which the heavy chains are of the gamma ($\gamma$), mu ($\mu$), alpha ($\alpha$), delta ($\delta$) or epsilon ($\epsilon$) type, respectively. Subclasses include IgG1, IgG2, IgG3, IgG4, IgA1 and IgA2, in which the heavy chains are of the $\gamma1$, $\gamma2$, $\gamma3$, $\gamma4$, $\alpha1$ and $\alpha2$ type, respectively. Human immunoglobulin molecules of a selected class or subclass may contain either a kappa ($\kappa$) or lambda ($\lambda$) light chain. See e.g., *Cellular and Molecular Immunology*, Wonsiewicz, M. J., Ed., Chapter 45, pp. 41–50, W. B. Saunders Co, Philadelphia, Pa. (1991); Nisonoff, A., *Introduction to Molecular Immunology*, 2nd Ed., Chapter 4, pp. 45–65, Sinauer Associates, Inc., Sunderland, Mass. (1984).

The term "humanized immunoglobulin" as used herein refers to an immunoglobulin comprising portions of immunoglobulins of different origin, wherein at least one portion is of human origin. For example, the humanized antibody can comprise portions derived from an immunoglobulin of nonhuman origin with the requisite specificity, such as a mouse, and from immunoglobulin sequences of human origin (e.g., chimeric immunoglobulin), joined together chemically by conventional techniques (e.g., synthetic) or prepared as a contituous polypeptide using genetic engineering techniques (e.g., DNA encoding the protein portions of the chimeric antibody can be expressed to produce a contiouous polypeptide chain). Another example of a humanized immunoglobulin of the claimed invention is an immunoglobulin containing one or more immunoglobulin chains comprising a CDR derived from an antibody of nonhuman origin and a framework region derived from a light and/or heavy chain of human origin (e.g., CDR-grafted antibodies with or without framework changes). Chimeric or CDR-grafted single chain antibodies are also encompassed by the term humanized immmunoglobulin. See, e.g., Cabilly et al., U.S. Pat. No. 4,816,567; Cabilly et al., European Patent No. 0,125,023 B1; Boss et al., U.S. Pat. No. 4,816,397; Boss et al., European Patent No. 0,120,694 B1; Neuberger, M.S. et al., WO 86/01533; Neuberger, M. S. et al., European Patent No. 0,194,276 B1; Winter, U.S. Pat. No. 5,225,539. Winter, European Patent No. 0,239,400 B1; Padlan, E.A. et al., European Patent Application No. 0,519,596 A1. See also, Ladner et al., U.S. Pat. No. 4,946,778; Huston, U.S. Pat. No. 5,476,786; and Bird, R. E. et al., Science, 242: 423–426 (1988)), regarding single chain antibodies.

The antigen binding region of the humanized immunoglobulin (e.g., the non-human portion) can be derived from an immunoglobulin of nonhuman origin, referred to as a donor immunogloblin, having specificity for hscdc6. For example, a suitable antigen binding region can be derived from the murine hCdc6-26, hCdc6-37, hCdc6-34, hCdc6-39, or hCdc6-41 monoclonal antibodies.

Additionally, other polyclonal or monoclonal antibodies, such as antibodies which bind to the same or similar epitope as the murine antibody, can be made (e.g., Kohler et al., Nature, 256:495–497 (1975); Harlow et al., 1988, Antibodies: A Laboratory Manual, (Cold Spring Harbor, N.Y.); and Current Protocols in Molecular Biology, Vol. 2 (Supplement 27, Summer 1994), Ausubel et al., Eds. (John Wiley & Sons: New York, N.Y.), Chapter 11 (1991), the teachings of which are incorporated by reference in their entirety). The epitopic specificity of a particular antibody can be determined by method known in the art. For example, Antibodies with an epitopic specificity which is the same as or similar to that of murine anti-cdc6 monoclonal antibodies of this invention can be identified by their ability to compete with murine monoclonal antibodies of this invention for binding to Cdc6 (e.g., to cells bearing human Cdc6, such as transfectants bearing Cdc6).

In one embodiment, the antigen binding region of the humanized immunoglobulin comprises a CDR of nonhuman origin. In this embodiment, the humanized immunoglobulin having binding specificity for hscdc6 comprises at least one CDR of nonhuman origin. For example, CDRs can be derived from the light and heavy chain variable regions of immunoglobulins of nonhuman origin, such that a humanized immunoglobulin includes substantially heavy chain CDR1, CDR2 and/or CDR3, and/or light chain CDR1, CDR2 and/or CDR3, from one or more immunoglobulins of nonhuman origin, and the resulting humanized immunoglobulin has binding specificity for hscdc6. All three CDRs of a selected chain can be substantially the same as the CDRs of the corresponding chain of a donor, and preferably, all three CDRs of the light and heavy chains are substantially the same as the CDRs of the corresponding donor chain.

The portion of the humanized immunoglobulin or immunoglobulin chain which is of human origin (the human portion) can be derived from any suitable human immunoglobulin or immunoglobulin chain. For example, a human constant region or portion thereof, if present, can be derived from the $\kappa$ or $\lambda$ light chains, and/or the $\gamma$ (e.g. $\gamma1$, $\gamma2$, $\gamma3$, $\gamma4$), $\mu$, $\alpha$ (e.g., $\alpha1$, $\alpha2$), $\delta$ or $\epsilon$ heavy chains of human antibodies, including allelic variants. A particular constant IgG2or IgF4, variants or portions thereof can be selected to tailor effector function. For example, a mutated constant region, also referred to as a "variant," can be incorporated into a fusion protein to minimize binding to Fc receptors and/or ability to fix complement (see e.g., Winter el al., U.S. Pat. Nos. 5,648,260 and 5,624,821; GB 2,209,757 B; Morrison et al., WO 89/07142; Morgan et al., WO 94/29351, Dec. 22, 1994).

If present, human framework regions are preferably derived from a human antibody variable region having sequence similarity to the analogous or equivalent region of the antigen binding region donor. Other sources of framework regions for portions of human origin of a humanized immunoglobulin include human variable consensus sequences (see, Kettleborough, C. A. et al., Protein Engineering 4:773–783 (1991); Carter et al., WO 94/04679, published Mar. 3, 1994)). For example, the sequence of the antibody or variable region used to obtain the nonhuman portion can be compared to human sequences as described in Kabat, E. A., et al., Sequences of Proteins of Immunological Interest, Fifth Edition, U.S. Department of Health and Human Services, U.S. Government Printing Office (1991).

In one embodiment, the humanized immunoglobulin comprises at least one of the framework regions (FR) derived from one or more chains of an antibody of human origin. Thus, the FR can include a FR1, FR2, FR3 and/or FR4 derived from one or more antibodies of human origin. Preferably, the human portion of a selected humanized chain includes FR1, FR2, FR3 and FR4 derived from a variable region of human origin (e.g., from a human immunoglobulin chain, from a human consensus sequence).

The immunoglobulin portions of nonhuman and human origin for use in the claimed invention have sequences that are identical to immunoglobulins or immunoglobulin portions from which they are derived, or variants thereof. Such variants include mutants differing by the addition, deletion, or substitution of one or more residues. As indicated above, the CDRs which are of nonhuman origin are substantially the same as in the nonhuman donor, and preferably are identical to the CDRs of the nonhuman donor. As described herein, changes in the framework region, such as those which substitute a residue of the framework region of human origin with a residue from the corresponding position of the donor can be made. One or more mutations in the framework region can be made, including deletions, insertions and substitutions of one or more amino acids. Foor a selected humanized antibody or chain, framework mutations can be designed, as described herein. Preferably, the humanized immunoglobulins can bind hscdc6 with an affinity similar to or better than that of the nonhuman donor. Variants can be produced by a variety of suitable methods, including mutagenesis of nonhuman donor or acceptor human chains.

The humanized immunoglobulins of the claimed invention have binding specificity for human hscdc6, and include humanized immunoglobulins (including fragments) which can bind determinants of the hscdc6 chains. In a preferred embodiment, the humanized immunoglobulin of the present invention has at least one functional characteristic of hCdc6-26, hCdc6-37, hCdc6-34, hCdc6-3 9, or hCdc6-41 murine antibody, such as binding function (e.g., having specificity for hscdc6, having the same or similar epitopic specificity), and/or inhibitory function.

Another aspect of the invention relates to a method of preparing a humanized immunoglobulin which has binding specificity for hscdc6. The humanized immunoglobulin can be obtained, for example, by the expression of one or more recombinant nucleic acids encoding a humanized immunoglobulin having binding specificity for hscdc6 in a suitable host cell.

Constructs or expression vectors suitable for the expression of a humanized immunoglobulin having binding specificity for hscdc6 are also provided. The constructs can be introduced into a suitable host cell, and cells which express a humanized immunoglobulin of the claimed invention, can be produced and maintained in culture. Suitable host cells can be procaryotic, including bacterial cells such as *E. coli, B. subtilis* and or other suitable bacteria, or eucaryotic, such as fungal or yeast cells (e.g., *Pichia pastoris*, Aspergillus species, *Saccharomyces cerevisiae, Schizosaccharomyces pombe, Neurospora crassa*), or other lower eucaryotic cells, and cells of higher eucaryotes such as those from insects (e.g., Sf9) insect cells (WO 94/26087, O'Connor, published Nov. 24, 1994)) or mammals (e.g., COS cells, NSO cells, SP2/0, Chinese hamster ovary cells (CHO), HuT 78 cells, 293 cells). (See, e.g., Ausubel, F. M. et al., eds. Current Protocols in Molecular Biology, Greene Publishing Associates and John Wiley & Sons Inc., (1993)).

Host cells which produce a humanized immunoglobulin having binding specificity for hscdc6 can be produced as follows. For example, a nucleic acid encoding all or part of the coding sequence for the desired humanized immunoglobulin can be inserted into a nucleic acid vector, e.g., a DNA vector, such as a plasmid, virus or other suitable replicon for expression. A variety of vectors are available, including vectors which are maintained in single copy or multiple copy, or which become integrated into the host cell chromosome.

Suitable expression vectors can contain a number of components, including, but not limited to one or more of the following: an origin of replication; a selectable marker gene; one or more expression control elements, such as a transcriptional control element (e.g., a promoter, an enhancer, terminator), and/or one or more translation signals; a signal sequence or leader sequence for membrane targeting or secretion. In a construct, a signal sequence can be provided by the vector or other source. For example, the transcriptional and/or translational signals of an immunoglobulin can be used to direct expression.

A promoter can be provided for expression in a suitable host cell. Promoters can be constitutive or inducible. For example, a promoter can be operably linked to a nucleic acid encoding a humanized immunoglobulin or immunoglobulin chain, such that it directs expression of the encoded polypeptide. A variety of suitable promoters for procaryotic (e.g., lac, tac, T3, T7 promoters for *E. coli*) and eucaryotic (e.g., yeast alcohol dehydrogenase (ADH1, SV40, CMV) hosts are available.

In addition, the expression vectors typically comprise a selectable marker for selection of host cells carrying the vector, and, in the case of replicable expression vector, an origin or replication. Genes encoding products which confer antibiotic or drug resistance are common selectable markers and may be used in procaryotic (e.g., lactamase gene (ampicillin resistance), Tet gene for tetracycline resistance) and eucaryotic cells (e.g., neomycin (G418 or geneticin), gpt (mycophenolic acid), ampicillin, or hygromycin resistance (genes). Dihydrofolate reductase marker genes permit selection with methotrexate in a variety of hosts. Genes encoding the gene product of auxotrophic markers of the host (e.g., LEU2, URA3, HIS3) are often used as selectable markers in yeast. Use of viral (e.g., baculovirus) or phage vectors, and vectors which are capable of integratiing into the genome of the host cell, such as retroviral vectors, are also contemplated. The claimed invention also relates to cells carrying these expression vectors.

For example, a nucleic acid (e.g., one or more nucleic acids) encoding the heavy and light chains of a humanized immunoglobulin having binding specificity for hscdc6, or a construct (e.g., one or more constructs) comprising such nucleic acid(s), can be introduced into a suitable host cell by a method appropriate to the host cell selected (e.g., transformation, transfection, electroporation, infection), such that the nucleic acid(s) are operably linked to one or more expression control elements (e.g., in a vector, in a construct created by processes in the cell, integrated into the host cell genome). Host cells can be maintained under conditions suitable for expression (e.g., in the presence of inducer, suitable media supplemented with appropriate salts, growth factors, antibiotic, nutritional supplements, etc.), whereby the encoded polypeptide(s) are produced. If desired, the encoded protein can be isolated from (e.g., the host cells, medium, milk). This process encompasses expression in a host cell of a transgenic animal (see e.g., WO 92/03918, GenPharm International, published Mar. 19, 1992).

In addition, functional fragments of antibodies, including fragments of chimeric, humanized, primatized, veneered or single chain antibodies, can also be produced. Functional fragments or portions of the foregoing antibodies include those which are reactive with hscdc6. For example, antibody fragments capable of binding to hscdc6 or portion thereof, including, but not limited to, Fv, Fab, Fab' and F(ab')$_2$ fragments are encompassed by the invention. Such fragments can be produced by enzymatic cleavage or by recombinant techniques. For instance, papain or pepsin cleavage can generate Fab or F(ab')$_2$ fragments, respectively. Antibodies can also be produced in a variety of truncated forms using antibody genes in which one or more stop codons has been introduced upstream of the natural stop site. For example, a chimeric gene encoding a F(ab')$_2$ heavy chain portion can be designed to include DNA sequences encoding the $CH_1$ domain and hinge region of the heavy chain.

It will be appreciated that the antibody can be modified, for example, by incorporation of or attachment (directly or indirectly (e.g., via a linker)) of a detectable label such as a radioisotope, spin label, antigen (e.g., epitope label such as a FLAG tag) or enzyme label, flourescent or chemiluminescent group and the like, and such modified forms are included within the term "antibody".

Characterization of hcdc6 and its Applications

As a result of work described herein, transcription of the Hscdc6 gene has been determined to be controlled by the E2F family of transcription factors. The promoter (1.5 kb) of the Hscdc6 gene was cloned and linked to a luciferase reporter gene. The pattern of expression of this promoter-:reporter construct following transfection into cultured cells (NIH 3T3 fibroblasts) is identical to the response of the endogenous gene during serum deprivation and stimulation. Two putative binding sites for E2F transcription factors were identified and mutated. Disruption of either site, alone or in combination, results in dysregulated expression. Specifically, promoter activity is dramatically up-regulated in serum-deprived cells where the endogenous gene is inactive. This result indicates that the Hscdc6 gene is under tight negative regulation in the G0 state by binding of members of the F2F family. Further, results from electrophoretic mobility shift assays suggest that E2F4 and E2F5 complexed with p130, a member of the Rb family of tumor suppressor genes, mediate this transcriptional repression of the Hscdc6 gene in growth arrested cells. The Hscdc6 gene is also under positive regulation by E2Fs, since forced expression of E2F1 activates transcription of Hscdc6.

These results are particularly significant in that they place Hscdc6 squarely at a downstream position in the major pathway controlling entry from G0 into the cell cycle and progression through G1 to S phase. This pathway includes cdk inhibitors of the p16and p21 families, cyclin D:cdk4 or cdk6, as well as members of the Rb and E2F families. Genes encoding proteins in this pathway are among those most frequently found to bear mutations in human tumors.

Thus, the Hscdc6 and Xcdc6 genes and peptides or proteins described herein permit the development of new biotechnological and pharmaceutical products to be used for the diagnosis and therapy of human cancers and other diseases associated with abnormal cellular proliferation. For example, the predicted role for Hscdc6 in the initiation of DNA replication, particularly the ability to control entry into both S phase and mitosis and to promote polyploidy when over-expressed, suggests that inherited or acquired mutations in the Hscdc6 protein, or in transcriptional control regions of the Hscdc6 gene that govern its expression, may contribute to the development of human cancers. Diagnostic tests which identify specific disease-related alleles or alteration of expression of the Hscdc6 gene in peripheral blood lymphocytes or in tumor material will improve the clinical management of patients at risk for the development of specific malignancies or of patients with established malignancies.

Disease-related alleles of Hscdc6 bearing specific DNA sequence alterations which are associated with particular conditions can be identified. As defined herein, "alteration" includes disruption of the gene (e.g., deletion of one or more nucleotides, addition of one or more nucleotides, or change in one or more nucleotides) and loss (deletion, either functional or physical) of the gence. The nucleotide sequences described herein, or their complements, are useful as hybridization probes or primers for an amplification method, such as polymerase chain reaction, to show the presence, absence or disruption of the genes of the present invention. Probes and primers can have all or a portion of the nucleic acid sequences of the genes described herein or all or a portion of their complements. The probes and primers call be any length, provided that they are of sufficient length and appropriate composition (i.e., appropriate nucleic acid sequence) to hybridize to all or an identifying or characteristic portion of the genes described herein or to a disrupted form of the genes, and remain hybridized under the conditions used.

Accordingly, by combining probes derived either from the isolated native sequence of the Hscdc6 gene or from the primers disclosed herein, with DNA from a sample obtained from an individual to be assessed, under conditions suitable for hybridization, it can be determined whether the sample from the individual contains the intact gene. Similarly, hybridization conditions can be selected such that the probes will hybridize only with altered DNA and not with unaltered (wild type or non-mutant) sequences; that is, the probes can be designed to recognize only particular alterations in the nucleic acid sequence of the gene, including addition of one or more nucleotides, deletion of one or more nucleotides or chance in one or more nucleotides (including substitution of one or more nucleotides for nucleotides normally present in the sequence).

Alternatively, disorders affecting, the peripheral blood lymphocytes or associated with tumors can result from altered expression of the genes described herein. For example, particular disorders may be associated with increased expression or decreased expression (including reduction of expression or complete absence) of the Hscdc6 gene relative to expression of Hscdc6 independent of the disorder. A different expression pattern, e.g., expression of Hscdc6 at times and/or locations at which Hscdc6 is not usually expressed or absence of Hscdc6 expression at times and/or locations at which expression usually occurs, can also be associated with proliferative disorders. A difference in expression patterns can be identified by quantitative and/or qualitative comparison of Hscdc6 expression in individuals having or suspected of having a disorder associated with altered expression patterns and in individuals not having the disorder. Such an analysis can include comparison of the levels of gene expression or the timing and/or location of gene expression.

These differences in Hscdc6 nucleotide sequence or expression patterns between individuals having or suspected of having a disorder and individuals not having the disorder are useful as the basis for a method of diagnosing or aiding in the diagnosis of conditions associated with proliferative disorders. This method can also be used to predict the likelihood that an individual is at increased risk for a particular condition associated with abnormal cell proliferation. The present method has utility with respect to conditions which involve abnormal cell division or proliferation, such as cancers, including tumors and blood-based abnormalities (e.g., leukemias) and conditions which involve polyploidy. The invention also relates to compositions (e.g., oligonucleotides, antibodies, small molecules, proteins and polypeptides) useful in the method.

Accordingly, the invention pertains to a method of diagnosing a condition associated with alteration of Hscdc6, comprising the steps of obtaining a DNA sample from an individual to be assessed, processing the DNA sample such that the DNA is available for hybridization; combining the processed DNA with nucleic acid sequences complementary to the nucleotide sequence of SEQ ID NO: 1, 5, 6, 7, 8, 9, 10, 11, 12, 13, 14, 15, 16, 17, 18, 19, 20, 21, 22, 23, 24, 25, or 26 under conditions appropriate for hybridization of the probes with complementary nucleic acid sequences in the DNA sample, thereby producing a combination; and detecting hybridization in the combination. Reduced hybridization (e.g., decrease in or absence of hybridization) in the combination, in comparison with an appropriate control sample, is indicative of a condition associated with alteration of Hscdc6.

Alternatively, the invention relates to a method of diagnosing a condition associated with alteration of Hscdc6. comprising, the steps of obtaining a DNA sample from an individual to be assessed; processing the DNA sample such that the DNA is available for hybridization; combining the processed DNA with nucleic acid sequences complementary to the nucleotide sequence of SEQ ID NO: 1, 5, 6, 7, 8, 9, 10, 11, 12, 13, 14, 15, 16, 17, 18, 19, 20, 21, 22, 23, 24, 25 or 26 under conditions appropriate for hybridization of the probes with altered complementary nucleic acid sequences in the DNA sample, but not with unaltered complementary nucleic acid sequences, thereby producing a combination; and detecting hybridization in the combination. Presence of hybridization (including increased hybridization in comparison with an appropriate control) in the combination is indicative of a condition associated with alteration of Hscdc6.

Forced expression in fungal cells of yeast proteins related to Hscdc6 and Xcdc6, such as cdc18, leads to DNA replication in the absence of mitosis, resulting in polyploidy. The development of polyploidy in human cells often represents a discrete step in the progression of benign or non-aggressive tumors into increasingly malignant forms. Thus, diagnostic tests to identify quantitative or qualitative abnormalities in Hscdc6 will aid clinicians in defining the prognosis and in tailoring the therapy for human cancer patients.

The claimed invention also relates to diagnostic assays for determining the presence or absence of hscdc6 and/or diagnosing or aiding in the diagnosis of a proliferative disorder. The methods involve determining the presence, absence or level of hscdc6, as compared to a control standard or baseline. The presence of hscdc6 indicates the presence of a proliferative disorder, whereas an absence of the hscdc6 protein indicates an absence of a proliferative disorder. Similarly, the level of hscdc6 can be quantified, and an increase of hscdc6, as compared with a control, standard or baseline, indicates the presence or a positive diagnosis of a proliferative disorder (e.g., cancer, such as cervical cancer or lymphoma). A decrease in hscdc6 indicates an absence of a proliferative disorder. Diagnostic assays for assaying hscdc6 include ELISAs, competition and sandwich ELISA assays, RIAs, or immunohistochemical immunofluorescence assays which involve utilize monoclonal antibodies having specificity for Hscdc6, as described herein. Also, any method known now of developed later can be used for measuring hscdc6.

A biological sample can be assayed for hscdc6 by combining the sample to be tested with an antibody having specificity for hscdc6, under conditions suitable for formation of a complex between antibody and hscdc6, and detecting or measuring (directly or indirectly) the formation of a complex. The sample can be obtained directly or indirectly (e.g., provided by a healthcare provider), and can be prepared by a method suitable for the particular sample (e.g., samples that contain tumor cells and/or tissue, such as from a biopsy, whole blood, aqueous blood components, plasma, serum) and assay format selected. Methods of combining sample and antibody and methods of detecting complex formation are also selected to be compatible with the assay format.

Antibodies can be labeled with a suitable label which can be detected directly, such as radioactive, fluorescent or chemiluminesent labels, or indirectly, such as enzyme labels or other antigenic or specific binding partners (e.g., biotin). Examples of such labels include, for example, fluorescent labels (e.g., fluorescein, rhodamine), chemiluminescent labels (e.g., luciferase), radioisotope labels (e.g, $^{32}$P, $^{125}$I, $^{131}$I), enzyme labels (e.g., horseradish peroxidase, alkaline phosphatase, β-galactosidase), biotin, avidin, spin labels and the like. The detection of antibodies in a complex can also be done immunologically with a second antibody which is then detected (e.g., indirectly detected). Conventional methods or other suitable methods can be used to directly or indirectly label an antibody.

In one embodiment, hscdc6 is determined using an ELISA assay (direct, indirect, competitive, or sandwich assays).

For detection of hscdc6 in a suitable sample, a sample is obtained from an individual. Samples can comprise any bodily fluid, cell or tissue that can possibly contain the hcdc6 protein. In particular, the sample can be tumor cells (e.g., obtained form a biopsy). Samples are prepared in a period of time suitable to maintain the integrity of the sample. Samples can be further processed as appropriate (e.g., by dilution with assay buffer (e.g., ELISA diluent)).

Accordingly, the present invention provides methods to determine the presence or absence of hscdc6 or methods for diagnosing, or aiding in the diagnosis of a proliferative disorder (e.g., proliferative disease) using an assay, such as an enzyme-linked immunosorbent assay, for measuring hscdc6 in a suitable sample. The ELISA involves indirect or direct detection of hscdc6 (e.g., antigen). The method comprises combining an anti-hscdc6 antibody such as hCdc6-26, hCdc6-37, hCdc6-34, hCdc6-39, and/or hCdc6-41 with a solid support that is coated with hscdc6 (e.g., control) or the sample to be tested. The anti-hscdc6 antibody can be conjugated with a detectable label (e.g., a detector antibody), or a detector antibody that can bind to the anti-hscdc6 antibody can be added. The method also utilizes competitive ELISAs and comprises combining a composition, that comprises an hscdc6-specific antibody with the sample to be tested, with hscdc6 coated solid support. If hscdc6 is present in the sample to be tested, it will compete with the hscdc6 coated on the solid support for binding with the anti-hscdc6 antibody. The antibody is conjugated with a detectable label and therefore can be detected (directly or indirectly detecting the hscdc6 in the sample). Various labels are known to those having skill in the art and are also described herein. Standard curves using known amounts of hscdc6 in the assays can be developed and then used to quantify an unknown amount of hscdc6 in a sample.

The methods described herein also utilize sandwich ELISAs. The method comprises combining a suitable sample, an anti-hscdc6 antibody as detector, and a solid support, having an anti-hscdc6 capture antibody bound (directly or indirectly) thereto. The detector antibody binds to a different hscdc6 epitope from that recognized by the capture antibody, under conditions suitable for the formation of a complex between the anti-hscdc6 antibodies and hscdc6. The formation of the complexes in the sample is determined using a detectable label, as described herein.

Detector antibodies can be a biotinylated anti-hscdc6 MAb and HRP-streptavidin, or HRP-conjugated anti-hscdc6 Mab. The antibodies can also be labeled with a fluorescent or radioactive label. The monoclonal antibodies that can be used as a detector or capture antibodies are hCdc6-26, hCdc6-37, hCdc6-34, hCdc6-39, and/or hCdc6-41.

The solid support (e.g., a microtiter plate, dipstick, bead, or other suitable support) can be coated directly or indirectly with an anti-hscdc6 antibody. For example, a microtiter plate can be coated with an anti-hscdc6 antibody, or a biotinylated anti-hscdc6 Mab can be added to a streptavidin coated support. A variety of solid supports and immobilizing or coating methods can be used, and can be selected according to the desired format.

In one embodiment, the sample (or a standard) is combined with the solid support simultaneously with the detector antibody, and optionally with a (i.e., one or more) reagent by which detector can be monitored. For example, the sample can be combined with the solid support simultaneously with labeled hscdc6 specific antibody.

A known amount of hscdc6 standard can be prepared and processed, as described above, for a suitable sample and used to quantify the amount of hscdc6 detected, permitting measurement of levels relative to a standard. The amount of hscdc6 in complexes can be determined by a variety of methods. For example, when HRP is used as a label, a suitable substrate such as OPD can be added to produce color intensity directly proportional to the bound anti-hscdc6 Mab (assessed e.g., by optical density), and therefore to the hscdc6 in the sample.

The amount of complex detected can be compared with a suitable control to determine if the levels are elevated. The sample to be tested can be compared with levels for the specific individual from previous time points (e.g., before having a proliferative disease, during various phases of treatment of the proliferative disease), or with levels in normal individuals or suitable controls. An individual who is being treated for a proliferative disorder can be monitored by determining the level of hscdc6 at various time points. For example, the level of hscdc6 can be determined before treatment, during treatment, and alter treatment. A decrease in hscdc6 indicates at least some success in treatment, whereas unchanged or all increase in hscdc6 levels indicates unsuccessful treatment, which allows a physician to modify the patient's treatment plan. For example, the assay can be performed using, a known amount of hscdc6 and a standard curved established. The amount of complex formed in a sample can then be determined relative to that produced by known amounts of hscdc6 standard.

The invention also embodies determining the presence, absence, or level of hscdc6 using RIAs. The concepts for performing, an ELISA are similar to that of an RIA. For example, a sample can be contacted with all antibody having specificity for hscdc6 under conditions suitable for formation of a complex between antibody and hscdc6 in the sample, and detecting or measuring (directly or indirectly) the formation of a complex using a radioisotope-conjugated immunobinding assay.

For example, hscdc6 can be assessed by an immunobinding assay comprising obtaining a sample samples with a composition comprising an anti-hscdc6 antibody, (e.g., an anti-hscdc6 antibody comprising a radioactive label; or an anti-hscdc6 antibody comprising a binding site for a second antibody which comprises a radioactive label), preferably in an amount in excess of that required to bind the hscdc6 in the sample under conditions suitable for the formation of labeled complexes between said anti-hscdc6 antibody and any hscdc6 present in the sample. This assay can use any hscdc6 antibody, including hCdc6-26, hCdc6-37 hCdc6-34, hCdc6-39, and hCdc6-41. The method also involves determining (detecting or measuring) the formation of complex in the sample. The level of hscdc6 in the sample is proportional to the amount of radioactivity detected, which can be compared with a standard, as described herein.

The invention also pertains to determining the absence, presence or level of hscdc6 by utilizing an apparatus. In utilizing an apparatus to measure hscdc6, the antibody detection concepts used in the ELISA, immunofluorescence or RIA, as described herein apply. The above ELISA methods described can be adapted so that the support surface and method of detection utilized is suitable for measurement with an apparatus. Adapting an apparatus to measure hscdc6 can be done using routine methods known in the art. Such methods involve re-programming the machine to use a standard suitable for measuring hscdc6, anti-hscdc6 detector and/or capture antibodies.

The invention also relates to a method for determining the presence of a proliferative disorder, or for diagnosing or aiding in the diagnosis of a proliferative disorder, comprising determining the level of at least two markers for a proliferative disorder in a sample from an individual, wherein one of the markers is hscdc6. The other maker can be any marker for proliferative disease including proteins from the MCM (Mini-Chromosome Maintenance) family, such as MCM-2, MCM-3, MCM-4, MCM-5, MCM-6 and MCM-7. Screening for additional markers increases the diagnostic accuracy and/or reliability. The screening of the additional marker can be done using the methods described herein.

Hscdc6 also has potential as a target for drug- or gene-based therapies designed to slow the growth or promote destruction of human tumor cells. Therapeutic compositions can be targeted or delivered to appropriate cells in an individual utilizing a variety of known delivery or targeting vehicles, including but not limited to antibodies and liposomal compositions. The knowledge of the amino acid sequence of Hscdc6 proteins permits the identification of drugs that inhibit the function of Hscdc6, thereby blocking DNA replication and stopping the growth of human tumors. Inhibition of Hscdc6 would also drive cells with unreplicated DNA into mitosis, thereby causing cell death. This mechanism of action is unique and unlike that of drugs currently used to treat human cancers. Inhibitors of Hscdc6 function will block DNA replication at a step downstream of pathways triggered by growth factors, kinase cascades and proteins acting to regulate the cell cycle.

Accordingly, this invention pertains to a method of treating a tumor in an individual comprising administering an antagonist of Hscdc6 to an individual in a manner such that the antagonist enters the tumor cells. The antagonist inhibits the activity of the Hscdc6 gene or protein and causes at least one of two possible results: inhibition of tumor cell DNA replication, with concomitant inhibition of tumor growth, and mitotic division of tumor cells with unreplicated DNA, resulting in tumor cell death. As used herein, inhibition of tumor cell DNA replication includes decreasing the rate or frequency of DNA replication as well as completely preventing DNA replication. Also, as defined herein, inhibition of tumor growth, which results from tumor cell death, includes slowing the growth of the subject tumor, stopping the growth of the tumor and decreasing the size of the tumor. Antagonists of Hscdc6 include compositions which block or inhibit the function or activity of Hscdc6 or which decrease the expression or enhance or increase the down-regulation of Hscdc6, both at the DNA or RNA (nucleic acid) and protein (amino acid) levels. For instance, agonists of Hscdc6 include but are not limited to cyclin-dependent kinases, mitotic cyclins and Hscdc6 antisense molecules.

In particular, antagonists to hscd6 include a murine anti-human monoclonal antibody, humanized and/or chimeric antibodies, as described herein. Accordingly, the invention embodies compositions for treating a proliferative disease or disorder (e.g., a form of cancer) comprising an immunoglobulin having an antigen binding region that is specific to hscdc6. The antigen binding region can be derived from the antigen binding regions of the hCdc6-26, hCdc6-37, hCdc6-34, hCdc6-39, and hCdc6-41. Therapeutically effective amounts, dosages and modes of administration are known in the art and described herein.

In addition, drugs or gene therapies that stabilize Hscdc6 or augment its function in the G2 and M phases of the cell cycle will block mitosis, even though DNA replication continues. Programmed cell death is a likely consequence of a Hscdc6-induced block to mitosis, and will inhibit tumor growth or promote tumor regression. Thus, drugs or gene-based therapies designed either to block the function of Hscdc6 or to augment its function have application to the therapy of human cancers. For example, the present invention pertains to a method of treating a tumor in an individual comprising administering Hscdc6 or an agonist of Hscdc6 to a the individual in such a manner that the Hscdc6 or Hscdc6 agonist centers the tumor cells. Introduction of Hscdc6 or and agonist of Hscdc6 to a cell in the G2 or M phase of the cell cycle prevents entry of the cell into mitosis and thus causes tumor cell death. As used herein, the term "agonist" of Hscdc6 is intended to mean a composition which mimics or enhances the function or activity of Hscdc6 or which prevents or inhibits the down-regulation or decrease in expression of Hscdc6, both at the DNA or RNA (nucleic acid) and protein (amino acid) levels. For instance, agonists of Hscdc6 include cyclin-dependent kinase inhibitors. Prevention of cellular mitosis results in tumor cell death and inhibition of tumor growth.

In this context, drugs designed on the basis of the Hscdc6 protein sequence and intended for use in humans include small non-peptide molecules, peptides or proteins related to Hscdc6 or designed to alter the function of endogenous Hscdc6, or DNA or RNA sequences encoding proteins or peptides related to Hscdc6 or designed to alter the function of endogenous Hscdc6.

In a similar manner, knowledge of the Hscdc6 gene sequence can be used to develop novel methods and products for blocking cell proliferation in disorders other than cancer, including but not limited to, atherosclerosis vascular disease, vascular restenosis following medical or surgical reperfusion procedures, psoriasis, inflammatory arthritis and other inflammatory diseases, autoimmune diseases, and rejection of transplanted organs. Accordingly, the present invention provides a method of inhibiting undesirable cell proliferation in an individual comprising administering an agonist or antagonist of Hscdc6 to the individual in such a manner that the agonist or antagonist enters the cells in which it is desirable to inhibit proliferation. An antagonist of Hscdc6 will prevent or reduce the activity of Hscdc6, and thereby prevent the replication of cellular DNA; cells with unreplicated DNA will enter mitosis and cell death will result. An agonist of Hscdc6 will prolong or increase the effects of Hscdc6, resulting in polyploidy and preventing mitosis; cells which are affected in this manner will undergo programmed cell death, inhibiting DNA replication and normal entry of the cell into mitosis, resulting in cell death.

In addition, the ability of Hscdc6 to initiate DNA replication can be exploited for the development of novel products to enhance cell proliferation for therapy of conditions associated with loss of viable tissue in an individual, including but not limited to, traumatic injury, myocardial infarction, cardiomyopathy, renal failure, hepatic failure and stroke. For example, this invention provides a method of enhancing cell proliferation for therapy of a condition associated with loss of viable tissue in an individual comprising administering Hscdc6 or an agonist of Hscdc6 to an individual such that it enters cells in the individual. The activity of Hscdc6 or an Hscdc6 agonist causes initiation of DNA replication in the cell and entry of the cell into mitosis. Administration of Hscdc6 or an Hscdc6 agonist can supplement, enhance or replace the natural-occurring levels of Hscdc6 and enhance cell proliferation.

Accordingly, the present invention also pertains to pharmaceutical compositions comprising a gene encoding a polypeptide or protein which functions in the regulation of DNA replication or entry of a cell into mitosis, or proteins or polypeptides encoded thereby, particularly an Hscdc6 protein or an Xcdc6 polypeptide. For instance, compositions of the present invention call be formulated with a physiologically acceptable medium to prepare a pharmaceutical composition. The particular physiological medium may include but is not limited to, water, buffered saline, polyols (e.g., glycerol, propylene glycol, liquid polyethylene glycol) and dextrose solutions. The optimum concentration of the active ingredient(s) in the chosen medium can be determined empirically, according to procedures well known to medicinal chemists, and will depend on the ultimate pharmaceutical formulation desired. Methods of introduction of exogenous Hscdc6 or Xcdc6 polypeptides at the site of treatment include, but are not limited to, intradermal, intramuscular, intraperitoneal, intravenous, subcutaneous, oral and intranasal. Other suitable methods of introduction can also include rechargeable or biodegradable devices and slow release polymeric devices. Also encompassed by the present invention are pharmaceutical compositions comprising an agonist or antagonist of Hscdc6 or Xcdc6, including oligonucleotides, polypeptides, proteins and small molecules. The pharmaceutical compositions of this invention can also be administered as part of a combinatorial therapy with other agents.

The invention further pertains to kits for detecting (e.g., determining or measuring) the presence of hscdc6 in a sample. The kit comprises an antibody or functional portion thereof which binds to hscdc6, and one or more ancillary reagents that are suitable for detecting the presence of a complex between the antibody and hscdc6, as described herein. In particular, they following monoclonal antibodies can be used: hCdc6-26, hCdc6-37, hcdc6-34, hCdc6-39, and/or hCdc6-41. The kit can further comprise one or more reagents for detecting another marker, a marker that is not hscdc6. Such markers include MCM proteins, as described herein. The reagents can be used for carrying out an ELISA, an immunoflorescence assay or a RIA, for example, detectable labels, additional antibodies with detectable labels, as described herein.

The invention also includes kits for diagnosing a proliferative disease or determining the presence or absence of a proliferative disease comprising one or more reagents for detecting the level of hscdc6 in a patient sample (e.g., one or more reagents for carrying out an ELISA assay or RIA). These reagents include antibodies specific to hscdc6, such as the hCdc6-26, hCdc6-37, hCdc6-34, hCdc6-39, and/or hCdc6-41 monoclonal antibodies. The kit can also comprise detectably labeled antibodies or regents for conjugating the antibody to a detectable label, as described herein. The kit further comprises one or more reagents for detecting additional markers for proliferative diseases and/or a control.

The examples provided herein are offered for the purpose of illustrating the present invention only and are not to be construed to limit the scope of this invention. The teachings of all references cited herein are incorporated herein by reference.

EXEMPLIFICATION

Methods and Materials

Cells and Tissue Culture

Cell lines HeLa (human cervix carcinomait), 293 (adenovirus-transformed embryonal human kidney fibroblasts), MANCA (human B-cell lymphoma), Raji (human Burkitt lymphoma), IMR90 (human fetal lung fibroblasts), Vero (african green monkey kidney fibroblasts) and Cos-1 (SV40-transformed african green monkey kidney) were obtained from the Cold Sprinig Harbor Laboratory cell culture facility or the American Type Culture Collection. The cells were either grown in Dulbecco's modified Eagle's medium (DMEM) or in RPMI-1640 medium both supplemented with 10% calf serum and antibiotics (30 mg/liter penicillin, 50 mg/liter streptomycin sulfate). All cultures were kept at 37° C. and 7% $CO_2$, and routinely screened for mycoplasma.

Antibodies

To generate monoclonal antibodies anti-human Cdc6, full length human Cdc6 was overexpressed in *E. coli* and purified as a GST-fusion protein. After cleavage of the GST moiety, Cdc6 was further purified in a PREP CELL gel (BioRad) and used as immunogen. Standard techniques for mice immunization, analysis of test bleeds, generation of hybridoma cell lines and production and production fluid were used. Harlow and Lane, *Antibodies: A Laboratory Manual*, Cold Spring Harbor Laboratory Press (1988). Two of the monoclonal antibodies generated (hCdc6-26 and hCdc6-37) have been characterized in this work. Polyclonal antibodies anti-hOrc2 and anti-hCdc6 have been described before. Gavin et al., *Science* 270:1667–1671 (1995); Williams et al., *PNAS* 95:3603–3608, (1997). Polyclonal antibodies anti-hMcm3 and anti-hMcm5 were gifts from Dr. H. Nojima (Osaka University, Japan), and Dr. R. Knippers (University of Konstanz, Germany). Anti-pRb, C-15, was obtained from St. Cruz.

Flow Cytometry and Centrifugal Elutriation

For cytofluorometric analyses cells were harvested and fixed by rapid submersion in 1 ml of ice-cold 85% ethanol. Alter at least 1 hour fixation at 4° C., cells were pelleted and stained in 0.5 ml staining solution (0.25 mg/ml propidium iodide, 0.05 mg/ml RNAse, 1% $NaN_3$ in 1×PBS). Stained cells were analyzed on a Becton-Dickinson FACSCAN machine and the percentage of cells in each phase of the cell cycle was estimated with the CELLFIT computer program. Separation of logarithmically growing cells into distinct cell cycle phases was accomplished by centrifugal elutriation in a Beckman centrifuge and a JE-6B rotor with a standard separation chamber. The rotor was kept at a speed of 1400 rpm, temperature was 4° C., and medium flow was controlled with a Cole-Parmer MASTERFLEX pump. Consecutive fractions of 200–250 ml were collected at increasing flow rates. Hengstschläger et al., *Biotechniques* 23:232–237 (1997). Cytofluorometric analyses of cell cycle distributions were performed as described herein.

Immunoblot and Northern Blot Analysis

Total cell protein extracts were prepared by lysis with NP40buffer, and immunoblots were carried out, as indicated in Harlow and Lane *Antibodies: A Laboratory Manual*, Cold Spring Harbor Laboratory (1988). Multiple Tissue Northern blots (Human-1 and Human-2) were purchased from CLONTECH Laboratories, Inc. DNA fragments of 706, 640, 809 bp corresponding to parts of hCDC6, hORC1, hORC2 open reading frames, respectively, were labeled with $\alpha(^{32}P)ATP$ by random-priming (average specific activity of the labeled probes: $2\times10^6$ cpm/ml). Northern blots were performed using EXPREESSHYB hybridization solution (CLONTECH) Laboratories, Inc. following the mannufacturer's instructions.

Chromatin Isolation

Figure 9:
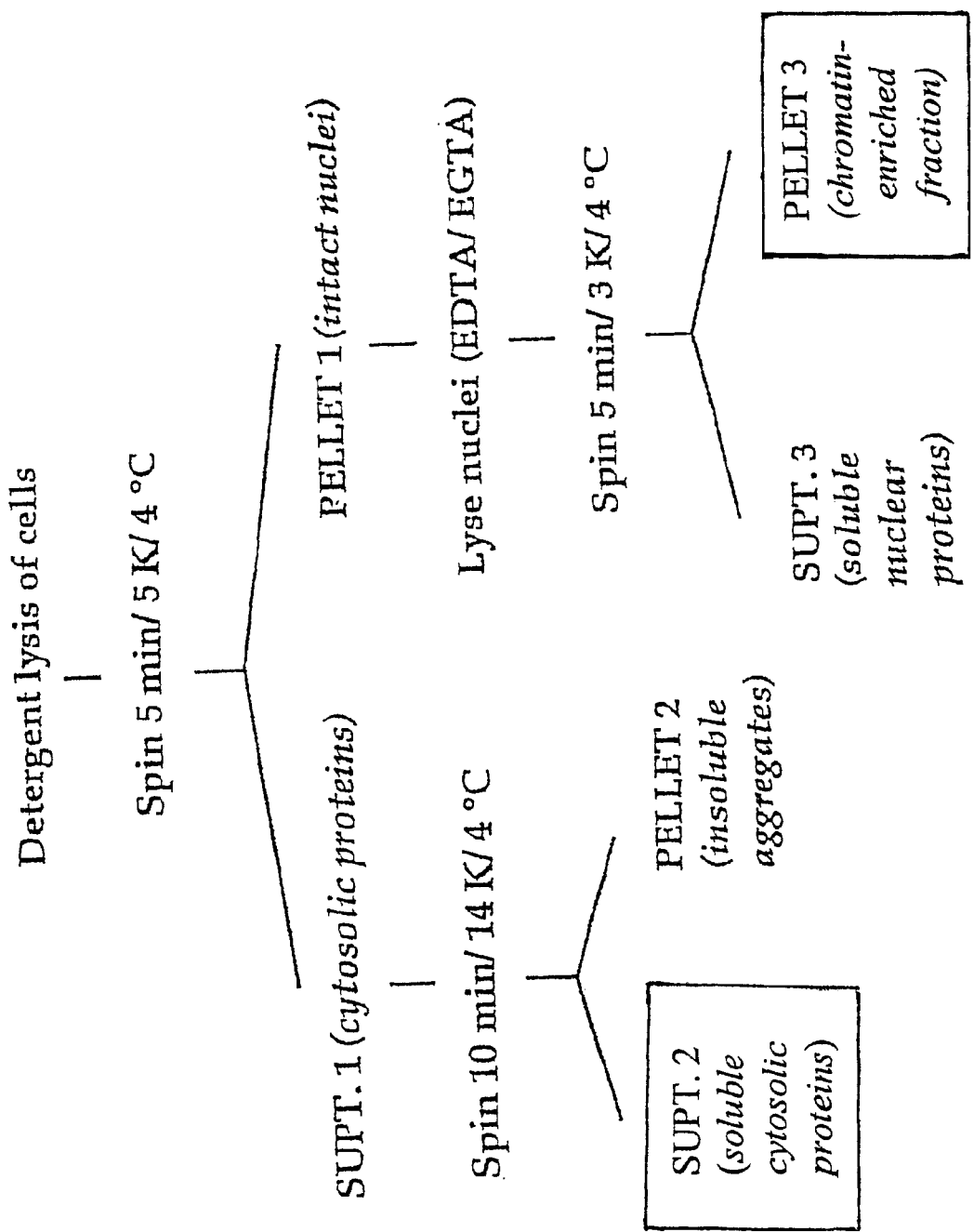
FIG. 9 shows a scheme of the chromatin isolation protocol from tissue cultured cells. Raji cells at different points in the cell cycle were isolated by centrifugal elutriation, and DNA content was analyzed by flow cytometry. $10^7$ cells in each fraction were subjected to the biochemical fractionation. Immunoblots were done in the soluble protein fraction (supernatant 2) and the chromatin-enriched fraction (pellet 3). Cdc6 immunuoblots were done with hCdc6-37 at a 1:100 dilution.

Cells were resuspended ($4\times10^7$ cells/ml) in buffer A (10 mM Hepes, pH 7.9, 10 mM KCl, 1.5 mM $MgCl_2$, 0.34 M sucrose, 10% glycerol, 1 mM DTT, 5 µg/ml aprotinin, 5 µg/ml leupeptin, 0.5 µg/ml pepstatin A, 0.1 mM PMSF). 0.1% Triton X-100 was added and the cells were incubated for 5 min on ice. Nuclei were collected by low-speed centrifugation (4 min/3500 rpmn/4° C.). The supernatant was further clarified by high-speed centrifugation (15 min/14000 rpm/4° C.). Nuclei were washed once in buffer A, and then lysed in buffer B (3 mM EDTA, 0.2 mM EGTA, 1 mM DTT, protease inhibitors as above). Insoluble chromatin was collected by centrifugation (5 min/4000 rpm/4° C.), washed once in buffer B, and centrifuged again under the same conditions. The final chromatin pellet was resuspended in Laemmli buffer and sonicated for 15 seconds in a Tekmar CV26 sonicator using a microtip at 25% amplitude (see scheme in FIG. 9).

Results

Hscdc6 is Over-Expressed in Tumor-Derived Cells

To study the regulation of Cdc6 in mammalian cells, monoclonal antibodies against full-length recombinant human Cdc6 were raised. Monoclonal antibodies hCdc6-26 and hCdc6-37 both recognized a protein of approximately 62 kDa in total protein extracts from human cells. The titer of hCdc6-26 was significantly higher than that of anti-hCdc6-37, although hCdc6-26 crossreacted with another protein of mass slightly above 31 kDa. In any case, the specificity of both hCdc6-26 and hCdc6-37 in immunoblots was much better than that of an anti-hCdc6 polyclonal serum. The specificity of the new antibodies was further demonstrated by blotting recombinant human Cdc6 protein purified from *E. coli* or expressed in insect cells using a baculovirus vector. These antibodies also recognized a 62 kDa protein from human cells after immunoprecipitation with an anti-hCdc6 polyclonal antibody. In the course of this study, the new monoclonal antibodies were shown to specifically react with Cdc6 of human, monkey and rat origin by immunoblotting. When both antibodies were tested in a panel of different proliferating cell types, a protein of 62 Kda was detected in most of the cell lines tested. Interestingly, transformed or tumor-derived cells, such as HeLa, 293, MANCA, Raji, or Cos-1, exhibited significantly more Cdc6 than primary, diploid cells such as IMR90 or Vero. These differences were particularly evident with antibody hCdc6-37. Interestingly, Mcm protein levels were also much lower in IMR90 as compared to transformed or tumor-derived cells.

To explore the expression of Cdc6 throughout the cell cycle, logarithmically growing MANCA cells were separated according to cell size by centrifugal elutriation. The advantage of this synchronization procedure is that cells which have never been forced to leave the cell cycle are separated without the use of drugs. The DNA content of each elutriated fraction was determined by staining with propidium iodide and the percentage of cells in each phase of the cell cycle was calculated. Western blot analyses demonstrated Cdc6 to be absent in the first two elutriated fractions (corresponding to small, early G1 cells) and to be induced in early/mid G1, before cyclin A expression and hyperphosphorylation of the retinoblastoma (Rb) protein. In contrast, levels of other proteins involved in initiation of replication such as Orc2, Mcm3 and Mem5, did not fluctuate in the cell cycle. Similar results have been obtained after ejutriation of 293 cells. These data demonstrate that the levels of Cdc6 protein vary throughout the mammalian cell cycle. hCdc6 levels are constant across the cell cycle.

Association of Cdc6 and Mcm3 with Chromation is Cell Cycle Regulated

A new, simple chromatin-binding assay was developed to investigate the association of mammalian replication proteins with chromatin during the cell cycle. (FIG. 9) In brief, cells were lysed with Triton X-100 in a buffer containing 1.5 mM $MgCl_2$ and 0.34 M sucrose. Intact nuclei were collected at low speed, washed and lysed for 30 min in a buffer containing EDTA and EGTA. A second centrifugation step separated soluble nuclear proteins from an insoluble fraction. Proteins found in this final pellet fraction were likely to be bound to chromatin or the nuclear matrix. Indeed, DNA and histones were quantitatively recovered in the final chromatin-enriched fraction, and histones were readily solubilized by treatment with micrococcal nuclease.

To study the cell cycle regulation of chromatin binding of the replication initiation proteins, logarithmically growing Raji cells or MANCA cells were elutriated and the obtained fractions were subjected to the described biochemical fractionation. Both pellet 3 (chromatin-enriched fraction) and supernatant 2 (enriched in soluble proteins) were tested for the presence of replication proteins. Orc2 was found to be associated with chromatin throughout the entire cell cycle (only a much longer exposure of the blots revealed a minimum amount of soluble Orc2). Cdc6 was also targeted to chromatin during most of the cell cycle, although the amount bound increased in late G1 or early S phase. Although at a very low level, some Cdc6 was detected on chromatin even in the first elutriated fraction. This could be explained by the presence of mid- or late G1 cells in this fraction (in this experiment, G1 cells were collected in only two fractions, as opposed to four fractions). Cdc6 was also detected in soluble foil during S and G2/M phases: this free Cdc6 could have been shuffled from the nucleus to the cytosol after G1/S transition. Finally, while all excess of soluble Mem3 and Mcm5 was detected at roughly constant levels across the cell cycle, a fraction of each Mcm protein was bound to chromatin in G1, but both Mcm proteins were released from chromatin as S phase progressed. This observation perfectly matches the expected dynamics of chromatin association for human MCMs and supports the validity of the biochemical fractionation protocol that was used to evaluate association of proteins with chromatin.

Figure 10:
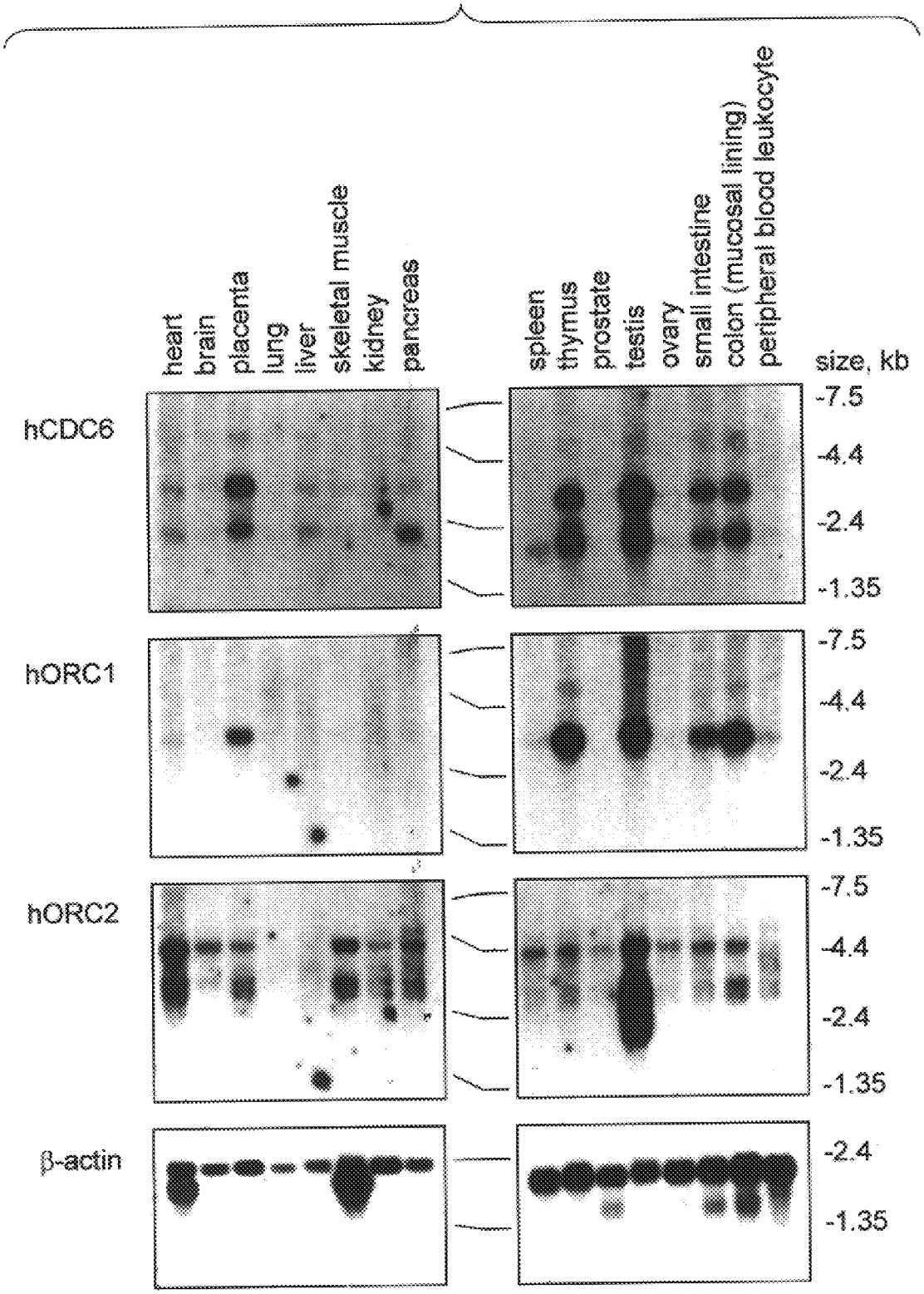
FIG. 10 shows the expression of CDC6, ORC1and ORC2 in different human tissues. Human-1 and Human-2 MTN filters were purchased from ClonTech. Each lane contains approximately 2 mg of poly(A)$^+$ RNA isolated from the indicated tissue. Northern blot analysis of CDC6 results in two major bands that could represent two different spliced forms of the gene.

CDC6 and ORC1 Genes are Preferentially Expressed in Tissues with Active Proliferating Cells To analyze the potential Cdc6 to act as a cell proliferation marker, the relative expression of the CDC6 gene, along with other genes encoding known initiator proteins were evaluated by Northern blot in different human tissues (FIG. 10). The initiator proteins were hORC1 and hORC2, the two largest subunits of the human origin recognition complex. CDC6 and ORC1 showed a remarkably similar pattern of expression, being most abundant in placenta, thymus, testis, small intestine and the mucosal lining of the colon, tissues containing active, proliferating cells. On the other hand, expression of CDC6 and ORC1 was lower, or null, in tissues abundant in nonproliferating, differentiated cells, such as hearts brain lung, liver, skeletal muscle, kidney, pancreas, spleen, prostate, ovary and peripheral blood leukocyte. Interestingly, ORC2 was expressed more evenly, with the exception of lung, liver and perypheral blood leukocytes, in which it was not detected. Expression of β-actin was monitored as a control of poly(A)+RNA loading, in the blots.

While this invention has been particularly shown and described with references to preferred embodiments thereof, it will be understood by those skilled in the art that various changes in form and details may be made therein without departing from the spirit and scope of the invention as detined by the appended claims.

We claim:

1. A method for determining the presence or absence of Human Cell Division Cycle-6 protein (hscdc6) in a sample, comprising combining a sample to be tested with an antibody having specificity for hscdc6, under conditions suitable for formation of a complex between said antibody and hscdc6, and detecting or measuring the formation of said complex, wherein the antibody is selected from the group consisting of: hCdc6-26, hCdc6-37, hCdc6-34, hCdc6-39, and hCdc6-41.

2. The method of claim 1, wherein the antibody is labeled.

3. The method of claim 2, wherein the label is a radioactive label, a fluorescent label, a chemiluminescent label, or an enzyme label.

4. The method of claim 2, wherein the formation of complex is detected or measured using a second antibody comprising a detectable label.

5. A method of determining the presence or absence of a proliferative disorder, comprising determining the level of at least two markers for the proliferative disorder in a sample from an individual, wherein one of the markers is hscdc6, and wherein an elevated level of hscdc6 and at least one other marker, as compared to a control, indicates the presence of a proliferative disorder, wherein the level of hscdc6 is determined by an antibody specific for hscdc6 selected from a group consisting of: hCdc6-26, hCdc6-37, hCdc6-34, hCdc6-39, and hCdc6-41.

6. The method of claim 5, wherein the second marker is a DNA replication protein, an ORC family protein, a cell cycle regulatory protein, or a MCM protein.

7. The method of claim 5, wherein the antibody is labeled.

8. The method of claim 7, wherein the label is a radioactive label, a fluorescent label, a chemiluminescent label, or an enzyme label.

9. A method for determining the presence or absence of a proliferative disorder, comprising determining the level of hscdc6 in a sample from an individual, wherein an elevated level of hscdc6, as compared to a control, indicates the presence of a proliferative disorder, wherein the level of hscdc6 is determined by an antibody specific for hscdc6 selected from a group consisting of: hCdc6-26, hCdc6-37, hCdc6-34, hCdc6-39, and hCdc6-41.

10. A method for diagnosing or aiding in the diagnosis of a proliferative disorder, comprising determining the presence, absence or level of hscdc6 in a sample from an individual, wherein the presence or increased level of hscdc6 indicates a positive diagnosis, and the level of hscdc6 is determined by an antibody specific for hscdc6 selected from a group consisting of: hCdc6-26, hCdc6-37, hCdc6-34, hCdc6-39, and hCdc6-41.

11. The method of claim 10, wherein the antibody is labeled.

12. The method of claim 11, wherein the label is a radioactive label, a fluorescent label, a chemilumineseent label, or an enzyme label.

* * * * *

UNITED STATES PATENT AND TRADEMARK OFFICE
CERTIFICATE OF CORRECTION

PATENT NO.   : 6,361,954 B1
DATED        : March 26, 2002
INVENTOR(S)  : Bruce Stillman, R. Sanders Williams and Juan Mendez It is certified that error appears in the above-identified patent and that said Letters Patent is hereby corrected as shown below:

<u>Column 76,</u>
Line 4, delete "chemilumineseent" and insert therefor -- chemiluminescent --.

Signed and Sealed this

Eighteenth Day of June, 2002

Attest:

Attesting Officer

JAMES E. ROGAN
*Director of the United States Patent and Trademark Office*

SEQUENCE LISTING

<160> NUMBER OF SEQ ID NOS: 50

<210> SEQ ID NO 1
<211> LENGTH: 2653
<212> TYPE: DNA
<213> ORGANISM: H. sapiens
<220> FEATURE:
<221> NAME/KEY: CDS
<222> LOCATION: (211)...(1893)

<400> SEQUENCE: 1

```
gagcgcggct ggagtttgct gctgccgctg tgcagtttgt tcaggggctt gtggcggtga      60
gtccgagagg ctgcgtgtga gagacgtgag aaggatcctg cactgaggag gtggaaagaa     120
gaggattgct cgaggaggcc tggggtctgt gagacagcgc agctgggtga aggctgcggg     180
ttccggcgag gcctgagctg tgctgtcgtc atg cct caa acc cga tcc cag gca     234
                                  Met Pro Gln Thr Arg Ser Gln Ala
```

-continued

```
                    1                           5
cag gct aca atc agt ttt cca aaa agg aag ctg tct cgg gca ttg aac        282
Gln Ala Thr Ile Ser Phe Pro Lys Arg Lys Leu Ser Arg Ala Leu Asn
     10              15              20 aaa gct aaa aac tcc agt gat gcc aaa cta gaa cca aca aat gtc caa        330
Lys Ala Lys Asn Ser Ser Asp Ala Lys Leu Glu Pro Thr Asn Val Gln
 25              30              35              40 acc gta acc tgt tct cct cgt gta aaa gcc ctg cct ctc agc ccc agg        378
Thr Val Thr Cys Ser Pro Arg Val Lys Ala Leu Pro Leu Ser Pro Arg
             45              50              55 aaa cgt ctg ggc gat gac aac cta tgc aac act ccc cat tta cct cct        426
Lys Arg Leu Gly Asp Asp Asn Leu Cys Asn Thr Pro His Leu Pro Pro
         60              65              70 tgt tct cca cca aag caa ggc aag aaa gag aat ggt ccc cct cac tca        474
Cys Ser Pro Pro Lys Gln Gly Lys Lys Glu Asn Gly Pro Pro His Ser
     75              80              85 cat aca ctt aag gga cga aga ttg gta ttt gac aat cag ctg aca att        522
His Thr Leu Lys Gly Arg Arg Leu Val Phe Asp Asn Gln Leu Thr Ile
 90              95             100 aag tct cct agc aaa aga gaa cta gcc aaa gtt cac caa aac aaa ata        570
Lys Ser Pro Ser Lys Arg Glu Leu Ala Lys Val His Gln Asn Lys Ile
105             110             115             120 ctt tct tca gtt aga aaa agt caa gag atc aca aca aat tct gag cag        618
Leu Ser Ser Val Arg Lys Ser Gln Glu Ile Thr Thr Asn Ser Glu Gln
            125             130             135 aga tgt cca ctg aag aaa gaa tct gca tgt gtg aga cta ttc aag caa        666
Arg Cys Pro Leu Lys Lys Glu Ser Ala Cys Val Arg Leu Phe Lys Gln
        140             145             150 gaa ggc act tgc tac cag caa gca aag ctg gtc ctg aac aca gct gtc        714
Glu Gly Thr Cys Tyr Gln Gln Ala Lys Leu Val Leu Asn Thr Ala Val
    155             160             165 cca gat cgg ctg cct gcc agg gaa agg gag atg gat gtc atc agg aat        762
Pro Asp Arg Leu Pro Ala Arg Glu Arg Glu Met Asp Val Ile Arg Asn
    170             175             180 ttc ttg agg gaa cac atc tgt ggg aaa aaa gct gga agc ctt tac ctt        810
Phe Leu Arg Glu His Ile Cys Gly Lys Lys Ala Gly Ser Leu Tyr Leu
185             190             195             200 tct ggt gct cct gga act gga aaa act gcc tgc tta agc cgg att ctg        858
Ser Gly Ala Pro Gly Thr Gly Lys Thr Ala Cys Leu Ser Arg Ile Leu
            205             210             215 caa gac ctc aag aag gaa ctg aaa ggc ttt aaa act atc atg ctg aat        906
Gln Asp Leu Lys Lys Glu Leu Lys Gly Phe Lys Thr Ile Met Leu Asn
        220             225             230 tgc atg tcc ttg agg act gcc cag gct gta ttc cca gct att gct cag        954
Cys Met Ser Leu Arg Thr Ala Gln Ala Val Phe Pro Ala Ile Ala Gln
    235             240             245 gag att tgt cag gaa gag gta tcc agg cca gct ggg aag gac atg atg       1002
Glu Ile Cys Gln Glu Glu Val Ser Arg Pro Ala Gly Lys Asp Met Met
    250             255             260 agg aaa ttg gaa aaa cat atg act gca gag aag ggc ccc atg att gtg       1050
Arg Lys Leu Glu Lys His Met Thr Ala Glu Lys Gly Pro Met Ile Val
265             270             275             280 ttg gta ttg gac gag atg gat caa ctg gac agc aaa ggc cag gat gta       1098
Leu Val Leu Asp Glu Met Asp Gln Leu Asp Ser Lys Gly Gln Asp Val
            285             290             295 ttg tac acg cta ttt gaa tgg cca tgg cta agc aat tct cac ttg gtg       1146
Leu Tyr Thr Leu Phe Glu Trp Pro Trp Leu Ser Asn Ser His Leu Val
        300             305             310 ctg att ggt att gct aat acc ctg gat ctc aca gat aga att cta cct       1194
```

```
Leu Ile Gly Ile Ala Asn Thr Leu Asp Leu Thr Asp Arg Ile Leu Pro
        315                 320                 325 agg ctt caa gct aga gaa aaa tgt aag cca cag ctg ttg aac ttc cca     1242
Arg Leu Gln Ala Arg Glu Lys Cys Lys Pro Gln Leu Leu Asn Phe Pro
    330                 335                 340 cct tat acc aga aat cag ata gtc act att ttg caa gat cga ctt aat     1290
Pro Tyr Thr Arg Asn Gln Ile Val Thr Ile Leu Gln Asp Arg Leu Asn
345                 350                 355                 360 cag gta tct aga gat cag gtt ctg gac aat gct gca gtt caa ttc tgt     1338
Gln Val Ser Arg Asp Gln Val Leu Asp Asn Ala Ala Val Gln Phe Cys
                365                 370                 375 gcc cgc aaa gtc tct gct gtt tca gga gat gtt cgc aaa gca ctg gat     1386
Ala Arg Lys Val Ser Ala Val Ser Gly Asp Val Arg Lys Ala Leu Asp
            380                 385                 390 gtt tgc agg aga gct att gaa att gta gag tca gat gtc aaa agc cag     1434
Val Cys Arg Arg Ala Ile Glu Ile Val Glu Ser Asp Val Lys Ser Gln
        395                 400                 405 act att ctc aaa cca ctg tct gaa tgt aaa tca cct tct gag cct ctg     1482
Thr Ile Leu Lys Pro Leu Ser Glu Cys Lys Ser Pro Ser Glu Pro Leu
    410                 415                 420 att ccc aag agg gtt ggt ctt att cac ata tcc caa gtc atc tca gaa     1530
Ile Pro Lys Arg Val Gly Leu Ile His Ile Ser Gln Val Ile Ser Glu
425                 430                 435                 440 gtt gat ggt aac agg atg acc ttg agc caa gag gga gca caa gat tcc     1578
Val Asp Gly Asn Arg Met Thr Leu Ser Gln Glu Gly Ala Gln Asp Ser
                445                 450                 455 ttc cct ctt cag cag aag atc ttg gtt tgc tct ttg atg ctc ttg atc     1626
Phe Pro Leu Gln Gln Lys Ile Leu Val Cys Ser Leu Met Leu Leu Ile
            460                 465                 470 agg cag ttg aaa atc aaa gag gtc act ctg ggg aag tta tat gaa gcc     1674
Arg Gln Leu Lys Ile Lys Glu Val Thr Leu Gly Lys Leu Tyr Glu Ala
        475                 480                 485 tac agt aaa gtc tgt cgc aaa cag cag gtg gcg gct gtg gac cag tca     1722
Tyr Ser Lys Val Cys Arg Lys Gln Gln Val Ala Ala Val Asp Gln Ser
    490                 495                 500 gag tgt ttg tca ctt tca ggg ctc ttg gaa gcc agg ggc att tta gga     1770
Glu Cys Leu Ser Leu Ser Gly Leu Leu Glu Ala Arg Gly Ile Leu Gly
505                 510                 515                 520 tta aag aga aac aag gaa acc cgt ttg aca aag gtg ttt ttc aag att     1818
Leu Lys Arg Asn Lys Glu Thr Arg Leu Thr Lys Val Phe Phe Lys Ile
                525                 530                 535 gaa gag aaa gaa ata gaa cat gct ctg aaa gat aaa gct tta att gga     1866
Glu Glu Lys Glu Ile Glu His Ala Leu Lys Asp Lys Ala Leu Ile Gly
            540                 545                 550 aat atc tta gct act gga ttg cct taa attcttctct tacacccac            1913
Asn Ile Leu Ala Thr Gly Leu Pro
        555                 560 ccgaaagtat tcagctggca tttagagagc tacagtcttc attttagtgc tttacacatt   1973
cgggcctgaa acaaatatg accttttta cttgaagcca atgaatttta atctatagat    2033
tctttaatat tagcacagaa taatatcttt gggtcttact attttaccc ataaaagtga   2093 ccaggtagac cctttttaat tacattcact acttctacca cttgtgtatc tctagccaat  2153
gtgcttgcaa gtgtacagat ctgtgtagag gaatgtgtgt atatttacct cttcgtttgc  2213
tcaaacatga gtgggtattt ttttgtttgt ttttttttgtt gttgttgttt tgaggcgcg   2273 tctcaccctg ttgcccaggc tggagtgcaa tggcgcgttc tctgctcact acagcacccg  2333
cttcccaggt tgaagtgatt ctcttgcctc agcctcccga gtagctggga ttacaggtgc  2393
```

```
ccaccaccgc gcccagctaa ttttttaatt tttagtagag acagggtttt accatgttgg    2453
ccaggctggt cttgaactcc tgaccctcaa gtgatctgcc caccttggcc tccctaagtg    2513
ctgggattat aggcgtgagc caccatgctc agccattaag gtattttgtt aagaacttta    2573
agtttagggt aagaagaatg aaaatgatcc agaaaaatgc aagcaagtcc acatggagat    2633
ttggaggaca ctggttaaag                                                2653

<210> SEQ ID NO 2
<211> LENGTH: 560
<212> TYPE: PRT
<213> ORGANISM: H. sapiens

<400> SEQUENCE: 2

Met Pro Gln Thr Arg Ser Gln Ala Gln Ala Thr Ile Ser Phe Pro Lys
 1               5                  10                  15

Arg Lys Leu Ser Arg Ala Leu Asn Lys Ala Lys Asn Ser Ser Asp Ala
            20                  25                  30

Lys Leu Glu Pro Thr Asn Val Gln Thr Val Thr Cys Ser Pro Arg Val
        35                  40                  45

Lys Ala Leu Pro Leu Ser Pro Arg Lys Arg Leu Gly Asp Asp Asn Leu
    50                  55                  60

Cys Asn Thr Pro His Leu Pro Pro Cys Ser Pro Pro Lys Gln Gly Lys
65                  70                  75                  80

Lys Glu Asn Gly Pro Pro His Ser His Thr Leu Lys Gly Arg Arg Leu
                85                  90                  95

Val Phe Asp Asn Gln Leu Thr Ile Lys Ser Pro Ser Lys Arg Glu Leu
            100                 105                 110

Ala Lys Val His Gln Asn Lys Ile Leu Ser Ser Val Arg Lys Ser Gln
        115                 120                 125

Glu Ile Thr Thr Asn Ser Glu Gln Arg Cys Pro Leu Lys Lys Glu Ser
    130                 135                 140

Ala Cys Val Arg Leu Phe Lys Gln Glu Gly Thr Cys Tyr Gln Gln Ala
145                 150                 155                 160

Lys Leu Val Leu Asn Thr Ala Val Pro Asp Arg Leu Pro Ala Arg Glu
                165                 170                 175

Arg Glu Met Asp Val Ile Arg Asn Phe Leu Arg Glu His Ile Cys Gly
            180                 185                 190

Lys Lys Ala Gly Ser Leu Tyr Leu Ser Gly Ala Pro Gly Thr Gly Lys
        195                 200                 205

Thr Ala Cys Leu Ser Arg Ile Leu Gln Asp Leu Lys Lys Glu Leu Lys
    210                 215                 220

Gly Phe Lys Thr Ile Met Leu Asn Cys Met Ser Leu Arg Thr Ala Gln
225                 230                 235                 240

Ala Val Phe Pro Ala Ile Ala Gln Glu Ile Cys Gln Glu Glu Val Ser
                245                 250                 255

Arg Pro Ala Gly Lys Asp Met Met Arg Lys Leu Glu Lys His Met Thr
            260                 265                 270

Ala Glu Lys Gly Pro Met Ile Val Leu Val Leu Asp Glu Met Asp Gln
        275                 280                 285

Leu Asp Ser Lys Gly Gln Asp Val Leu Tyr Thr Leu Phe Glu Trp Pro
    290                 295                 300

Trp Leu Ser Asn Ser His Leu Val Leu Ile Gly Ile Ala Asn Thr Leu
305                 310                 315                 320

Asp Leu Thr Asp Arg Ile Leu Pro Arg Leu Gln Ala Arg Glu Lys Cys
```

```
                    325                 330                 335
Lys Pro Gln Leu Leu Asn Phe Pro Pro Tyr Thr Arg Asn Gln Ile Val
            340                 345                 350

Thr Ile Leu Gln Asp Arg Leu Asn Gln Val Ser Arg Asp Gln Val Leu
            355                 360                 365

Asp Asn Ala Ala Val Gln Phe Cys Ala Arg Lys Val Ser Ala Val Ser
370                 375                 380

Gly Asp Val Arg Lys Ala Leu Asp Val Cys Arg Arg Ala Ile Glu Ile
385                 390                 395                 400

Val Glu Ser Asp Val Lys Ser Gln Thr Ile Leu Lys Pro Leu Ser Glu
                405                 410                 415

Cys Lys Ser Pro Ser Glu Pro Leu Ile Pro Lys Arg Val Gly Leu Ile
                420                 425                 430

His Ile Ser Gln Val Ile Ser Glu Val Asp Gly Asn Arg Met Thr Leu
                435                 440                 445

Ser Gln Glu Gly Ala Gln Asp Ser Phe Pro Leu Gln Gln Lys Ile Leu
            450                 455                 460

Val Cys Ser Leu Met Leu Leu Ile Arg Gln Leu Lys Ile Lys Glu Val
465                 470                 475                 480

Thr Leu Gly Lys Leu Tyr Glu Ala Tyr Ser Lys Val Cys Arg Lys Gln
                485                 490                 495

Gln Val Ala Ala Val Asp Gln Ser Glu Cys Leu Ser Leu Ser Gly Leu
            500                 505                 510

Leu Glu Ala Arg Gly Ile Leu Gly Leu Lys Arg Asn Lys Glu Thr Arg
            515                 520                 525

Leu Thr Lys Val Phe Phe Lys Ile Glu Lys Glu Ile Glu His Ala
            530                 535                 540

Leu Lys Asp Lys Ala Leu Ile Gly Asn Ile Leu Ala Thr Gly Leu Pro
545                 550                 555                 560

<210> SEQ ID NO 3
<211> LENGTH: 1371
<212> TYPE: DNA
<213> ORGANISM: xenopus
<220> FEATURE:
<221> NAME/KEY: CDS
<222> LOCATION: (1)...(1371)

<400> SEQUENCE: 3 atg cca agc acc agg tct cgg tct caa agc tcc att cag ttt ccc aag    48
Met Pro Ser Thr Arg Ser Arg Ser Gln Ser Ser Ile Gln Phe Pro Lys
 1               5                  10                  15 aaa aag act tct cag acg ctc gcc aaa gag gtc tca cgt gca aag agc    96
Lys Lys Thr Ser Gln Thr Leu Ala Lys Glu Val Ser Arg Ala Lys Ser
            20                  25                  30 aag tct gag atc tgc tcc tct gtc tcc ctc ccg ctc tct cca ctt ccc   144
Lys Ser Glu Ile Cys Ser Ser Val Ser Leu Pro Leu Ser Pro Leu Pro
        35                  40                  45 aaa gag ctt ccc ctc agt cca cgc aaa cgg ctc ggt gat gac aat cgt   192
Lys Glu Leu Pro Leu Ser Pro Arg Lys Arg Leu Gly Asp Asp Asn Arg
 50                  55                  60 tgc aac att cct ccg aca tta agc tgc tcc cca ccc aag cag tct cgc   240
Cys Asn Ile Pro Pro Thr Leu Ser Cys Ser Pro Pro Lys Gln Ser Arg
 65                  70                  75                  80 aaa gag act ggc cag cca acc acc cct aag ggg cgc cgt tta ctt ttt   288
Lys Glu Thr Gly Gln Pro Thr Thr Pro Lys Gly Arg Arg Leu Leu Phe
                85                  90                  95
```

| | | |
|---|---|---|
| gat gag aac cag gct gca gca gcg aca cca cta tcc ccc ctc aag aag | 336 | |
| Asp Glu Asn Gln Ala Ala Ala Ala Thr Pro Leu Ser Pro Leu Lys Lys | | |
| 100 105 110 | | |
| cta cag gat cct tat ctg ctg tcc cct gtg aga aag ggg caa gag acc | 384 | |
| Leu Gln Asp Pro Tyr Leu Leu Ser Pro Val Arg Lys Gly Gln Glu Thr | | |
| 115 120 125 | | |
| cca ccc agc tct cgt aag caa agg aac agt gtg ggg gtc cag cta ttt | 432 | |
| Pro Pro Ser Ser Arg Lys Gln Arg Asn Ser Val Gly Val Gln Leu Phe | | |
| 130 135 140 | | |
| aaa cag gag ggc tcc tgc tat cag aag gct aag cac gct ttg aat acg | 480 | |
| Lys Gln Glu Gly Ser Cys Tyr Gln Lys Ala Lys His Ala Leu Asn Thr | | |
| 145 150 155 160 | | |
| gct ata cca gag cgc ctg ttg gct cgt gag agt gag act gca ttt atc | 528 | |
| Ala Ile Pro Glu Arg Leu Leu Ala Arg Glu Ser Glu Thr Ala Phe Ile | | |
| 165 170 175 | | |
| aag acc ttc ctg aca agt cat gtt tct gct ggg aaa gcc ggg agc ctt | 576 | |
| Lys Thr Phe Leu Thr Ser His Val Ser Ala Gly Lys Ala Gly Ser Leu | | |
| 180 185 190 | | |
| tac ata tct ggt gct cct gga act ggc aaa act gcg tgc ttg aat aag | 624 | |
| Tyr Ile Ser Gly Ala Pro Gly Thr Gly Lys Thr Ala Cys Leu Asn Lys | | |
| 195 200 205 | | |
| ctg ctg cag gag acc aag gat gat ctc aag cag tgc aag acc gtt tac | 672 | |
| Leu Leu Gln Glu Thr Lys Asp Asp Leu Lys Gln Cys Lys Thr Val Tyr | | |
| 210 215 220 | | |
| atc aac tgc atg tca ttg cgc agc tcc cag gca gtg ttt ccg gct ata | 720 | |
| Ile Asn Cys Met Ser Leu Arg Ser Ser Gln Ala Val Phe Pro Ala Ile | | |
| 225 230 235 240 | | |
| gct gaa gaa atc tct ggg ggc aaa tct tca ctg gcc gcc aaa gat att | 768 | |
| Ala Glu Glu Ile Ser Gly Gly Lys Ser Ser Leu Ala Ala Lys Asp Ile | | |
| 245 250 255 | | |
| gta agg agt ttg gag aag ctg gtg act tca aag ggt cca atc atc ttg | 816 | |
| Val Arg Ser Leu Glu Lys Leu Val Thr Ser Lys Gly Pro Ile Ile Leu | | |
| 260 265 270 | | |
| ctg gtg ttg gat gag atg gat cag ctg gac agc aga gga cag gat gtc | 864 | |
| Leu Val Leu Asp Glu Met Asp Gln Leu Asp Ser Arg Gly Gln Asp Val | | |
| 275 280 285 | | |
| ttg tac acc gtg ttt gag tgg cct tgg ctt aca aat tct agg atg gtt | 912 | |
| Leu Tyr Thr Val Phe Glu Trp Pro Trp Leu Thr Asn Ser Arg Met Val | | |
| 290 295 300 | | |
| tta atc ggc att gct aac gca ttg gat ttg aca gac cgt att ttg ccc | 960 | |
| Leu Ile Gly Ile Ala Asn Ala Leu Asp Leu Thr Asp Arg Ile Leu Pro | | |
| 305 310 315 320 | | |
| agg cta caa gct cga cgt ccg tgc aga cca cag ttg ctc aac ttt tct | 1008 | |
| Arg Leu Gln Ala Arg Arg Pro Cys Arg Pro Gln Leu Leu Asn Phe Ser | | |
| 325 330 335 | | |
| cca tat aca aag gat cag att gct acc att cta cag gac aga cta aat | 1056 | |
| Pro Tyr Thr Lys Asp Gln Ile Ala Thr Ile Leu Gln Asp Arg Leu Asn | | |
| 340 345 350 | | |
| acg gtt tca ggc gat caa gtt ctg gat aat gct gct att cag ttc tgt | 1104 | |
| Thr Val Ser Gly Asp Gln Val Leu Asp Asn Ala Ala Ile Gln Phe Cys | | |
| 355 360 365 | | |
| gca agg aaa atc tct gct gtc tct gga gat gct cga aag gcg cta gat | 1152 | |
| Ala Arg Lys Ile Ser Ala Val Ser Gly Asp Ala Arg Lys Ala Leu Asp | | |
| 370 375 380 | | |
| atc tgc agg aga gct gtt gaa att gtc gaa gcg gat gtc agg ggc cag | 1200 | |
| Ile Cys Arg Arg Ala Val Glu Ile Val Glu Ala Asp Val Arg Gly Gln | | |
| 385 390 395 400 | | |
| act gtc ctt aag cct cta act gaa tgt gcg tct cct tgt aaa gaa gtc | 1248 | |
| Thr Val Leu Lys Pro Leu Thr Glu Cys Ala Ser Pro Cys Lys Glu Val | | |
| 405 410 415 | | |

-continued

```
cca tta aac cct gtt cca aaa aag gtc agc ctt cca cac atc tct cgt    1296
Pro Leu Asn Pro Val Pro Lys Lys Val Ser Leu Pro His Ile Ser Arg
        420                 425                 430 gtc ctg tcg gat gtg tat ggg gac aag atg gca agc cgt gag ggt tca    1344
Val Leu Ser Asp Val Tyr Gly Asp Lys Met Ala Ser Arg Glu Gly Ser
            435                 440                 445 agc gag agt ttt ccc tta cag cag aaa                                1371
Ser Glu Ser Phe Pro Leu Gln Gln Lys
        450                 455
```

<210> SEQ ID NO 4
<211> LENGTH: 457
<212> TYPE: PRT
<213> ORGANISM: xenopus

<400> SEQUENCE: 4

```
Met Pro Ser Thr Arg Ser Arg Ser Gln Ser Ser Ile Gln Phe Pro Lys
 1               5                  10                  15

Lys Lys Thr Ser Gln Thr Leu Ala Lys Glu Val Ser Arg Ala Lys Ser
            20                  25                  30

Lys Ser Glu Ile Cys Ser Ser Val Ser Leu Pro Leu Ser Pro Leu Pro
        35                  40                  45

Lys Glu Leu Pro Leu Ser Pro Arg Lys Arg Leu Gly Asp Asp Asn Arg
    50                  55                  60

Cys Asn Ile Pro Pro Thr Leu Ser Cys Ser Pro Pro Lys Gln Ser Arg
65                  70                  75                  80

Lys Glu Thr Gly Gln Pro Thr Thr Pro Lys Gly Arg Arg Leu Leu Phe
                85                  90                  95

Asp Glu Asn Gln Ala Ala Ala Thr Pro Leu Ser Pro Leu Lys Lys
            100                 105                 110

Leu Gln Asp Pro Tyr Leu Leu Ser Pro Val Arg Lys Gly Gln Glu Thr
        115                 120                 125

Pro Pro Ser Ser Arg Lys Gln Arg Asn Ser Val Gly Val Gln Leu Phe
    130                 135                 140

Lys Gln Glu Gly Ser Cys Tyr Gln Lys Ala Lys His Ala Leu Asn Thr
145                 150                 155                 160

Ala Ile Pro Glu Arg Leu Leu Ala Arg Glu Ser Glu Thr Ala Phe Ile
                165                 170                 175

Lys Thr Phe Leu Thr Ser His Val Ser Ala Gly Lys Ala Gly Ser Leu
            180                 185                 190

Tyr Ile Ser Gly Ala Pro Gly Thr Gly Lys Thr Ala Cys Leu Asn Lys
        195                 200                 205

Leu Leu Gln Glu Thr Lys Asp Asp Leu Lys Gln Cys Lys Thr Val Tyr
    210                 215                 220

Ile Asn Cys Met Ser Leu Arg Ser Ser Gln Ala Val Phe Pro Ala Ile
225                 230                 235                 240

Ala Glu Glu Ile Ser Gly Gly Lys Ser Ser Leu Ala Ala Lys Asp Ile
                245                 250                 255

Val Arg Ser Leu Glu Lys Leu Val Thr Ser Lys Gly Pro Ile Ile Leu
            260                 265                 270

Leu Val Leu Asp Glu Met Asp Gln Leu Asp Ser Arg Gly Gln Asp Val
        275                 280                 285

Leu Tyr Thr Val Phe Glu Trp Pro Trp Leu Thr Asn Ser Arg Met Val
    290                 295                 300

Leu Ile Gly Ile Ala Asn Ala Leu Asp Leu Thr Asp Arg Ile Leu Pro
```

```
            305                 310                 315                 320
Arg Leu Gln Ala Arg Arg Pro Cys Arg Pro Gln Leu Leu Asn Phe Ser
                325                 330                 335
Pro Tyr Thr Lys Asp Gln Ile Ala Thr Ile Leu Gln Asp Arg Leu Asn
                340                 345                 350
Thr Val Ser Gly Asp Gln Val Leu Asp Asn Ala Ala Ile Gln Phe Cys
                355                 360                 365
Ala Arg Lys Ile Ser Ala Val Ser Gly Asp Ala Arg Lys Ala Leu Asp
        370                 375                 380
Ile Cys Arg Arg Ala Val Glu Ile Val Glu Ala Asp Val Arg Gly Gln
385                 390                 395                 400
Thr Val Leu Lys Pro Leu Thr Glu Cys Ala Ser Pro Cys Lys Glu Val
                405                 410                 415
Pro Leu Asn Pro Val Pro Lys Lys Val Ser Leu Pro His Ile Ser Arg
                420                 425                 430
Val Leu Ser Asp Val Tyr Gly Asp Lys Met Ala Ser Arg Glu Gly Ser
                435                 440                 445
Ser Glu Ser Phe Pro Leu Gln Gln Lys
        450                 455

<210> SEQ ID NO 5
<211> LENGTH: 956
<212> TYPE: DNA
<213> ORGANISM: H. sapiens

<400> SEQUENCE: 5
aagcttccat tgtgtggtaa ctttctccat tcatggcagc ccattctctt cacttttgta      60
gttttcagct gctaaaaagc cttcacgaaa tgtactccac catctcttcc tgtttagaac     120
ctgaatctgt ctaatcatcc ccctatgata agtggtcaa gaatttgatt ttctgtcaga     180
ttcagattca aattctagct cttccactta ctattgtgtg accttgggca attactcaac     240
tcccctctac tgtagttccc tcatttgtaa agtgaaataa caccaggttc atggggggtgc     300 ttgtgaaatt aataaggtga tgtatgtaaa atactgagca cagcccctgg catacactta     360
agcactcaat attggctctc ttcatgaact aggtaccaat tcactggatg atcgtaatat     420
tgttgcttcc ctctttctag gctttatggc tctattttgt ttgttactga ggggtaaaag     480
ataaatgttt accatcacct aaaattgggt tctggcccta aaggaacctg aggcttagat     540
gaattattgg ctttggaagc tggccttcaa attactgcgc taatttatat ttttcattaa     600
aactcagctt gcctcttcta tatagctgtc ttccctggcc ctgaaaccct agtgtttcgc     660
cataaaagat tttaaaatta aggggtcata attccctccc catgatgtgt ggattaatgg     720
taagaagatg ccagaacata atattcttag gttgaacgaa ataaagtaa agagttggct     780 ctgtttctca ccttttgaagc acaaatcaag agatactatg atgaagcata gtttttcttt     840
atataggtgt gtagaacttt accataaaaa tcactagttc agccatcagg agatctggat     900
cctaggctct tcactgtcac caagatgctg tgacctctaa ccttgtatag aagttt          956

<210> SEQ ID NO 6
<211> LENGTH: 963
<212> TYPE: DNA
<213> ORGANISM: H. sapiens

<400> SEQUENCE: 6
tgggttctgg ccctaaagga acctgaggct tagatgaatt attggctttg gaagctggcc      60
```

-continued

| | |
|---|---|
| ttcaaattac tgcgctaatt tatattttc attaaaactc agcttgcctc ttctatatag | 120 |
| ctgtcttccc tggccctgaa acctagtgt ttcgccataa agattttaa aattaagggg | 180 |
| tcataattcc ctccccatga tgtgtggatt aatggtaaga agatgccaga acataatatt | 240 |
| cttaggttga acgaaataaa agtaaagagt tggctctgtt tctcaccttt gaagcacaaa | 300 |
| tcaagagata ctatgatgaa gcatagtttt tctttatata ggtgtgtaga actttaccat | 360 |
| aaaaatcact agttcagcca tcaggagatc tggatcctag gctcttcact gtcaccaaga | 420 |
| tgctgtgacc tctaaccttg tatagaagtt tgctttgtac tttgcgaggt tgagcattag | 480 |
| agaggtaagg aaagtgccta gcatcatacc tggcgcacag aacccaaaac ggtaggtatc | 540 |
| atgtagcagt tctgaaaatc tagcccatca ggatgatgca aatgggtact ttaggcagtg | 600 |
| agaaggggaa ccacatcttg acacttccag tcgaaggaag agtgcgactg cgcggcagca | 660 |
| aagactacgc ctcccagcgt gctttgcggc gggccggccc gctttaccca gagtcgccct | 720 |
| gccgcaatcg cgggttttt ccaccgaggc cccggatgta gattcccttc ccccgttcag | 780 |
| tggtggtggc ctcacagcga ctctaagact tggggctctc tcattggctg taactcttcc | 840 |
| actggattgg tagcaaaaaa agaggcggtg cccaaggcga aaggctctgt gactacagcc | 900 |
| aatcagaatc gaggccgggc tttggcggga ggtgggaacg ctgtggccat tcggatttgg | 960 |
| cgc | 963 |

<210> SEQ ID NO 7
<211> LENGTH: 196
<212> TYPE: DNA
<213> ORGANISM: H. sapiens

<400> SEQUENCE: 7

| | |
|---|---|
| gagcgcggct ggagtttgct gctgccgctg tgcagtttgt tcagggcttt gtggcggtga | 60 |
| gtccgagagg ctgcgtgtga gagacgtgag aaggatcctg cactgaggag gtggaaagaa | 120 |
| gaggattgct cgaggaggcc tggggtctgt gagacagcgg agctgggtga aggctgcggg | 180 |
| ttccggcgag gcctga | 196 |

<210> SEQ ID NO 8
<211> LENGTH: 335
<212> TYPE: DNA
<213> ORGANISM: H. sapiens

<400> SEQUENCE: 8

| | |
|---|---|
| agggaaaaga gctgagctcg ctggaggtct gaggtcggga tcagggaaag ggcaggtgcc | 60 |
| ctcgggtag ttctagcagt tatgcgtggt gtgaaggagg tgaaagttgt aggaaggaaa | 120 |
| tattctgggg tgcgttgaga gctgcctaga aggaggactg agtgcagggg cggaaagaac | 180 |
| tgagggaaga ctgagctgca gtgtgagggc ttgggataga agagactaaa tgtgcgggt | 240 |
| gctgggctga actggtgata aagacacccc gcgtgcctgg agggaggaaa ctagaagttc | 300 |
| tatataaatc aattcatgta acttttttt ttttt | 335 |

<210> SEQ ID NO 9
<211> LENGTH: 193
<212> TYPE: DNA
<213> ORGANISM: H. sapiens

<400> SEQUENCE: 9

| | |
|---|---|
| gctgtgctgt cgtcatgcct caaacccgat cccaggcaca ggctacaatc agttttccaa | 60 |
| aaaggaagct gtctcgggca ttgaacaaag ctaaaaactc cagtgatgcc aaactagaac | 120 |

```
caacaaatgt ccaaaccgta acctgttctc ctcgtgtaaa agccctgcct ctcagcccca      180
ggaaacgtct ggg                                                         193

<210> SEQ ID NO 10
<211> LENGTH: 128
<212> TYPE: DNA
<213> ORGANISM: H. sapiens

<400> SEQUENCE: 10
taaaccatcc attatatcac tttttcacta gcagctcgtg acctttcttt tcttggtaag       60
atgtgtgtcc tttgaaggag ctttctaagt tcagttaaga cttcttttttt ttttttttttt   120 tttttttgg                                                              128

<210> SEQ ID NO 11
<211> LENGTH: 111
<212> TYPE: DNA
<213> ORGANISM: H. sapiens

<400> SEQUENCE: 11
cgatgacaac ctatgcaaca ctccccattt acctccttgt tctccaccaa agcaaggcaa       60
gaaagagaat ggtcccccctc actcacatac acttaaggga cgaagattgg t              111

<210> SEQ ID NO 12
<211> LENGTH: 1210
<212> TYPE: DNA
<213> ORGANISM: H. sapiens

<400> SEQUENCE: 12 ggggccccccc cccaaacctg ggtaaatttt tttttttttt tttttggatt tttagttgag      60
acagggtttt gccatattgg ccaatctggt tctgaactc ctgacctcag gtgatccaac       120
tgcctcggcc tcccaaagtg ctgggattat aggcatgagc taccgctcct ggcctaagac      180
tactcttcat tttagttatt ttcagaatgg ttgctaagtg cttaccgaac tccagagtta      240
gacacttact gaggtcactc tgaactactt aataagtctg atcttcaatt ccttaatact      300
gaacttagtt ctgtcaatgt tttaagttac cttgtagtta catggtatta tgaaacttac      360 ctcaatatt gtgaaattaa agaaacaaa acgtgacat gatgaatatt ttccatcctt         420
taggacagtg attggtaatt ctttcgatgg ttttggaacat ttattttttaa atgggggta    480 atttggttgt ttctggagac attttttggtt gttacagctg ggggttgcta ctggcatagt    540
gggtagaggc cagggatgct gctagacatt acaatgcaca ggacagctcc tttgacaatg    600
aagaattatt tggtccaaga tgtcagtggt gccaaggttg agaaaccctg tttcaaaata    660
gccttacaat ttcatcctac taaaacccat ttggtttcta ctaaatgcag tagtccccac     720
ttatccatgg gggatacatt ccaagacccc cagtggacgc ctgcaatcga ggacagtacc    780 aaacccctaca tatactgtgt ttttgatttg ataaccaagt cagctactaa gtgactagtg   840
ggtggatagc atatacagtg tggatatgct ggctgaaggg atgattcatg tcttgggtag    900
gatggtgcgg gatttcatca tggcactcca cagcatgcaa tttaaaactt gtcaattgtt    960
tatttctgga atttttccatt tagtattttc agactgaggg taactagaac ggtggatgaa  1020
gggactactg tagtaagatc agtggtgcca tctggtgacc aatatttgct gctaagtgag  1080
aaggcatttt attttggtgg ttctgactaa ggtagaaatt caccctctttc tggaagaggc  1140 agaggtcttg cacatccttt tactatccaa tgctatgagt gactacattt ttattttatt   1200
```

-continued

```
gtgtttcagg                                                                 1210

<210> SEQ ID NO 13
<211> LENGTH: 168
<212> TYPE: DNA
<213> ORGANISM: H. sapiens

<400> SEQUENCE: 13
atttgacaat cagctgacaa ttaagtctcc tagcaaaaga gaactagcca aagttcacca     60
aaacaaaata ctttcttcag ttagaaaaag tcaagagatc acaacaaatt ctgagcagag    120
atgtccactg aagaaagaat ctgcatgtgt gagactattc aagcaaga                 168

<210> SEQ ID NO 14
<211> LENGTH: 129
<212> TYPE: DNA
<213> ORGANISM: H. sapiens

<400> SEQUENCE: 14
aggtttgttc ttacatggca actgttagtg cagccattgt aaccaaggct gatgactcca     60
aatgaaacca cccactgggt cttctcattc accttctgtt gtgtctaatt gaccttttat    120
gtctggcac                                                            129

<210> SEQ ID NO 15
<211> LENGTH: 202
<212> TYPE: DNA
<213> ORGANISM: H. sapiens

<400> SEQUENCE: 15
aggcacttgc taccagcaag caaagctggt cctgaacaca gctgtcccag atcggctgcc     60
tgccagggaa agggagatgg atgtcatcag gaatttcttg agggaacaca tctgtgggaa    120
aaaagctgga agcctttacc tttctggtgc tcctggaact ggaaaaactg cctgcttaag    180
ccggattctg caagacctca ag                                             202

<210> SEQ ID NO 16
<211> LENGTH: 685
<212> TYPE: DNA
<213> ORGANISM: H. sapiens

<400> SEQUENCE: 16
gtacattgag agtctgaatt atgatactct tggtaaaatg atacttgggt gttttttgttt    60 gtttgtttgt tttgttttgt tttgttttgt tttttgagac ggagtctcgc tctgtcgcct    120
aggctgtagt gcagtggcga cagagcaaga ctcccgtctc aaaaaaaaaa agagttaaga    180
aagagtaggc ctggtgcggt ggctcacacc tgtaattcca cactttggg aggctgaggc     240 aggtggatca cctgaggtca ggagttcaag accagcctgg ccaatgtggc gaaaccccat    300
ctctactaaa aatataaaaa ttagctgggt gtggtggtgc atccttgtaa tcccagctac    360
ttgggaggct gaggcaggag aatcacttca acccggagg cagaggttgc aatgagttga     420
gattgtggca ttgcatttca gcctgggcaa cagagtgaga ctccgtctca agaaaaaaa     480 aagaaagaaa gaaagaaag agtagaagtt tagaagattg agggtttctt caaaataaaa    540
catttgtaat ttcattgttt aaatctttcc aaatgaaagt agagcttcct tacgtgctgt    600
tagctcttca aagacatttt aggctctatc agatctttat tttctgaggc caaaataact    660
cccatatttg cattttttt tccag                                           685
```

<210> SEQ ID NO 17
<211> LENGTH: 176
<212> TYPE: DNA
<213> ORGANISM: H. sapiens

<400> SEQUENCE: 17

```
aaggaactga aaggctttaa aactatcatg ctgaattgca tgtccttgag gactgcccag    60
gctgtattcc cagctattgc tcaggagatt tgtcaggaag aggtatccag gccagctggg   120
aaggacatga tgaggaaatt ggaaaaacat atgactgcag agaagggccc catgat       176
```

<210> SEQ ID NO 18
<211> LENGTH: 320
<212> TYPE: DNA
<213> ORGANISM: H. sapiens

<400> SEQUENCE: 18

```
gtaagtattg ttctggcttc catgttgctc tgtgaaaatc tgcaaggtct gttgcccata    60
aaaagtacat tttgtatatt ttctctctga aggatagtta cataaactta agggaaaga   120
agagaaggaa gatacaccta attttaaatt ggattactta tagatgatgt ggggtatcct   180
tgtagcagta actagagata ggttagatta tgatctttaa actggtctca gctttaggaa   240
agtgacctga agtcagccta tatcaaacat tagagggtta agaaggtgaa tatggatact   300
aactgtttct ctttttatag                                              320
```

<210> SEQ ID NO 19
<211> LENGTH: 109
<212> TYPE: DNA
<213> ORGANISM: H. sapiens

<400> SEQUENCE: 19

```
tgtgttggta ttggacgaga tggatcaact ggacagcaaa ggccaggatg tattgtacac    60
gctatttgaa tggccatggc taagcaattc tcacttggtg ctgattggt               109
```

<210> SEQ ID NO 20
<211> LENGTH: 307
<212> TYPE: DNA
<213> ORGANISM: H. sapiens

<400> SEQUENCE: 20

```
tagtgctcaa ttgttaatgt tacatggtgg ttctaaagta ttttttaaga atatatattc    60
agcttattta tcagctattt tatcttaaac cagctttctg ccgtgtcaaa ataagaaagt   120
taaatgacta tgtacatctt acctaataga tacatcttat ctattgggat ggggtaggag   180
acaagtggca agcaacaatt agaatgctag attctataac tggagattta tttagctttc   240
agaagattta gttttccctt taggataatt tgaccaatga tcaatgttgt tgatctcctc   300
cttaggt                                                            307
```

<210> SEQ ID NO 21
<211> LENGTH: 507
<212> TYPE: DNA
<213> ORGANISM: H. sapiens

<400> SEQUENCE: 21

```
attgctaata ccctggatct cacagataga attctaccta ggcttcaagc tagagaaaaa    60
tgtaagccac agctgttgaa cttcccacct tataccagaa atcagatagt cactattttg   120
caagatcgac ttaatcaggt atctagagat caggttctgg acaatgctgc agttcaattc   180
```

-continued

```
tgtgcccgca aagtctctgc tgtttcagga gatgttcgca aagcactgga tgtttgcagg      240
agagctattg aaattgtaga gtcagatgtc aaaagccaga ctattctcaa accactgtct      300
gaatgtaaat caccttctga gcctctgatt cccaagaggg ttggtcttat tcacatatcc      360
caagtcatct cagaagttga tggtaacagg atgaccttga gccaagaggg agcacaagat      420
tccttccctc ttcagcagaa gatcttggtt tgctctttga tgctcttgat caggcagttg      480
aaaatcaaag aggtcactct ggggaag                                          507

<210> SEQ ID NO 22
<211> LENGTH: 437
<212> TYPE: DNA
<213> ORGANISM: H. sapiens

<400> SEQUENCE: 22
gtaagttggg atggagcaga tggaacggag gtagagatca gaatctgctt tgcagagcag       60 gtatttttcca aaaggcctat gatacttcag ctgataataa atttaaaatg gattttaaca     120
gtaagaatta atactggtac tatataaaag gcacctattt cccttggatt gtggttgaga     180
gtttatcatt aatcctttcc ctatcctccc cttcatttct gcatctctct aggaaatata     240
taaagcccct ttcctacatt actgtatagg ttttcgggaa tatctacaga agcctgttca     300
aagattttat tgaaagagg aagaaatagg gtattcagat aagttttttgc aaacccagac     360 tcaggttttct taaatgatta aaggctataa gcaatgtgac ttttaagcag cgtttgttct     420
cccttgtttc ctaccag                                                    437

<210> SEQ ID NO 23
<211> LENGTH: 143
<212> TYPE: DNA
<213> ORGANISM: H. sapiens

<400> SEQUENCE: 23
ttatatgaag cctacagtaa agtctgtcgc aaacagcagg tggcggctgt ggaccagtca       60
gagtgtttgt cactttcagg gctcttggaa gccaggggca ttttaggatt aaagagaaac     120
aaggaaaccc gtttgacaaa ggt                                             143

<210> SEQ ID NO 24
<211> LENGTH: 299
<212> TYPE: DNA
<213> ORGANISM: H. sapiens

<400> SEQUENCE: 24
acaactgctt ttttgtgaca gtgtttttaa ttgtcctatt ttgtagagtg atgctaaagt       60
aaaggtttat tgttaaacaa gatgaccaca gttagttaaa caagtcgttt tttgttaggt     120
aaggtttaag gtgtgtaaag atgggagtgt gatatgaata ttttttcaag ccattggaaa     180
aaaaagtgtt taacttgctt gccttttgtg agaaaagtt taatatggta gaagtttgta     240
tactgacaac tttgcttttg tgagttcccc agtgtgaaaa atccttttct cttctttcc     299

<210> SEQ ID NO 25
<211> LENGTH: 853
<212> TYPE: DNA
<213> ORGANISM: H. sapiens

<400> SEQUENCE: 25 gttttttcaag attgaagaga aagaaataga acatgctctg aaagataaag ctttaattgg       60
aaatatctta gctactggat tgccttaaat tcttctctta caccccaccc gaaagtattc     120
```

-continued

```
agctggcatt tagagagcta cagtcttcat tttagtgctt tacacattcg ggcctgaaaa     180
caaatatgac cttttttact tgaagccaat gaatttttaat ctatagattc tttaatatta    240
gcacagaata atatctttgg gtcttactat ttttacccat aaaagtgacc aggtagaccc     300 ttttttaatta cattcactac ttctaccact tgtgtatctc tagccaatgt gcttgcaagt    360
gtacagatct gtgtagagga atgtgtgtat atttacctct tcgtttgctc aaacatgagt    420 gggtatttt ttgtatgttt ttttgttgt tgttgttttt gaggcgcgtc tcaccctgtt       480
gcccaggctg gagtgcaatg gcgcgttctc tgctcactac agcacccgct tcccaggttg     540
aagtgattct cttgcctcag cctcccgagt agctgggatt acaggtgccc accaccgcgc     600
ccagctaatt ttttaatttt tagtagagac agggttttac catgttggcc aggctggtct    660
tgaactcctg accctcaagt gatctgccca ccttggcctc cctaagtgct gggattatag    720
gcgtgagcca ccatgctcag ccattaaggt attttgttaa gaactttaag tttagggtaa    780
gaagaatgaa aatgatccag aaaaatgcaa gcaagtccac atggagattt ggaggacact    840
ggttaaagaa ttc                                                       853

<210> SEQ ID NO 26
<211> LENGTH: 453
<212> TYPE: DNA
<213> ORGANISM: H. sapiens

<400> SEQUENCE: 26
cagaaaaatg caagcaagtc cacatggaga tttggaggac actggttaaa gaattctatt     60
tctttgtata cgtatactat gttcatggtg cagatactac aacattgtgg cattttagac    120
tcgttgagtt tcttgggcac tcccaagggc gttggggtca taggagact ataactctac     180 agattgtgaa tatatttatt ttcaagttgc attctttgtc ttttttaagca atcagatttc    240 aagagagctc aagctttcag aagtcaatgt gaaaattcct tcctaggctg tcccacagtc    300
tttgctgccc ttagatgaag ccacttgttt caagatgact actttggggt tgggttttca    360
tctaaacaca ttttttccagt cttattagat aaattagtcc atatggttgg ttaatcaaga    420
gccttctggg tttggtttgg tggcattaaa tgg                                 453

<210> SEQ ID NO 27
<211> LENGTH: 20
<212> TYPE: DNA
<213> ORGANISM: Artificial Sequence
<220> FEATURE:
<223> OTHER INFORMATION: primer

<400> SEQUENCE: 27
cctctcagcc ccaggaaacg                                                 20

<210> SEQ ID NO 28
<211> LENGTH: 8
<212> TYPE: PRT
<213> ORGANISM: K. lactis

<400> SEQUENCE: 28

Gly Thr Pro Thr Val Gly Lys Thr
 1               5

<210> SEQ ID NO 29
<211> LENGTH: 8
<212> TYPE: PRT
<213> ORGANISM: S. cerevisiae
```

<400> SEQUENCE: 29

Gly Thr Pro Gly Val Gly Lys Thr
1               5

<210> SEQ ID NO 30
<211> LENGTH: 8
<212> TYPE: PRT
<213> ORGANISM: H. sapiens

<400> SEQUENCE: 30

Gly Val Pro Gly Thr Gly Lys Thr
1               5

<210> SEQ ID NO 31
<211> LENGTH: 8
<212> TYPE: PRT
<213> ORGANISM: S. pombe

<400> SEQUENCE: 31

Gly Thr Pro Gly Thr Gly Lys Thr
1               5

<210> SEQ ID NO 32
<211> LENGTH: 8
<212> TYPE: PRT
<213> ORGANISM: S. cerevisiae

<400> SEQUENCE: 32

Gly Pro Pro Gly Thr Gly Lys Thr
1               5

<210> SEQ ID NO 33
<211> LENGTH: 8
<212> TYPE: PRT
<213> ORGANISM: S. pombe

<400> SEQUENCE: 33

Gly Ala Pro Gly Thr Gly Lys Thr
1               5

<210> SEQ ID NO 34
<211> LENGTH: 24
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (3)...(3)
<223> OTHER INFORMATION: n = Inosine
<220> FEATURE:
<221> NAME/KEY: modified_base
<222> LOCATION: (4)...(4)
<223> OTHER INFORMATION: s = c or g
<220> FEATURE:
<221> NAME/KEY: modified_base
<222> LOCATION: (6)...(6)
<223> OTHER INFORMATION: h = a or c or t/u; not G
<220> FEATURE:
<221> NAME/KEY: modified_base
<222> LOCATION: (9)...(9)
<223> OTHER INFORMATION: h = a or c or t/u; not G
<220> FEATURE:
<221> NAME/KEY: misc_feature
<222> LOCATION: (12)...(12)
<223> OTHER INFORMATION: n = inosine
<220> FEATURE:
<221> NAME/KEY: modified_base

```
<222> LOCATION: (15)...(15)
<223> OTHER INFORMATION: h = a or c or t/u; not G
<223> OTHER INFORMATION: n = inosine
<220> FEATURE:
<221> NAME/KEY: modified_base
<222> LOCATION: (21)...(21)
<223> OTHER INFORMATION: r = a or g
<220> FEATURE:
<221> NAME/KEY: modified_base
<222> LOCATION: (24)...(24)
<223> OTHER INFORMATION: h = a or c or t/u; not G

<400> SEQUENCE: 34
ggnschcchg gnachggnaa rach                                          24

<210> SEQ ID NO 35
<211> LENGTH: 8
<212> TYPE: PRT
<213> ORGANISM: K. lactis

<400> SEQUENCE: 35

Val Val Leu Leu Asp Glu Leu Asp
 1               5

<210> SEQ ID NO 36
<211> LENGTH: 8
<212> TYPE: PRT
<213> ORGANISM: S. cerevisiae

<400> SEQUENCE: 36

Val Val Leu Leu Asp Glu Leu Asp
 1               5

<210> SEQ ID NO 37
<211> LENGTH: 8
<212> TYPE: PRT
<213> ORGANISM: H. sapiens

<400> SEQUENCE: 37

Val Leu Leu Val Asp Glu Leu Asp
 1               5

<210> SEQ ID NO 38
<211> LENGTH: 8
<212> TYPE: PRT
<213> ORGANISM: S. pombe

<400> SEQUENCE: 38

Val Val Leu Met Asp Glu Leu Asp
 1               5

<210> SEQ ID NO 39
<211> LENGTH: 8
<212> TYPE: PRT
<213> ORGANISM: S. cerevisiae

<400> SEQUENCE: 39

Val Val Val Leu Asp Glu Met Asp
 1               5

<210> SEQ ID NO 40
<211> LENGTH: 8
<212> TYPE: PRT
<213> ORGANISM: S. pombe

<400> SEQUENCE: 40
```

```
Ile Ile Val Leu Asp Glu Met Asp
1               5

<210> SEQ ID NO 41
<211> LENGTH: 19
<212> TYPE: DNA
<213> ORGANISM: Artificial Sequence
<220> FEATURE:
<223> OTHER INFORMATION: primer
<220> FEATURE:
<221> NAME/KEY: modified_base
<222> LOCATION: (1)...(1)
<223> OTHER INFORMATION: r = a or g
<220> FEATURE:
<221> NAME/KEY: modified_base
<222> LOCATION: (3)...(3)
<223> OTHER INFORMATION: y = c or t/u
<220> FEATURE:
<221> NAME/KEY: modified_base
<222> LOCATION: (6)...(6)
<223> OTHER INFORMATION: b = c or g or t/u
<220> FEATURE:
<221> NAME/KEY: modified_base
<222> LOCATION: (9)...(9)
<223> OTHER INFORMATION: s = c or g
<220> FEATURE:
<221> NAME/KEY: modified_base
<222> LOCATION: (12)...(12)
<223> OTHER INFORMATION: y = c or t/u
<220> FEATURE:
<221> NAME/KEY: modified_base
<222> LOCATION: (15)...(15)
<223> OTHER INFORMATION: r = a or g

<400> SEQUENCE: 41
rtygtbctsg aygaratgg                                            19

<210> SEQ ID NO 42
<211> LENGTH: 8
<212> TYPE: PRT
<213> ORGANISM: K. lactis

<400> SEQUENCE: 42

Leu Asp Leu Pro Glu Arg His Leu
1               5

<210> SEQ ID NO 43
<211> LENGTH: 8
<212> TYPE: PRT
<213> ORGANISM: S. cerevisiae

<400> SEQUENCE: 43

Met Asp Leu Pro Glu Arg His Leu
1               5

<210> SEQ ID NO 44
<211> LENGTH: 8
<212> TYPE: PRT
<213> ORGANISM: H. sapiens

<400> SEQUENCE: 44

Met Asp Leu Pro Glu Arg Ile Met
1               5

<210> SEQ ID NO 45
<211> LENGTH: 8
<212> TYPE: PRT
<213> ORGANISM: S. pombe

<400> SEQUENCE: 45
```

Met Asp Leu Pro Glu Arg Ile Leu
1               5

<210> SEQ ID NO 46
<211> LENGTH: 8
<212> TYPE: PRT
<213> ORGANISM: S. cerevisiae

<400> SEQUENCE: 46

Leu Asp Met Lys Asp Arg Phe Leu
1               5

<210> SEQ ID NO 47
<211> LENGTH: 8
<212> TYPE: PRT
<213> ORGANISM: S. pombe

<400> SEQUENCE: 47

Leu Asp Met Thr Asp Arg Phe Leu
1               5

<210> SEQ ID NO 48
<211> LENGTH: 20
<212> TYPE: DNA
<213> ORGANISM: Artificial Sequence
<220> FEATURE:
<223> OTHER INFORMATION: primer
<220> FEATURE:
<221> NAME/KEY: modified_base
<222> LOCATION: (3)...(3)
<223> OTHER INFORMATION: r = a or g
<220> FEATURE:
<221> NAME/KEY: modified_base
<222> LOCATION: (8)...(8)
<223> OTHER INFORMATION: k = g or t/u
<220> FEATURE:
<221> NAME/KEY: modified_base
<222> LOCATION: (9)...(9)
<223> OTHER INFORMATION: r = a or g
<220> FEATURE:
<221> NAME/KEY: modified_base
<222> LOCATION: (13)...(13)
<223> OTHER INFORMATION: k = g or t/u
<220> FEATURE:
<221> NAME/KEY: modified_base
<222> LOCATION: (18)...(18)
<223> OTHER INFORMATION: r = a or g
<220> FEATURE:
<221> NAME/KEY: modified_base
<222> LOCATION: (6)...(6)
<223> OTHER INFORMATION: n=Inosine
<220> FEATURE:
<221> NAME/KEY: modified_base
<222> LOCATION: (12)...(12)
<223> OTHER INFORMATION: n=Inosine

<400> SEQUENCE: 48
agraanckrt cnktcatrtc                                          20

<210> SEQ ID NO 49
<211> LENGTH: 577
<212> TYPE: PRT
<213> ORGANISM: S. cerevisiae

<400> SEQUENCE: 49

Met Cys Glu Thr Pro Ile Gly Cys His Thr Pro Arg Arg Cys Asn Arg
1               5                   10                  15

Phe Ile Asp Ser Ala Ala Leu Ile Asp Cys Thr Asn Lys Thr Asn Gln
                20                  25                  30

```
Arg Glu His Ser Pro Ser Phe Ser Ile Glu Ile Pro Thr Pro Ser
         35                  40                  45

Arg Lys Arg Thr Leu Ala Ser Ser His Phe Gln Thr Pro Thr Lys Arg
 50                  55                  60

Ile Lys Tyr Glu Leu Gly Glu Leu Gln Glu Glu Lys Thr Asp Leu Tyr
 65                  70                  75                  80

Pro Asn Phe Pro Ala Gln Leu Lys Glu Asn Lys Lys Pro Lys Leu Pro
                 85                  90                  95

Thr Thr Pro Gln Thr Pro Lys Thr Pro Lys Arg Thr Ile Gln Ile Val
             100                 105                 110

Thr Pro Lys Ser Leu Asn Arg Thr Cys Asn Pro Val Pro Phe Ala Thr
             115                 120                 125

Arg Leu Leu Gln Ser Thr Pro His Arg Gln Leu Phe Pro Pro Thr Pro
         130                 135                 140

Ser Thr Pro Ser Thr Pro Ser Tyr Asn Ser Thr Ala Lys Leu Ser Leu
145                 150                 155                 160

Arg Lys Ser Tyr Arg Ser Ala Gly Val Val Gly Arg Glu Asn Glu Lys
                 165                 170                 175

Ser Ile Val Glu Ser Phe Phe Arg Gln His Leu Asp Ala Asn Ala Gly
             180                 185                 190

Gly Ala Leu Tyr Val Ser Gly Ala Pro Gly Thr Gly Lys Thr Val Leu
         195                 200                 205

Leu His Asn Val Leu Asp His Val Val Ser Asp Tyr Pro Lys Val Asn
         210                 215                 220

Val Cys Tyr Ile Asn Cys Met Thr Ile Asn Glu Pro Lys Ala Ile Phe
225                 230                 235                 240

Glu Lys Ile His Ser Lys Ile Val Lys Glu Glu Ile Leu Glu Asn Glu
                 245                 250                 255

Asp His His Ile Asn Phe Gln Cys Glu Leu Glu Ser His Phe Thr Gln
             260                 265                 270

Ser Ala Asn Glu Leu Tyr Asn Pro Val Ile Ile Val Leu Asp Glu Met
         275                 280                 285

Asp His Leu Ile Ala Arg Glu Gln Gln Val Leu Tyr Thr Leu Phe Glu
         290                 295                 300

Trp Pro Ser Arg Pro Thr Ser Arg Leu Ile Leu Val Gly Ile Ala Asn
305                 310                 315                 320

Ala Leu Asp Met Thr Asp Arg Phe Leu Pro Arg Leu Arg Thr Lys His
                 325                 330                 335

Ile Thr Pro Lys Leu Leu Ser Phe Thr Pro Tyr Thr Ala Gln Glu Ile
             340                 345                 350

Ser Thr Ile Ile Lys Ala Arg Leu Lys Thr Ala Thr Thr Ser Glu
         355                 360                 365

Lys Asn Asn Pro Phe Thr Pro Ile Lys Ser Ile Ser Glu Val Ser Asp
         370                 375                 380

Asp Ser Ile Asn Val Val Ser Gln His Ala Asp Glu Thr Pro Phe Ile
385                 390                 395                 400

His Pro Ala Ala Ile Glu Leu Cys Ala Arg Lys Val Ala Ala Ser Ser
                 405                 410                 415

Gly Asp Leu Arg Lys Ala Leu Asp Ile Cys Arg His Ala Ile Glu Leu
             420                 425                 430

Ala Glu Arg Glu Trp Lys Ala Gln His Asp Asn Thr Leu Ser Ser Val
         435                 440                 445
```

```
Asp Ile Pro Arg Ala Ser Ile Ala His Val Val Arg Ala Thr Ser Ala
            450                 455                 460

Met Ser Gln Ser Ala Ser Ala Arg Leu Lys Asn Leu Gly Leu Gln Gln
465                 470                 475                 480

Lys Ala Ile Leu Cys Thr Leu Val Val Cys Glu Lys Thr Ser Leu Ser
                    485                 490                 495

Val Ala Asp Val Phe Glu Lys Tyr Ser Ser Leu Cys Leu Arg Asp Arg
                500                 505                 510

Leu Ile Tyr Pro Leu Thr Ser Ser Glu Phe Cys Asp Val Ala Asn Ser
            515                 520                 525

Leu Glu Thr Leu Ala Ile Ile Arg Leu Arg Thr Lys Gln Arg Asn Gly
        530                 535                 540

Lys Pro Gln Asp Arg Ile Ile Ser Leu Leu Val Pro Glu Met Asp Val
545                 550                 555                 560

Ile Thr Ala Val Gly Asp Ile Gly Ile Leu Lys Arg Phe Phe Asp Arg
                565                 570                 575

Arg
```

<210> SEQ ID NO 50
<211> LENGTH: 513
<212> TYPE: PRT
<213> ORGANISM: S. pombe

<400> SEQUENCE: 50

```
Met Ser Ala Ile Pro Ile Thr Pro Thr Lys Arg Ile Arg Arg Asn Leu
1               5                   10                  15

Pro Asp Asp Ala Pro Ala Thr Pro Pro Arg Pro Leu Lys Arg Lys Lys
            20                  25                  30

Leu Gln Phe Thr Asp Val Thr Pro Glu Ser Ser Pro Glu Lys Leu Gln
        35                  40                  45

Phe Gly Ser Gln Ser Ile Phe Leu Arg Thr Lys Ala Leu Leu Gln Lys
    50                  55                  60

Ser Ser Glu Leu Val Asn Leu Asn Ser Ser Asp Gly Ala Leu Pro Ala
65                  70                  75                  80

Arg Thr Ala Glu Tyr Glu Gln Val Met Asn Phe Leu Ala Lys Ala Ile
                85                  90                  95

Ser Glu His Arg Ser Asp Ser Leu Tyr Ile Thr Cys Pro Pro Gly Thr
            100                 105                 110

Gly Lys Thr Ala Gln Leu Asp Met Ile Ile Arg Gln Lys Phe Gln Ser
        115                 120                 125

Leu Pro Leu Ser Leu Ser Thr Pro Arg Ser Lys Asp Val Leu Arg His
    130                 135                 140

Thr Asn Pro Asn Leu Gln Asn Leu Ser Trp Phe Glu Leu Pro Asp Gly
145                 150                 155                 160

Arg Leu Glu Ser Val Ala Val Thr Ser Ile Asn Cys Ile Ser Leu Gly
                165                 170                 175

Glu Pro Ser Ser Ile Phe Gln Lys Ile Phe Asp Ser Phe Gln Asp Leu
            180                 185                 190

Asn Gly Pro Thr Leu Gln Ile Lys Asn Met Gln His Leu Gln Lys Phe
        195                 200                 205

Leu Glu Pro Tyr His Lys Lys Thr Thr Phe Val Val Val Leu Asp Glu
    210                 215                 220

Met Asp Arg Leu Leu His Ala Asn Thr Ser Glu Thr Gln Ser Val Arg
225                 230                 235                 240
```

-continued

```
Thr Ile Leu Glu Leu Phe Leu Leu Ala Lys Leu Pro Thr Val Ser Phe
            245                 250                 255

Val Leu Ile Gly Met Ala Asn Ser Leu Asp Met Lys Asp Arg Phe Leu
            260                 265                 270

Ser Arg Leu Asn Leu Asp Arg Gly Leu Leu Pro Gln Thr Ile Val Glu
            275                 280                 285

Gln Pro Tyr Thr Ala Glu Gln Met Tyr Glu Ile Val Ile Gln Lys Met
        290                 295                 300

Ser Ser Leu Pro Thr Ile Ile Phe Gln Pro Met Ala Ile Lys Phe Ala
305                 310                 315                 320

Ala Lys Lys Cys Ala Gly Asn Thr Gly Asp Leu Arg Lys Leu Phe Asp
                325                 330                 335

Val Leu Arg Gly Ser Ile Glu Ile Tyr Glu Leu Glu Lys Arg Phe Leu
            340                 345                 350

Leu Ser Pro Thr Arg Gly Ser Leu Asn Ser Ala Gln Val Pro Leu Thr
            355                 360                 365

Pro Thr Thr Ser Pro Val Lys Lys Ser Tyr Pro Glu Pro Gln Gly Lys
        370                 375                 380

Ile Gly Leu Asn Tyr Ile Ala Lys Val Phe Ser Lys Phe Val Asn Asn
385                 390                 395                 400

Asn Ser Thr Arg Thr Arg Ile Ala Lys Leu Asn Ile Gln Gln Lys Leu
            405                 410                 415

Ile Leu Cys Thr Ile Ile Gln Ser Leu Lys Leu Asn Ser Asp Ala Thr
            420                 425                 430

Ile Asp Glu Ser Phe Asp His Tyr Ile Lys Ala Ile Thr Lys Thr Asp
            435                 440                 445

Thr Leu Ala Pro Leu Gln Arg Asn Glu Phe Leu Glu Ile Cys Thr Ile
        450                 455                 460

Leu Glu Thr Cys Gly Leu Val Ser Ile Lys Lys Thr Lys Cys Lys Gly
465                 470                 475                 480

Lys Thr Lys Arg Phe Val Asp Lys Ile Asp Val Asp Leu Asp Met Arg
                485                 490                 495

Glu Phe Tyr Asp Glu Met Thr Lys Ile Ser Ile Leu Lys Pro Phe Leu
            500                 505                 510

His
```